US010954491B2

(12) United States Patent
de Groof et al.

(10) Patent No.: US 10,954,491 B2
(45) Date of Patent: Mar. 23, 2021

(54) PESTIVIRUS

(71) Applicant: Intervet Inc., Madison, NJ (US)

(72) Inventors: Ad de Groof, Groesbeek (NL); Lars Guelen, Nijmegen (NL); Carla Christina Schrier, Boxmeer (NL); Martin Deijs, Huizen (NL); Cornelia Maria van der Hoek, Amsterdam (NL)

(73) Assignee: Intervet Inc., Madison, NJ (US)

( * ) Notice: Subject to any disclaimer, the term of this patent is extended or adjusted under 35 U.S.C. 154(b) by 452 days.

(21) Appl. No.: 15/535,819

(22) PCT Filed: Dec. 18, 2015

(86) PCT No.: PCT/EP2015/080400
§ 371 (c)(1),
(2) Date: Jun. 14, 2017

(87) PCT Pub. No.: WO2016/097245
PCT Pub. Date: Jun. 23, 2016

(65) Prior Publication Data

US 2017/0342387 A1 Nov. 30, 2017

(30) Foreign Application Priority Data

Dec. 19, 2014 (EP) .................................... 14199430

(51) Int. Cl.

| | |
|---|---|
| ***C12N 7/00*** | (2006.01) |
| ***G01N 33/569*** | (2006.01) |
| ***C12Q 1/70*** | (2006.01) |
| ***C07K 14/005*** | (2006.01) |
| ***C07K 16/10*** | (2006.01) |
| ***A61K 39/00*** | (2006.01) |

(52) U.S. Cl.
CPC .............. *C12N 7/00* (2013.01); *C07K 14/005* (2013.01); *C07K 16/10* (2013.01); *C12Q 1/701* (2013.01); *G01N 33/56983* (2013.01); *A61K 39/00* (2013.01); *C12N 2770/24321* (2013.01); *C12N 2770/24322* (2013.01); *C12N 2770/24334* (2013.01); *G01N 2333/183* (2013.01)

(58) Field of Classification Search
None
See application file for complete search history.

(56) References Cited

U.S. PATENT DOCUMENTS

2017/0342387 A1* 11/2017 de Groof .............. C12Q 1/701

OTHER PUBLICATIONS

Groof et al. "Atypical Porcine Pestivirus: A Possible Cause of Congenital Tremor Type A-II in Newborn Piglets", Viruses 2016; 8(271): 1-13.*
Sequence alignment SEQ ID No. 3 with GenEmbl database access No. KX929073 Sep. 2016.*
Tomiya et al. (Glycoconjugate Journal. 2004; 21: 343-360).*
De Pourcq et al. (Applied Microbiology and Biotechnology. 2010; 87 (5): 1617-1631).*
Blomström, A-L. et al., Astrovirus as a possible cause of congenital tremor type AII in piglets, ACTA Veterinaria Scandinavica, 2014, p. 82, 56.
Bolske, G et al, Congenital Tremor in Pigs in Sweden, Nord. Vet.-Med., 1978, pp. 534-537, vol. 30.
Congenital Tremor (CT)—Shaking Piglets, www.thepigsite.com, http://www.thepigsite.com/diseaseinfo/27/congenital-tremor-ct-shaking-piglets, Dec. 30, 2014.
Congenital Tremor—Shaking Piglets, www.thepigsite.com, http://www.thepigsite.com/pighealth/article/274/congenital-tremor-ct-shaking-piglets, Dec. 30, 2014.
Done, J.T. et al., Porcine congenital tremor type AII: spinal cord morphometry, British Veterinary Journal, 1986, pp. 145-150, 142,2.
Done, J.T., Congenital nervous diseases of pigs: a review, Laboratory Animals, 1968, pp. 207-217, 2.
Done, J.T., Harding, J.D., Kongenitaler Tremor der Schweine (Zitterkrankheit der Ferkel): Veränderungen und Ursachen, Deutsche Tierärztliche Wochenschrift, 1967, pp. 333-336, article in German, 74(13).
European Search report for EP14199430, dated Dec. 8, 2015, 8 pages.
Goodwin, R.F.W. et al., Trembling in newborn pigs, Proceedings of the Royal Society of Medicine, 1956, pp. 979-980, 41-42.
Gripshover, E.M. et al., Variation in ERNS viral glycoprotein associated with failure of immunohistochemistry and commercial antigen capture ELISA to detect a field strain of bovine viral diarrhea virus, Veterinary Microbiology, 2007, pp. 11-21, 125.
Hause, B.M., et al., Discovery of a novel putative atypical porcine pestivirus in pigs in the USA, Journal of General Virology, 2015, pp. 2994-2998, 96.
International Search Report for PCT/EP2015/080400, dated Mar. 17, 2016, 13 pages.
Kennedy, S. et al., Absence of evidence of porcine circovirus infection in piglets with congenital tremors, Journal of Veterinary Diagnostic Investigation, 2003, pp. 151-156, 15.

(Continued)

*Primary Examiner* — Shanon A. Foley
(74) *Attorney, Agent, or Firm* — Sarah L. Hooson; Catherine D. Fitch

(57) ABSTRACT

The present invention relates to a novel porcine pestivirus, to proteins of the virus and to vaccines based upon the virus and proteins thereof. The invention also relates to DNA fragments comprising a gene of the virus and to DNA vaccines based upon genes of the virus. Furthermore the invention relates to antibodies that are reactive with the novel virus and to diagnostic tests for the detection of the virus or antibodies against the virus.

5 Claims, 11 Drawing Sheets

Figure 1:
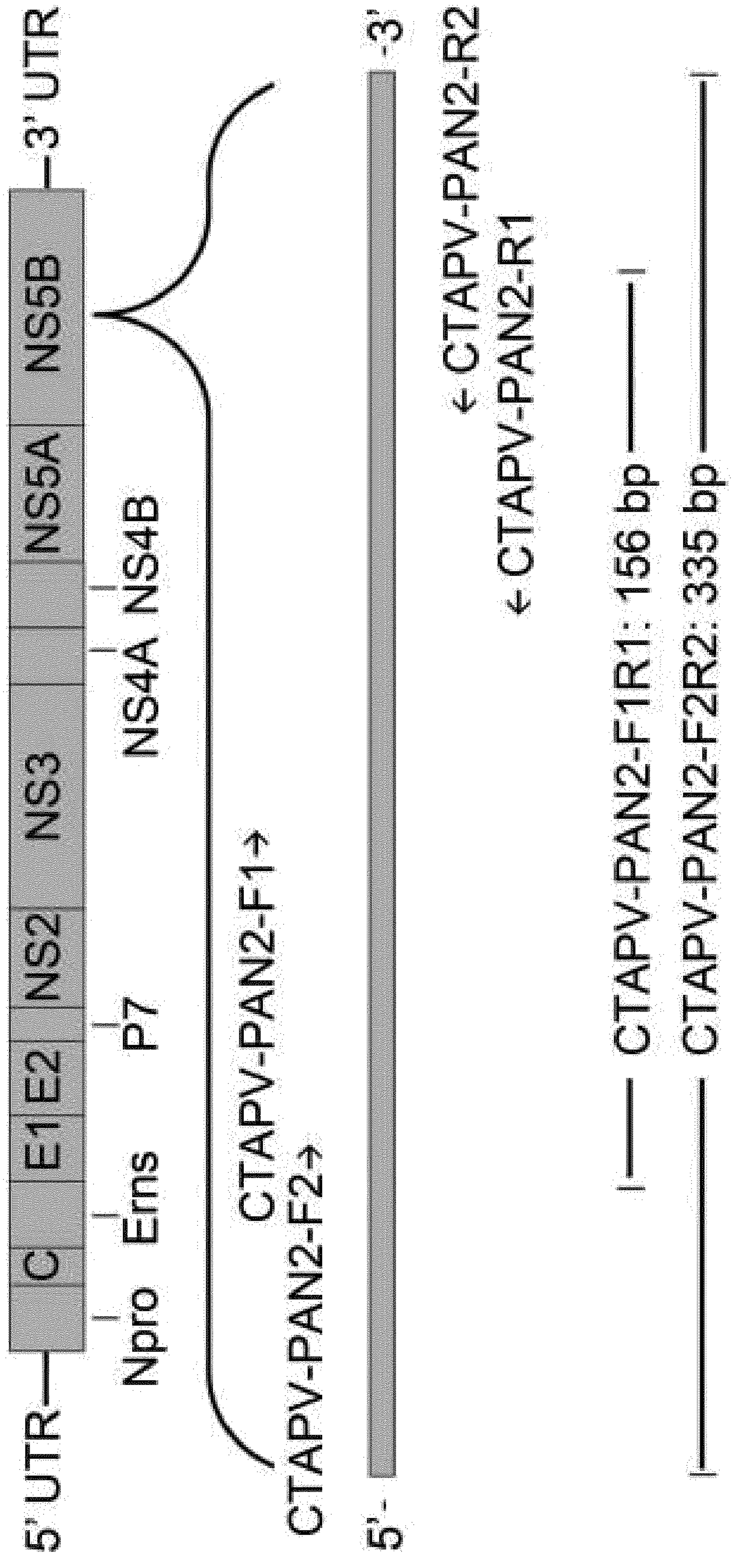

Specification includes a Sequence Listing.

(56) References Cited

OTHER PUBLICATIONS

Maplesden et al, Myoclonia Congenita in a Litter of, Can J Comp Med vet Sci, May 1957, pp. 170-172, vol. XXI, No. 5.
Patterson, D.S.P. et al., Neurochemistry of the spinal cord in congenital tremor of piglets (type All), a spinal dysmyelimogenesis of infectious origin, Journal of Neurochemistry, 1976, pp. 481-485, vol. 26.
Stevenson, G.W. et al., Tissue distribution and genetic typing of porcine circoviruses in pigs with naturally occurring congenital tremors, J. Vet Diagn Invest, 2001, pp. 57-62, 13.
White, M., Pig Health—Congenital Tremor, National Animal Disease Information Service website, http://www.nadis.org.uk/bulletins/congenital-tremor.aspx, 2014.
Wu, Z. et al, Virome Analysis for Identification of Novel Mammalian Viruses in Bat Species from Chinese Provinces, Journal of Virology, Aug. 2012, pp. 10999-11012, vol. 86, No. 20.

* cited by examiner

Border Disease Virus NC003679.1 GI:20198945
Pestivirus Reindeer-1 AF144618.2 GI:15282443
Classical Swine Fever Virus KC851953.1 GI:564113492
Pestivirus strain Aydin NC 018713.1 GI:408355343
Pestivirus Giraffe-1 NC 003678.1 GI:20178632
Bovine viral diarrhea virus 3 NC 012812.1 GI:240114604
Bovine viral diarrhea virus 1 KC853441.1 GI:507144147
Bovine viral diarrhea virus 2 NC 002032.1 GI:9629506
Pronghorn antelope pestivirus NC 024018.2 GI:704698593
Porcine pestivirus isolate Bungowannah NC 023176.1 GI:570364810
Norway rat pestivirus NC 025677.1 GI:723633161
CTAPV 1
Hepatitis C virus genotype 1 NC 004102.1 GI:22129792

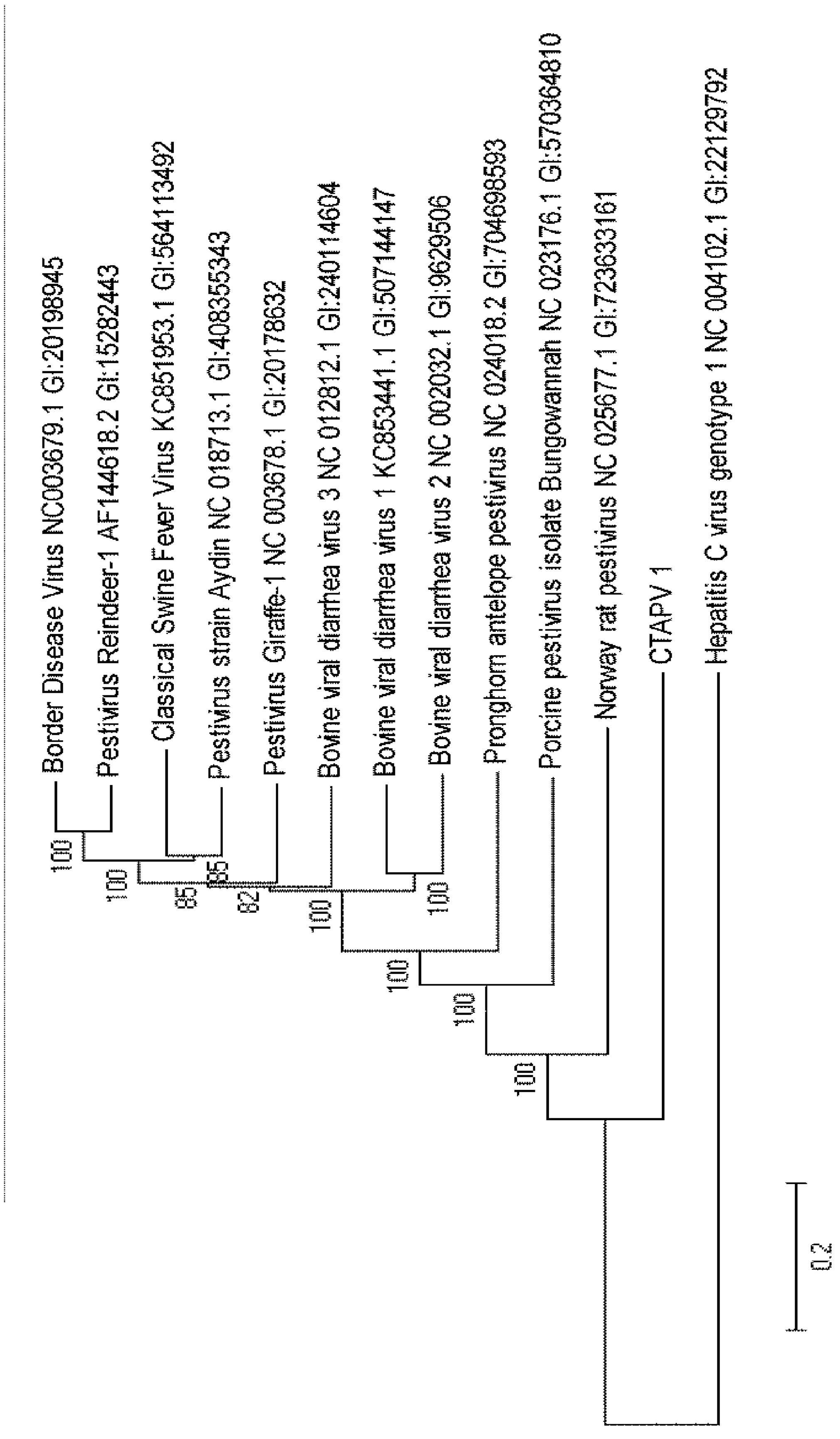

Figure 3.

Q:CTAPV 1B
S: CTAPV 1

Alignment statistics

| Score | Expect | Method | Identities | Positives | Gaps | Frame |
|---|---|---|---|---|---|---|
| 1334 bits(3452) | 0.0() | Compositional matrix adjust. | 648/648(100%) | 648/648(100%) | 0/648(0%) | |

Features:

```
Query  1    KVQWFLKDENSTGINQILWQRQINRTLHGEWPNQICHGMPNETITDEELRSLGMIDTSPR  60
            KVQWFLKDENSTGINQILWQRQINRTLHGEWPNQICHGMPNETITDEELRSLGMIDTSPR
Sbjct  1    KVQWFLKDENSTGINQILWQRQINRTLHGEWPNQICHGMPNETITDEELRSLGMIDTSPR  60

Query  61   TNYTCCQLQYHEWKKHGWCNYPQKQVWIRRITALQANLTGAYEGPECAVICRFNGSYNIV  120
            TNYTCCQLQYHEWKKHGWCNYPQKQVWIRRITALQANLTGAYEGPECAVICRFNGSYNIV
Sbjct  61   TNYTCCQLQYHEWKKHGWCNYPQKQVWIRRITALQANLTGAYEGPECAVICRFNGSYNIV  120

Query  121  KQARDEVSPLTGCKEGHPFLFSGERSDTSCLRPPSTSWVRPVKMDEASLADSFAHGVDKA  180
            KQARDEVSPLTGCKEGHPFLFSGERSDTSCLRPPSTSWVRPVKMDEASLADSFAHGVDKA
Sbjct  121  KQARDEVSPLTGCKEGHPFLFSGERSDTSCLRPPSTSWVRPVKMDEASLADSFAHGVDKA  180

Query  181  IILIRKGASGIINFLDTIGRWLPVAEAAIVPYCETYTVTGMYVHVKNCLPRGLPKHSKII  240
            IILIRKGASGIINFLDTIGRWLPVAEAAIVPYCETYTVTGMYVHVKNCLPRGLPKHSKII
Sbjct  181  IILIRKGASGIINFLDTIGRWLPVAEAAIVPYCETYTVTGMYVHVKNCLPRGLPKHSKII  240

Query  241  SPTIIYLGEGDPAHNIQHLFGSGIAKWVLVLLGVLGEWYGELASTIYLLLEYGSEWLEHE  300
            SPTIIYLGEGDPAHNIQHLFGSGIAKWVLVLLGVLGEWYGELASTIYLLLEYGSEWLEHE
Sbjct  241  SPTIIYLGEGDPAHNIQHLFGSGIAKWVLVLLGVLGEWYGELASTIYLLLEYGSEWLEHE  300

Query  301  SLVTEGLIPGINITIELPASHTVPGWVWVAGRWVCVKPDWWPTQIWIETIVAEVWHILKI  360
            SLVTEGLIPGINITIELPASHTVPGWVWVAGRWVCVKPDWWPTQIWIETIVAEVWHILKI
Sbjct  301  SLVTEGLIPGINITIELPASHTVPGWVWVAGRWVCVKPDWWPTQIWIETIVAEVWHILKI  360

Query  361  LASALVNIVTAFVNLELVYLVIILVKISKGNLIGAILWCLLLSGAEGSCHKRQDYYSIQL  420
            LASALVNIVTAFVNLELVYLVIILVKISKGNLIGAILWCLLLSGAEGSCHKRQDYYSIQL
Sbjct  361  LASALVNIVTAFVNLELVYLVIILVKISKGNLIGAILWCLLLSGAEGSCHKRQDYYSIQL  420

Query  421  VVDGKTGVEKRSIVGKWTVITREGREPRLMEQISMVSNDSLSETYCYNRLNTSSWGRQPA  480
            VVDGKTGVEKRSIVGKWTVITREGREPRLMEQISMVSNDSLSETYCYNRLNTSSWGRQPA
Sbjct  421  VVDGKTGVEKRSIVGKWTVITREGREPRLMEQISMVSNDSLSETYCYNRLNTSSWGRQPA  480

Query  481  RQRGCGQTVPFWPGDNVLEEQYYSTGYWVNATGGCQLREGVWLSRKGNVQCQRNGSSLIL  540
            RQRGCGQTVPFWPGDNVLEEQYYSTGYWVNATGGCQLREGVWLSRKGNVQCQRNGSSLIL
Sbjct  481  RQRGCGQTVPFWPGDNVLEEQYYSTGYWVNATGGCQLREGVWLSRKGNVQCQRNGSSLIL  540

Query  541  QLAIKEENDTMEIPCDPVETESMGPVTQGTCVYSWAFAPRGWYYNRKDGYWLQYVKKNDY  600
            QLAIKEENDTMEIPCDPVETESMGPVTQGTCVYSWAFAPRGWYYNRKDGYWLQYVKKNDY
Sbjct  541  QLAIKEENDTMEIPCDPVETESMGPVTQGTCVYSWAFAPRGWYYNRKDGYWLQYVKKNDY  600

Query  601  QYWTKMPTASSATTMYRHLLPLLVACLMGGRISVWIVAMLLSLQVEAS  648
            QYWTKMPTASSATTMYRHLLPLLVACLMGGRISVWIVAMLLSLQVEAS
Sbjct  601  QYWTKMPTASSATTMYRHLLPLLVACLMGGRISVWIVAMLLSLQVEAS  648
```

Figure 5.

Q= CTAPV 1B
S= CTAPV 8

Alignment statistics for match #1

| Score | Expect | Method | Identities | Positives | Gaps | Frame |
|---|---|---|---|---|---|---|
| 1286 bits(3328) | 0.0() | Compositional matrix adjust. | 616/648(95%) | 635/648(97%) | 0/648(0%) | |

Features:

```
Query  1    KVQWFLKDENSTGINQILWQRQINRTLHGEWPNQICHGMPNETITDEELRSLGMIDTSPR  60
            KVQWFLKDENSTGI+QILWQRQI+R+LHGEWP+QICHGMPNETITDEELRSLGMIDTSPR
Sbjct  1    KVQWFLKDENSTGISQILWQRQISRSLHGEWPDQICHGMPNETITDEELRSLGMIDTSPR  60

Query  61   TNYTCCQLQYHEWKKHGWCNYPQKQVWIRRITALQANLTGAYEGPECAVICRFNGSYNIV  120
            TNYTCCQLQYHEWKKHGWCNYPQKQ WIRRITALQANLTGAYEGPECAVICRFNGSYNIV
Sbjct  61   TNYTCCQLQYHEWKKHGWCNYPQKQAWIRRITALQANLTGAYEGPECAVICRFNGSYNIV  120

Query  121  KQARDEVSPLTGCKEGHPFLFSGERSDTSCLRPPSTSWVRPVKMDEASLADSFAHGVDKA  180
            KQARDEVSPLTGCKEGHPFLFS ERSDTSCLRPPSTSWVRPVKMDEAS+AD FAHGVDKA
Sbjct  121  KQARDEVSPLTGCKEGHPFLFSDERSDTSCLRPPSTSWVRPVKMDEASMADGFAHGVDKA  180

Query  181  IILIRKGASGIINFLDTIGRWLPVAEAAIVPYCETYTVTGMYVHVKNCLPRGLPKHSKII  240
            IILIRKGASGIINFLDTIG WLPVAEA I PYCETYTVTGMYVHVKNCLP+GLPKHSKII
Sbjct  181  IILIRKGASGIINFLDTIGGWLPVAEATITPYCETYTVTGMYVHVKNCLPKGLPKHSKII  240

Query  241  SPTIIYLGEGDPAHNIQHLFGSGIAKWVLVLLGVLGEWYGELASTIYLLLEYGSEWLEHE  300
            SPT+IYLGEGDPAHNIQHLFGSGIAKWVLVLLGVLGEWYGELASTIYLLLEY SEWLEHE
Sbjct  241  SPTMIYLGEGDPAHNIQHLFGSGIAKWVLVLLGVLGEWYGELASTIYLLLEYESEWLEHE  300

Query  301  SLVTEGLIPGINITIELPASHTVPGWVWVAGRWVCVKPDWWPTQIWIETIVAEVWHILKI  360
            SL+TEGLIPGINITIELPASHTVPGWVWVAG+WVCVKPDWWPTQIWIET+VAE WHILKI
Sbjct  301  SLITEGLIPGINITIELPASHTVPGWVWVAGQWVCVKPDWWPTQIWIETVVAEAWHILKI  360

Query  361  LASALVNIVTAFVNLELVYLVIILVKISKGNLIGAILWCLLLSGAEGSCHKRQDYYSIQL  420
            LASALVNIVTAFVNLELVYLVIILVKISKGNLIGAILWCLLLSGAEGSCHKRQDYY+IQL
Sbjct  361  LASALVNIVTAFVNLELVYLVIILVKISKGNLIGAILWCLLLSGAEGSCHKRQDYYNIQL  420

Query  421  VVDGKTGVEKRSIVGKWTVITREGREPRLMEQISMVSNDSLSETYCYNRLNTSSWGRQPA  480
            VV+ KTGVEKRSI+GKWTVIT+EGREPRLMEQI+MVSNDSLSETYCYNRLNTSSW RQPA
Sbjct  421  VVEEKTGVEKRSIIGKWTVITKEGREPRLMEQINMVSNDSLSETYCYNRLNTSSWRRQPA  480

Query  481  RQRGCGQTVPFWPGDNVLEEQYYSTGYWVNATGGCQLREGVWLSRKGNVQCQRNGSSLIL  540
            +QRGCGQTVP+WPGDNVLEEQYYSTGYWVNATGGCQLREGVWLSRKGNVQCQRNGSSL+L
Sbjct  481  KQRGCGQTVPYWPGDNVLEEQYYSTGYWVNATGGCQLREGVWLSRKGNVQCQRNGSSLML  540

Query  541  QLAIKEENDTMEIPCDPVETESMGPVTQGTCVYSWAFAPRGWYYNRKDGYWLQYVKKNDY  600
            QLAIKEENDTMEIPCDPVETESMGPV QGTCVYSWAFAPRGWYYNRKDGYWLQY+KKNDY
Sbjct  541  QLAIKEENDTMEIPCDPVETESMGPVAQGTCVYSWAFAPRGWYYNRKDGYWLQYIKKNDY  600

Query  601  QYWTKMPTASSATTMYRHLLPLLVACLMGGRISVWIVAMLLSLQVEAS  648
            QYWTKMP ASSA TMYRHLLPLLVACLMGGRISVWIVAMLLSLQVEAS
Sbjct  601  QYWTKMPAASSAATMYRHLLPLLVACLMGGRISVWIVAMLLSLQVEAS  648
```

Figure 6.

CTAPV-Type1

AAGGTTCAGTGGTTCTTAAAGGACGAAAACTCGACGGGGATCAATCAGAT
CCTGTGGCAAAGACAGATTAACAGAACCCTGCATGGAGAATGGCCTAACC
AGATCTGCCATGGCATGCCAAATGAAACTATTACAGATGAGGAATTACGT
AGCCTGGGAATGATAGACACAAGCCCCAGAACAAACTACACTTGCTGCCA
GTTGCAATATCATGAATGGAAGAAACATGGTTGGTGCAACTATCCACAAA
AACAGGTCTGGATCAGGAGGATAACGGCCCTACAAGCTAACCTCACCGGA
GCCTATGAGGGGCCTGAGTGTGCCGTCATTTGTAGATTTAACGGCAGCTA
TAACATCGTAAAACAAGCCAGAGATGAGGTGAGTCCACTGACAGGGTGCA
AGGAAGGGCACCCTTTTCTATTCTCTGGTGAAAGATCCGACACCTCATGC
CTGAGGCCCCCTTCCACTAGTTGGGTAAGACCGGTAAAAATGGACGAGGC
GTCATTGGCTGATAGCTTCGCCCATGGGGTTGACAAGGCAATAATACTAA
TCAGAAAAGGGGCATCAGGAATAATTAATTTCCTAGACACTATTGGGAGG
TGGCTACCGGTAGCTGAGGCAGCTATAGTACCATATTGTGAAACTTACAC
TGTGACAGGGATGTATGTCCATGTGAAGAATTGTCTCCCTAGAGGGTTAC
CGAAGCATTCAAAGATAATTTCCCCGACAATAATATACTTGGGGGAAGGT
GACCCAGCCCATAATATTCAGCACTTATTTGGCTCAGGTATAGCAAAGTG
GGTCTTAGTCCTACTCGGGGTTCTGGGTGAGTGGTATGGAGAATTGGCCT
CTACAATATACTTACTACTAGAGTATGGGTCTGAGTGGTTGGAACATGAA
AGTCTGGTCACGGAAGGGTTGATCCCTGGCATCAATATTACAATAGAACT
CCCAGCTAGTCATACTGTACCTGGTTGGGTGTGGGTCGCAGGCCGGTGGG
TATGCGTGAAACCAGATTGGTGGCCCACACAGATTTGGATTGAAACTATA
GTGGCAGAGGTCTGGCATATACTAAAAATATTGGCATCAGCCCTGGTAAA
CATAGTCACTGCATTCGTAAACCTGGAATTGGTATACCTGGTCATAATAT
TAGTCAAAATATCAAAGGGGAACCTGATAGGCGCTATATTGTGGTGCCTA
TTACTGTCAGGGGCTGAAGGC*TCGTGCCACAAGAGACAAGACTATTACAG*
*TATCCAGCTAGTCGTTGACGGAAAAACGGGCGTAGAAAAACGATCTATAG*
*TGGGCAAGTGGACAGTGATAACTAGGGAAGGTCGGGAACCAAGATTAATG*
*GAGCAAATAAGCATGGTGTCAAATGATAGCTTATCAGAAACTTACTGCTA*
*CAATAGGCTAAATACTAGCAGTTGGGGGCGACAACCGGCAAGACAGAGAG*
*GGTGTGGTCAAACCGTACCCTTTTGGCCTGGTGACAATGTCCTGGAAGAA*
*CAATACTATAGCACAGGTTACTGGGTAAATGCAACAGGTGGTTGCCAGTT*
*GAGAGAAGGCGTGTGGCTATCAAGAAAGGGCAATGTACAGTGCCAGCGTA*
*ACGGCTCATCCTTGATACTGCAACTGGCGATAAAAGAAGAGAATGACACT*
*ATGGAAATACCATGTGACCCGGTGGAAACCGAAAGTATGGGTCCAGTTAC*
*ACAGGGCACTTGCGTGTACAGCTGGGCATTCGCCCCAAGAGGGTGGTATT*
*ACAACAGGAAAGATGGTTATTGGCTCCAGTACGTAAAGAAAAACGACTAC*
*CAGTACTGGACGAAAATGCCCACTGCTTCATCCGCCACAACGATGTACCG*
*CCAT*TTGCTCCCTTTACTGGTGGCCTGCCTCATGGGCGGTAGAATATCGG
TATGGATTGTGGCGATGCTCCTGTCTTTACAGGTGGAAGCTAGT $E^{rns}$ thick underlined
E1 thin underlined
E2 in Italic.
Sequence starts at nt 1259 of the reference genome.

Figure 8.

C

PESTIVIRUS

CROSS-REFERENCE TO RELATED APPLICATIONS

This application is a national stage entry under 35 U.S.C. § 371 of PCT/EP2015/080400 filed on Dec. 18, 2015, which claims priority to EP 14199430.1, filed on Dec. 19, 2014. The content of PCT/EP2015/080400 is hereby incorporated by reference in its entirety.

The present invention relates to a novel pestivirus, to proteins of the virus and to vaccines based upon the virus and proteins thereof. The invention also relates to DNA fragments comprising a gene of the virus and to DNA vaccines based upon genes of the virus. Furthermore the invention relates to antibodies that are reactive with the novel virus and to diagnostic tests for the detection of the virus or antibodies against the virus.

Over the last decades, world-wide a strong increase is seen in the consumption of pig meat. As a consequence, an increase is seen in the number and the size of farms, in order to meet the increasing needs of the market. As is known from animal husbandry in general, large numbers of animals living closely together are vulnerable to known diseases and to diseases hardly known or seen or even unknown before the days of large-scale commercial farming.

One disease for which the causative agent awaits identification is known to exist already since the early 20$^{th}$ century, when "dancing pigs" were mentioned by Kinsley in Veterinary Medicine 1922; 17. Over the course of nearly a century several articles have been published that describe the same symptoms under varying names, including "shaking pig disease", tremor in pigs, *Myoclonia Congenita*[(1)] or congenital tremor (CT)[(2)]. The disease will further be referred to as CT. Symptoms of CT are tremors of the head and legs of newborn pigs that vary in severity but are absent during sleep. These tremors can be aggravated by excitement and cold. They last for several weeks to months but decrease as the pigs grow older. Although the shaking itself does not directly cause death the tremors can prevent the piglets from finding a teat to suckle. This can then result in death by starvation. The disease is widespread and occurs regularly in pig farms all over the world.

Several conditions are known to cause CT, and currently these conditions are classified in two groups; A and B. Group A consists of the cases with visible histological lesions, whereas the cases of Group B display no apparent lesions. Group A is further divided into five subgroups, based on the different causes of CT. Group A-I cases of CT are known to be caused by Classical Swine Fever (CSF) virus. The cause of Group A-III CT is a genetic (sex-linked) defect existing only in the Landrace breed, while a recessive genetic (autosomal-linked) defect in the Saddleback breed is the cause of type A-IV. Group A-V cases are caused by trichlorfon toxicosis, an intoxication which is often linked to organophosphorus treated food[(3, 4)].

Group A-II cases have been, and still are, the most puzzling cases. They are suspected to be caused by an unknown infectious agent.

Although Group A-II CT has been associated with PCV infection in the past[(5)], various studies have now demonstrated the opposite. For example, PCV is absent in neuronal tissue of pigs with CT[(6)] and only a small, insignificant, amount of PCV was found in non-neuronal tissue[(4)]. All in all no conclusive evidence exists so far for the cause of Group A-II CT. There is sufficient reason to believe, however, that Group A-II CT is caused by an infectious agent.

Most of the Group A-II shaking piglets are born into the litters of gilts (i.e. female pigs in the period between fertilisation and their first litter) that have recently been introduced into a new environment. Remarkably, after a first litter with shaking piglets subsequent litters of the same sow hardly ever show signs of CT. This is an indication that some kind of immunity develops in the sow, protecting against the agent that causes CT. Some 40 years ago, Patterson et al. (50) managed to induce Group A-II CT in piglets through experimental infection of pregnant sows with an emulsion of spinal cord, brains and spleens of clinically affected pigs.

But as indicated above, no causative infectious agent has ever been isolated from CT piglets nor from pregnant sows.

It is an objective of the present invention to provide a new infectious agent that is the causative agent of Group A-II CT, as well as vaccines aiming at combating the disease. Moreover, it is an objective of the present invention to provide means to detect and identify the disease-associated infectious agent.

In order to finally detect and isolate the causative agent of Group A-II CT, sera and in many cases additional biological material of piglets suffering from Group A-II CT were obtained from September of 2012 until early 2014, on 8 different farms in the Netherlands. These 8 farms had a history of CT-piglets (Typically in one out of four litters, piglets are found suffering from CT during an epidemic peak on one specific farm).

A pig farm in the Netherlands was diagnosed with an outbreak of congenital tremor type A-II in early 2012. Piglets born from gilt, first parity animals, were primarily affected but also higher parity sows were occasionally affected. Diagnosis was based on clinical observations and subsequent exclusion of congenital tremor types A-I, A-III, A-IV and A-V as the possible cause for disease. Clinically affected piglets showed tremor in different grades, due to excessive muscle contractions during activity. The symptoms diminished when sleeping. Piglet loss was a secondary effect caused by the inability of affected animals to feed themselves, especially during the first week after birth. Histologically, the brain and the spinal cord were characterized by hypomyelinization. (Histological abnormalities are however not always seen in affected piglets. In the literature, the extent of hypomyelinization is also described as being variable). As further described below, not all affected pigs survived. In those that survived, the tremor diminished and finally disappeared as pigs grew older. In the first 20 weeks of the year 2012, a total of 48 litters with symptoms of congenital tremor were born from gilts, out of 231 µlitters born from gilts in total. This equals 21% of all litters born from gilts. At the peak of infection, 8 weeks after the initial outbreak, 85% of the gilt litters showed piglets with congenital tremor type A-II. The percentage piglet loss (piglet death) till weaning was 26% in affected litters, compared to 11% in non-affected litters. In affected litters, 60% of piglet death was attributable to congenital tremor. The total number of piglets born per litter was not affected. Congenital tremor affected both newborn male and female piglets, and prevalence within the litter varied between <10%-100%.

Problems with outbreaks of congenital tremor have continued on this farm since 2012, and affected piglets were obtained in 2013 and 2014 (see below). However, the incidence rate decreased.

Blood plasma samples were obtained in March 2012 (6 samples, all piglets with symptoms of CT where non-A-II causes could be excluded) and April 2012 (5 samples, all piglets with symptoms of CT where non-A-II causes could be excluded). A new virus, temporarily called "Michael" (M) was detected in 11/11 samples.

More blood plasma samples were obtained from the same farm in July 2012. A total of 16 serum samples from piglets born from 2 sows and 1 gilt were analyzed. None of these piglets showed congenital tremor. Michael 1 was found in 1/16 samples.

A new outbreak of the disease was diagnosed in January 2013. Four newborn pre-colostral piglets were obtained for necropsy, all showed symptoms of CT where non-A-II causes could be excluded. The new virus was named Michael 1A because, although it originated from the same farm, significant time had elapsed between the original outbreak and the occurrence of new clinical problems. The new virus Michael 1A was detected in 4/4 piglets.

Again a new outbreak of the disease was diagnosed in March 2013. Three newborn pre-colostral piglets were obtained for necropsy, all showed symptoms of CT where non-A-II causes could be excluded. This virus was named Michael 1B (M1B). The new virus Michael 1B was detected in 3/3 samples. Brains and spinal cord showed signs of demyelinization (see FIG. 2).

A new outbreak of the disease was diagnosed in January 2014. Four newborn pre-colostral piglets were obtained, all showing symptoms of CT where non-A-II causes could be excluded. This virus was named Michael 1C (M1C). The new virus Michael 1C was detected in 4/4 samples. Necropsy on an additional 3 piglets was performed in February 2014, again all 3 piglets showed Group A-II CT, and Michael was detected in 3/3 samples.

Post mortem examination was performed on piglets from outbreaks in January 2013, March 2013 and February 2014. Brains and spinal cord showed signs of demyelinization.

A total of 7 sera obtained from newborn pre-colostral piglets from a farm with no history of congenital tremor type A-II was used as negative control for PCR and for post mortem examination. All plasma samples were negative for Michael virus, and no pathological abnormalities were observed in these piglets.

Comparable analysis of Group A-II CT outbreaks was done on 7 other farms in the Netherlands. Samples of CT-litters were analysed and the novel virus was found in 100% of the CT-piglets from which pre-colostral material was taken (material taken before the first ingestion of colostrum or mother milk).

The novel virus according to the invention is not yet officially classified, but for the moment the virus is best referred to as "Group A-II congenital tremor associated porcine pestivirus". The virus will also be referred to as CTAPV below.

The sequence of the viral genome was analysed and revealed that the novel virus unexpectedly bears some albeit a relatively low level of resemblance to the family of Flaviviridae, more specifically to the genus Pestivirus within this family. Known members of the genus Pestivirus are Classical Swine Fever virus, Bovine Viral Diarrhea virus and Border Disease virus.

Pestivirus virions are about 50 nm in diameter, spherical and enveloped, and they comprise a single stranded positive-sense RNA which is around 12 kilobases (kb) long.

The full length DNA sequence of a representative of the new virus is presented in SEQ ID NO: 19.

The genetic organization of the novel virus closely follows that of the known pestiviruses (see FIG. 1). The pestivirus genome encodes a single polyprotein NH2-C-$E^{rns}$-E1-E2-p7-NS2-NS3-NS4a-NS4b-NS5a-NS5b-COOH that is processed co- and post-translationally into both structural proteins ("Core" protein (C), and proteins $E^{rns}$, E1 and E2) and non-structural (NS) proteins. The amino-terminal part of the polyprotein is cleaved by host cell proteases and its cleavage products, core and envelope ($E^{rns}$, E1 and E2) proteins are believed to be the major constituents of pestivirus particles (virions).

The structural protein $E^{rns}$, also known as E0 or gp44/48 is an envelope protein with the unique property of having RNase activity (12). It is secreted from infected cells in a relatively large amount (13). However, an even larger amount remains membrane bound (14). One of the roles of $E^{rns}$ appears to be in interfering with the host immune system by inhibiting the interferon response using its RNase activity (15). Such a role in virulence is further supported by the fact that viral strains that are missing $E^{rns}$ become attenuated (16). E1 and E2, previously known as gp33 and gp55 (and previously confusingly also as E1), respectively, are the other two envelope glycoproteins. The structural protein E2 forms homodimers and heterodimers with E1 (17, 18). Especially heterodimers of E1 and E2 protein are important for pestiviruses to enter their host, whereas $E^{rns}$ does not seem to be required for virus entry (19, 20). Neutralizing antibodies primarily target $E^{rns}$ and E2, and to a lesser extend to E1 (17, 21).

The gene encoding the envelope protein $E^{rns}$ consisting of 216 amino acids is found at position 1258-1899 of SEQ ID NO: 19 and the gene encoding the envelope protein E2 consisting of 211 amino acids is found at position 2479-3111 of SEQ ID NO: 19. The gene encoding the envelope protein E1 consisting of 193 amino acids is found at position 1900-2478 of SEQ ID NO: 19.

An example of the DNA sequence of the gene encoding the envelope protein $E^{rns}$ is depicted in SEQ ID NO: 1. SEQ ID NO: 2 represents the amino acid sequence of the $E^{rns}$ protein.

An example of the DNA sequence of the gene encoding the envelope protein E2 is depicted in SEQ ID NO: 3. SEQ ID NO: 4 represents the amino acid sequence of the E2 protein.

An example of the DNA sequence of the gene encoding the envelope protein E1 is depicted in SEQ ID NO: 5. SEQ ID NO: 6 represents the amino acid sequence of the E1 protein.

The full sequences of the novel virus was used to make phylogenetic trees based on the Maximum Likelihood method, the Poisson correction model and bootstrap analysis (500 replicates).

These trees were made using the program MEGA, version 5, using standard settings. (MEGA5: Molecular Evolutionary Genetics Analysis Using Maximum Likelihood, Evolutionary Distance, and Maximum Parsimony Methods. Koichiro Tamura, Daniel Peterson, Nicholas Peterson, Glen Stecher, Masatoshi Nei and Sudhir Kumar. Mol. Biol. Evol. 28(10): 2731-2739. 2011 doi:10.1093/molbev/msr121 Advance Access publication May 4, 2011).

The phylogenetic tree based upon the whole sequence of the novel pestivirus is presented in FIG. 3. The percentage bootstrap support is specified at the nodes. Distance bars indicate the number of nucleotide substitutions per site.

It is clear from FIG. 3, that whereas the pestiviruses Border Disease virus, pestivirus of reindeer, classical swine fever virus, bovine viral diarrhea virus, pestivirus of giraffe and Bungowannah virus are relatively closely related, the novel virus according to the invention is more distantly related to each of these viruses.

Figure 4:
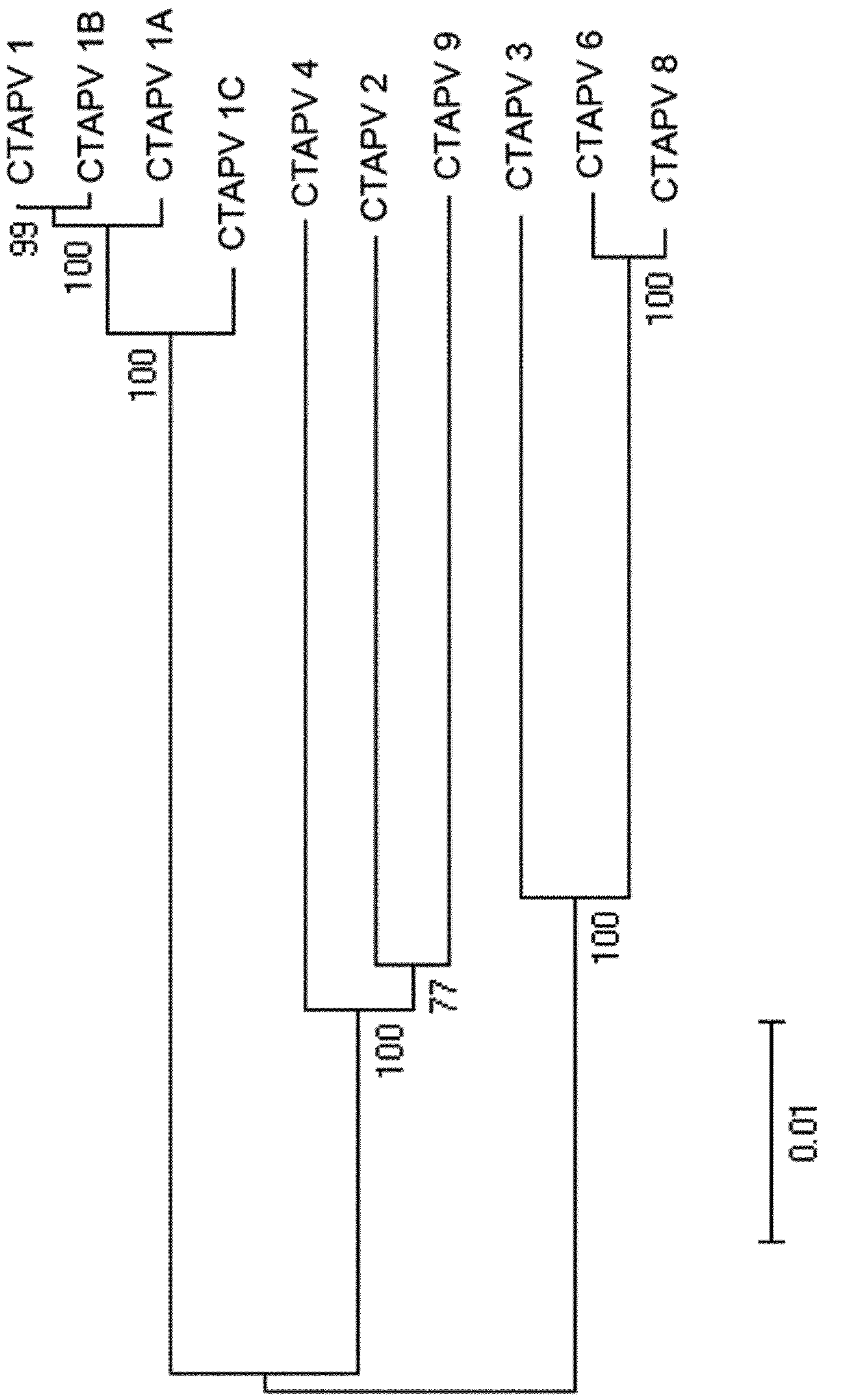

In FIG. 4, a phylogenic tree is presented wherein 10 different isolates of the virus according to the invention are compared.

It can be seen that the isolates M1, M1A, M1B and M1C (SEQ ID NO: 19, 20, 21, 22), isolated on the same farm, but over three years, are the most closely related to each other. Isolates from other farms show a somewhat greater variation. M2, M4 and M9 (SEQ ID NO: 23, 25, 29) are more related to each other than to the M1 group. The same is true for both M3, M6 and M8 (SEQ ID NO: 24, 26, 28). M7 (SEQ ID NO: 27) is not included. This indicates that there are small genetic changes between isolates. This is to be expected for RNA viruses, and this observation is in line with what is seen for other pestiviruses.

SEQ ID NO: 1, 3 and 5 show typical examples of the nucleotide sequence of the genes encoding $E^{rns}$, E2 and E1 of a virus according to the invention respectively.

SEQ ID NO: 2, 4 and 6 show typical examples of the amino acid sequence of an $E^{rns}$, E2 and E1 protein of a virus according to the invention respectively.

It will be understood that for these proteins natural variations can exist between individual representatives of the Group A-II congenital tremors-associated virus. Genetic variations leading to minor changes in e.g. the $E^{rns}$, E2 and E1 amino acid sequence do exist. First of all, there is the so-called "wobble in the second and third base" explaining that nucleotide changes may occur that remain unnoticed in the amino acid sequence they encode: e.g. triplets TTA, TTG, TCA, TCT, TCG and TCC all encode Leucine. In addition, minor variations between representatives of the novel porcine pestivirus according to the invention may be seen in amino acid sequence. These variations can be reflected by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science 227, 1435-1441, 1985) and determining the functional similarity between homologous proteins. Such amino acid substitutions of the exemplary embodiments of this invention, as well as variations having deletions and/or insertions are within the scope of the invention.

This explains why $E^{rns}$, E2 and E1, when isolated from different representatives of a porcine pestivirus according to the invention, may have homology levels that are significantly below 100%, while still representing the $E^{rns}$, E2 and E1 of the novel pestivirus according to the invention.

This is clearly reflected e.g. in the phylogenetic tree for the pestiviral gene $N^{pro}$ in Becher, P. et al.[(49)], where it is shown that highly related pestiviruses nevertheless have significantly different overall genomic nucleotide sequences as well as significantly different $N^{pro}$ gene nucleotide sequences.

Thus, a first embodiment of the present invention relates to an isolated virus which is a member of the pestiviruses, wherein the virus is characterized in that a) the virus is the causative agent of Group A-II congenital tremors in pigs and b) the virus has a viral genome comprising a gene encoding an envelope protein $E^{rns}$, a gene encoding an envelope protein E2 and a gene encoding an envelope protein E1, wherein the nucleotide sequence of the $E^{rns}$ gene has a level of identity of at least 80% to the nucleotide sequence as depicted in SEQ ID NO: 1 and/or the nucleotide sequence of the E2 gene has a level of identity of at least 80% to the nucleotide sequence as depicted in SEQ ID NO: 3 and/or the nucleotide sequence of the E1 gene has a level of identity of at least 80% to the nucleotide sequence as depicted in SEQ ID NO: 5.

For the purpose of this invention, a level of identity is to be understood as the percentage of identity between e.g. the sequence of SEQ ID NO: 1 and the corresponding region encoding the $E^{rns}$ of a pestivirus of which the level of identity is to be determined.

A suitable program for the determination of a level of identity is the nucleotide blast program (blastn) of NCBI's Basic Local Alignment Search Tool, using the "Align two or more sequences" option and standard settings (http://blast.ncbi.nlm.nih.gov/Blast.cgi).

For the purpose of this invention, isolated means: set free from tissue with which the virus is associated in nature. An example of an isolated virus is the virus as present in cell culture.

A preferred form of this embodiment relates to such a virus that has an $E^{rns}$ gene that has a level of identity of at least 82%, more preferably 84%, 86%, 88%, 90%, 91%, 92%, 93%, 94%, 95%, 96%, 97%, 98%, 99% or even 100%, in that order of preference, to the nucleotide sequence of the $E^{rns}$ as depicted in SEQ ID NO: 1.

Another preferred form of this embodiment relates to such a virus that has an E2 gene that has a level of identity of at least 82%, more preferably 84%, 86%, 88%, 90%, 91%, 92%, 93%, 94%, 95%, 96%, 97%, 98%, 99% or even 100%, in that order of preference, to the nucleotide sequence of the E2 gene as depicted in SEQ ID NO: 3.

Again another preferred form of this embodiment relates to such a virus that has an E1 gene that has a level of identity of at least 82%, more preferably 84%, 86%, 88%, 90%, 91%, 92%, 93%, 94%, 95%, 96%, 97%, 98%, 99% or even 100%, in that order of preference, to the nucleotide sequence of the E1 gene as depicted in SEQ ID NO: 5.

A more preferred form of this embodiment relates to an isolated virus which is a member of the pestiviruses, said virus being characterized in that a) the virus is the causative agent of Group A-II congenital tremors in pigs and b) the virus has a viral genome comprising a gene encoding an envelope protein $E^{rns}$, a gene encoding an envelope protein E2 and a gene encoding an envelope protein E1, wherein the nucleotide sequence of the $E^{rns}$ gene has a level of identity of at least 80% to the nucleotide sequence as depicted in SEQ ID NO: 1 and the nucleotide sequence of the E2 gene has a level of identity of at least 80% to the nucleotide sequence as depicted in SEQ ID NO: 3 and the nucleotide sequence of the E1 gene has a level of identity of at least 80% to the nucleotide sequence as depicted in SEQ ID NO: 5.

Another, alternative, way to characterize the virus according to the invention depends on a PCR-test using primer sets that are specific for the NS5B gene sequence or the 5'UTR sequence of a virus according to the invention.

An overview of the various primers and the size of the PCR products made using these primers are represented in table a and b.

Four different primer sets of which the sequence is depicted in SEQ ID NO: 7-8, SEQ ID NO: 9-10, SEQ ID NO: 11-12 and SEQ ID NO: 13-14 were elected for their specificity for the NS5B region of the virus. The PCR-tests using the first primer set (SEQ ID NO: 7-8), the second primer set (SEQ ID NO: 9-10), and the combination of the forward and reverse primers that specifically reacts with the NS5B gene of the virus, use the following two primer pairs F1-R1, F2-R2, F1-R2 and F2-R1 respectively.

The primer sets SEQ ID NO: 11-12 (PAN-FW and PAN-REV) and SEQ ID NO: 13-14 (PANdeg-FW and PANdeg-REV) also specifically react with NS5B. The set with degenerate primers SEQ ID NO: 13-14 was designed to increase the chance of finding CTAPV variants with slightly altered RNA sequences.

The PCR-test using primer set (SEQ ID NO: 15-16) specifically reacts with the 5' UTR of the virus and uses the two primers F3-R3.

The PCR-test using primer set (SEQ ID NO: 17-18) also specifically reacts with the 5' UTR of the virus and uses the two primers F4-R4

The tests, which are described in more detail in the Examples section, are standard PCR tests on cDNA. (It goes without saying that, since the virus has an RNA genome, the viral RNA was first transcribed into cDNA in a reverse transcriptase reaction. The cDNA was used for the PCR reactions).

TABLE b

| Primer combination | Anneal temperature (° C.) | PCR product size (bp) | Target |
|---|---|---|---|
| F1-R1 | 60.2 | 156 | NS5B |
| F1-R2 | 60.2 | 277 | NS5B |
| F2-R1 | 50.9 | 213 | NS5B |
| F2-R2 | 50.9 | 335 | NS5B |
| PAN-FW-PAN-RV | 58.0 | 896 | NS5B |
| PANdeg-FW-PANdeg-RV | 58.0 | 896 | NS5B |
| F3-R3 | 50.0 | 182 | 5'-UTR |
| F4-R4 | 50.0 | 182 | 5'-UTR |

If a virus is characterised using the primer sets described above, the following can be said: if an analysis of the PCR-product of e.g. the F1-R1 primer set reveals a PCR product of approximately 156 base pairs or if analysis of the PCR-product of e.g. the primer F2-R2 set reveals a PCR product of approximately 335 base pairs, this unequivocally demonstrates that the analysed virus belongs to the virus according to the invention.

Merely as an example: a PCR product of approximately 156 base pairs is a PCR product with a length of between 156+10 and 156-10 base pairs. A PCR product of approximately 335 base pairs is a PCR product with a length of between 335+10 and 335-10 base pairs.

Thus another form of this embodiment of the present invention relates to an isolated virus which is a member of the Pestiviruses, characterized in that:

a) the virus is the causative agent of Group A-II congenital tremors in pigs and b) the cDNA reverse-transcribed from the viral RNA genome reacts in a PCR reaction with a primer set as depicted in SEQ ID NO: 7 and 8 to give a PCR product of 156+/−10 base pairs and/or reacts in a PCR reaction with a primer set as depicted in SEQ ID NO: 9 and 10 to give a PCR product of 335+/−10 base pairs and/or reacts in a PCR reaction with a primer set as depicted in SEQ ID NO: 11 and 12 to give a PCR product of 896+/−10 base pairs and/or reacts in a PCR reaction with a primer set as depicted in SEQ ID NO: 13 and 14 to give a PCR product of 896+/−10 base pairs and/or reacts in a PCR reaction with a primer set as depicted in SEQ ID NO: 15 and 16 to give a PCR product of 182+/−10 base pairs and/or reacts in a PCR reaction with a primer set as depicted in SEQ ID NO: 17 and 18 to give a PCR product of 182+/−10 base pairs.

TABLE a

| Primer name | Short name | Sequence primer | Pos. in SEQ ID NO: 19 |
|---|---|---|---|
| CTAPV-PAN2-F2 | F2 | CGGATACAGAAATACTAC | 10204-10221 |
| CTAPV-PAN2-R2 | R2 | CCGAATGCAGCTARCAGAGG | 10519-10538 |
| CTAPV-PAN2-F1 | F1 | GCCATGATGGAGGAAGTG | 10261-10278 |
| CTAPV-PAN2-R1 | R1 | GGGCAGRTTTGTGGATTCAG | 10397-10416 |
| CTAPV-PAN-FW | PAN-FW | GAAACAGCCATGCCAAAAAATGAG | 9889-9912 |
| CTAPV-PAN-REV | PAN-RV | AGTGGGTTCCAGGGGTAGATCAG | 10762-10784 |
| CTAPV-PANdeg-FW | PANdeg-FW | GAAACAGCCATGCCMAARAATGAG | 9889-9912 |
| CTAPV-PANdeg-REV | PANdeg-RV | AGTGGGTTCCAGGRGTAGATYAG | 10762-10784 |
| CTAPV-PAN2-F3 | F3 | GAGTACGGGGCAGACGTCAC | 161-180 |
| CTAPV-PAN2-R3 | R3 | CATCCGCCGGCACTCTATCAAGCAG | 318-342 |
| CTAPV-PAN2-F4 | F4 | ATGCATAATGCTTTGATTGG | 2-18 |
| CTAPV-PAN2-R4 | R4 | GTGACGTCTGCCCCGTACTC | 161-180 |

A preferred form of this embodiment relates to a virus according to the invention wherein the cDNA reverse-transcribed from the viral RNA genome reacts in a PCR reaction with a primer set as depicted in SEQ ID NO: 7 and 8 to give a PCR product of 156+/−10 base pairs and reacts in a PCR reaction with a primer set as depicted in SEQ ID NO: 9 and 10 to give a PCR product of 335+/−10 base pairs and reacts in a PCR reaction with a primer set as depicted in SEQ ID NO: 11 and 12 to give a PCR product of 896+/−10 base pairs and reacts in a PCR reaction with a primer set as depicted in SEQ ID NO: 13 and 14 to give a PCR product of 896+/−10 base pairs and reacts in a PCR reaction with a primer set as depicted in SEQ ID NO: 15 and 16 to give a PCR product of 182+/−10 base pairs and reacts in a PCR reaction with a primer set as depicted in SEQ ID NO: 17 and 18 to give a PCR product of 182+/−10 base pairs.

A more preferred form of this embodiment relates to a virus according to the invention wherein the virus has a viral genome comprising a gene encoding an $E^{rns}$, a gene encoding an E2 and a gene encoding E1, wherein the nucleotide sequence of the $E^{rns}$ gene has a level of identity of at least 80% to the nucleotide sequence as depicted in SEQ ID NO: 1 and the nucleotide sequence of the E2 gene has a level of identity of at least 80% to the nucleotide sequence as depicted in SEQ ID NO: 3 and the nucleotide sequence of the E2 gene has a level of identity of at least 80% to the nucleotide sequence as depicted in SEQ ID NO: 5 and wherein the cDNA of the viral genome reacts in a PCR reaction with a primer set as depicted in SEQ ID NO: 7 and 8 to give a PCR product of 156+/−10 base pairs and reacts in a PCR reaction with a primer set as depicted in SEQ ID NO: 9 and 10 to give a PCR product of 335+/−10 base pairs and reacts in a PCR reaction with a primer set as depicted in SEQ ID NO: 11 and 12 to give a PCR product of 896+/−10 base pairs and reacts in a PCR reaction with a primer set as depicted in SEQ ID NO: 13 and 14 to give a PCR product of 896+/−10 base pairs and reacts in a PCR reaction with a primer set as depicted in SEQ ID NO: 15 and 16 to give a PCR product of 182+/−10 base pairs and reacts in a PCR reaction with a primer set as depicted in SEQ ID NO: 17 and 18 to give a PCR product of 182+/−10 base pairs.

The virus according to the invention can be in a live, a live attenuated or an inactivated form.

As indicated above, the DNA sequences of the genes encoding the $E^{rns}$, the E2 and the E1 protein of the virus have now been characterized. The identification of these genes is highly useful, since they can now be used i.a. as a basis for DNA-vaccines, for use in the preparation of subunit vaccines on the basis of these proteins or for diagnostic purposes, as will extensively be explained below.

Thus, another embodiment of the present invention relates to a gene encoding an $E^{rns}$ protein characterized in that the nucleotide sequence of that gene has a level of identity of at least 80% to the nucleotide sequence of the $E^{rns}$ gene as depicted in SEQ ID NO: 1.

A preferred form of this embodiment relates to such a gene having a level of identity of at least 82%, more preferably 84%, 86%, 88%, 90%, 91%, 92%, 93%, 94%, 95%, 96%, 97%, 98%, 99% or even 100%, in that order of preference, to the nucleotide sequence of the $E^{rns}$ gene as depicted in SEQ ID NO: 1.

Again another embodiment of the present invention relates to a gene encoding an E2 protein characterized in that the nucleotide sequence of that gene has a level of identity of at least 80% to the nucleotide sequence of the E2 gene as depicted in SEQ ID NO: 3.

A preferred form of this embodiment relates to such a gene having a level of identity of at least 82%, more preferably 84%, 86%, 88%, 90%, 91%, 92%, 93%, 94%, 95%, 96%, 97%, 98%, 99% or even 100%, in that order of preference, to the nucleotide sequence of the E2 gene as depicted in SEQ ID NO: 3.

And again another embodiment of the present invention relates to a gene encoding an E1 protein characterized in that the nucleotide sequence of that gene has a level of identity of at least 80% to the nucleotide sequence of the E1 gene as depicted in SEQ ID NO: 5.

A preferred form of this embodiment relates to such a gene having a level of identity of at least 82%, more preferably 84%, 86%, 88%, 90%, 91%, 92%, 93%, 94%, 95%, 96%, 97%, 98%, 99% or even 100%, in that order of preference, to the nucleotide sequence of the E1 gene as depicted in SEQ ID NO: 5.

Still another embodiment of the present invention relates to an $E^{rns}$ protein characterized in that this $E^{rns}$ protein is encoded by an $E^{rns}$ gene according to the invention.

Such $E^{rns}$ proteins of the virus according to the invention are highly suitable because they are i.a. suitable for use in vaccines, more specifically in subunit vaccines, they can be used to raise antibodies and they make diagnostic tests possible, as explained below.

A preferred form of this embodiment relates to an $E^{rns}$ having the amino acid sequence as depicted in SEQ ID NO: 2.

Again another embodiment of the present invention relates to an E2 protein, characterized in that that E2 protein is encoded by an E2 gene according to the invention.

Such E2's of the virus according to the invention are highly suitable because they are i.a. suitable for use in vaccines, more specifically in subunit vaccines, they can be used to raise antibodies and they make diagnostic tests possible, as explained below.

A preferred form of this embodiment relates to an E2 protein having the amino acid sequence as depicted in SEQ ID NO: 4.

And again another embodiment of the present invention relates to an E1 protein, characterized in that that E1 protein is encoded by an E1 gene according to the invention.

Such E1 proteins of the virus according to the invention are highly suitable because they are i.a. suitable for use in vaccines, more specifically in pseudo-particles and vaccine comprising such pseudo-particles, as explained below.

A preferred form of this embodiment relates to an E1 protein having the amino acid sequence as depicted in SEQ ID NO: 6.

It is one of the merits of the present invention that it is now for the first time possible to follow the course of viral infection and to analyse the presence or absence of the novel virus in the various organs and body fluids of pigs suspected of being infected with the novel virus according to the invention.

It is described in the Examples section that many tissues and organs from pigs suffering from Group A-II congenital tremor could now be tested for the presence or absence and the amount of the novel virus.

It was found that serum, plasma, PBLs, heart, small and large intestine, brain, thoracic spinal cord, lumbar spinal cord, liver, inguinal lymph node, lung, gall bladder, bladder, kidney, tonsil and spleen isolated from pigs suffering from Group A-II congenital tremor contain the novel virus.

This helped to gain more insight in the development of the disease.

It is another merit of the present invention that it is now possible to infect healthy pigs with the novel virus and to examine the route of viral infection. It is described in the Examples how, with this aim, organ material from Group A-II congenital tremors-animals was isolated and purified. This material was subsequently injected in healthy post-weaning piglets to study replication of the virus in vivo following methods applied by Patterson (10-20% (w/v) homogenates injected via various routes of administration, oral, nasal, intramuscular, subcutaneous).

It is again another merit of the present invention that it is now possible to infect pregnant gilts with the novel virus with the aim of showing that the virus is capable of causing Group A-II congenital tremors in the piglets of these gilts. The results of these experiments are described in the Examples.

In addition this material has been used as challenge material in vaccination/challenge tests as described below.

It is also one of the merits of the present invention that, because the novel porcine pestivirus has now been isolated, the virus and/or protective subunits of the virus can be used as the starting material for vaccination purposes.

Merely as an example: the Examples section i.a. described the preparation of vaccines comprising baculo-expressed E2 protein, the administration of whole cell vaccines and purified E2-vaccines and a subsequent challenge with the virulent challenge material described above.

Thus, another embodiment of the present invention relates to vaccines for combating Group A-II CT in pigs, wherein such vaccines comprise an immunogenically effective amount of virus according to the invention and a pharmaceutically acceptable carrier.

Combating in this respect should be interpreted in a broad sense: combating Group A-II CT in pigs is considered to comprise vaccination in order to prevent the signs of the disease as well as vaccination to diminish the signs of the disease as outlined above.

Examples of pharmaceutically acceptable carriers that are suitable for use in a vaccine according to the invention are sterile water, saline, aqueous buffers such as PBS and the like. In addition a vaccine according to the invention may comprise other additives such as adjuvants, stabilizers, antioxidants and others, as described below.

A vaccine according to the invention may i.a. comprise the virus according to the invention in attenuated live or inactivated form.

Attenuated live virus vaccines, i.e. vaccines comprising the virus according to the invention in a live attenuated form, have the advantage over inactivated vaccines that they best mimic the natural way of infection. In addition, their replicating abilities allow vaccination with low amounts of viruses; their number will automatically increase until it reaches the trigger level of the immune system. From that moment on, the immune system will be triggered and will finally eliminate the viruses.

A live attenuated virus is a virus that has a decreased level of virulence when compared to virus isolated from the field. A virus having a decreased level of virulence is considered a virus that induces protection against Group A-II CT or at least diminishes the symptoms of CT, compared to the symptoms of CT caused by a wild-type pestivirus according to the invention.

Therefore, one preferred form of this embodiment of the invention relates to a vaccine comprising a virus according to the invention wherein said virus is in a live attenuated form.

Attenuated viruses can be obtained in various ways known in the art. They can e.g. be obtained by growing a virus according to the invention in the presence of a mutagenic agent, followed by selection of virus that shows a decrease in progeny level and/or in replication speed. Many such mutagenic agents are known in the art.

Another often used method is serial in vitro passage on a susceptible cell line. Viruses then get adapted to the cell line used for the serial passage, so that they behave attenuated when transferred to the natural host again as a vaccine.

Still another way of obtaining attenuated viruses is subjecting viruses to growth under temperatures deviating from the temperature of their natural habitat. Selection methods for temperature sensitive mutants (Ts-mutants) are well-known in the art. Such methods comprise growing viruses, usually in the presence of a mutagen, followed by growth at both a sub-optimal temperature and at the optimal temperature, titration of progeny virus on cell layers and visual selection of those plaques that grow slower at the optimal temperature. Such small plaques comprise slow-growing and thus desired live attenuated viruses.

An alternative way to obtain a live attenuated pestivirus according to the invention relates to the deliberate modification of the genome of the pestivirus. This approach has the advantage over classical attenuation techniques as described above, that the nature of the attenuation is known. For pestiviruses, many live attenuated virus strains of e.g. the pestiviruses Bovine Viral Diarrhea virus and Classical Swine Fever virus have been described from which e.g. the E2 gene, the $E^{rns}$ gene or the $N^{pro}$ gene is either deleted or modified.

Examples of live attenuated pestiviruses, more specifically the porcine pestivirus Classical Swine Fever virus (CSFV), having an $N^{pro}$-deletion are described i.a. in U.S. Pat. No. 7,572,455 and in Mayer, D. et al[19].

Examples of live attenuated pestiviruses, more specifically Classical Swine Fever virus, having both an $E^{rns}$-modification and an $N^{pro}$-deletion are described i.a. in U.S. Pat. No. 7,572,455.

Examples of live attenuated pestiviruses, more specifically Classical Swine Fever virus, having a modification in the E2-gene are i.a. described by Risatti, G. R. et al.[22] and by Risatti, G. R. et al.[23].

Pestiviral infections in general are a problem in many countries where pigs, ruminants or sheep are raised. At present, different approaches to deal with pestiviral infections in general are applied in the various countries where pestiviruses cause economic damage. Some countries use stamping-out methods to remove the virus, whereas other countries prefer a vaccination approach. The fact that these different approaches are used in parallel however causes problems. Merely as an example: e.g. porcine pestiviruses circulate in farmed pigs but also in wildlife animals such as wild boars, and these thus form a reservoir from which virus can spill into domestic animals. Animals that have been vaccinated with a classical vaccine cannot easily be discriminated from field-infected cattle, because in both cases antibodies against the virus will be present. Thus it is largely unknown if pestiviral antibody-positive animals are antibody-positive due to infection (in which case they may carry the virus) or due to vaccination. As a consequence, such animals will not be allowed to be transported to countries that have chosen a stamping-out approach for that pestivirus.

Since the novel pestivirus causing Group A-II CT has now been identified, the same may apply in the future for this novel pestivirus.

This problem can be solved through the use of so-called marker or DIVA vaccines (DIVA=Differentiating Infected from Vaccinated Animals). Such vaccines lack one or more of the immunogenic viral proteins or at least one of the immunogenic epitopes, as a result of which marker-vaccinated animals will not produce antibodies against all immunogenic viral proteins/epitopes. The differences in antibody-palette between vaccinated and infected animals can be demonstrated by diagnostic tests designed for this purpose. Such tests thus allow to distinguish vaccinated from infected animals.

Since the genes encoding the $E^{rns}$, the Npro, the E1 and the E2 protein of the novel pestivirus according to the invention are now known, the known marker vaccine techniques as described for e.g. the porcine pestivirus CSFV can now be applied on the new virus. Examples of live attenuated CSFV vaccines that also suitable as marker vaccines are e.g. described by Van Gennip, H. G. P. et al[7], Reimann, I. et al[8], Beer, M. et al[9], Wehrle, F. et al[10], by Dong, X. N. and Chen, Y. H.[11], and by de Smit, A. J. et al.[24]. In most cases chimeric viruses are reported in which the E2 or $E^{rns}$ gene was exchanged for the respective gene of a heterologous virus strain or another pestivirus.

A possible disadvantage of the use of live attenuated viruses however might be that inherently there is a certain level of virulence left. This is not a real disadvantage as long as the level of virulence is acceptable, i.e. as long as the vaccine at least prevents the pigs from dying. Of course, the lower the rest virulence of the live attenuated vaccine is, the less influence the vaccination has on weight gain during/after vaccination.

An alternative for the use of live attenuated viruses is the use of non-transmissible viruses. In such viruses an essential gene is deleted, and complemented in trans in a cell line that is used to grow the virus. As a consequence, the progeny virus is a virus that, although capable of infecting a host cell, cannot replicate in that host cell. Such a non-transmissible virus closely mimics the natural infection and at the same time the virus cannot spread. A vaccine comprising such a non-transmissible virus is very safe and in addition it is very suitable as a marker vaccine. Such vaccines have been described for e.g. the porcine pestivirus CSFV i.a. by Widjojoatmodjo, M. N. et al.[25], and by Van Gennip, H. G. et al.[26].

Inactivated vaccines are, in contrast to their live attenuated counterparts, inherently safe, because there is no rest virulence left. In spite of the fact that they usually comprise a somewhat higher dose of viruses compared to live attenuated vaccines, they may e.g. be the preferred form of vaccine in pigs that are suffering already from other diseases. Pigs that are kept under sub-optimal conditions, such as incomplete nutrition or sub-optimal housing would also benefit from inactivated vaccines.

Therefore, another preferred form of this embodiment relates to a vaccine comprising a virus according to the invention wherein said virus is in an inactivated form.

Such inactivated whole virus vaccines can be made for the novel porcine pestivirus according to the invention. As is the case for known porcine pestivirus vaccines, the production basically comprises the steps of growing the novel porcine pestivirus on susceptible porcine cells, harvesting the virus, inactivating the virus and mixing the inactivated virus with a pharmaceutically acceptable carrier.

The standard way of inactivation is a classical treatment with formaldehyde. Other methods well-known in the art for inactivation are UV-radiation, gamma-radiation, treatment with binary ethylene-imine, thimerosal and the like. The skilled person knows how to apply these methods. Preferably the virus is inactivated with β-propiolactone, glutaraldehyde, ethylene-imine or formaldehyde. It goes without saying that other ways of inactivating the virus are also embodied in the present invention.

As indicated above, a virus according to the invention can be grown in cell culture on susceptible porcine cells or cell lines.

Thus, another embodiment of the invention relates to a cell culture comprising a pestivirus according to the present invention. An example of such a cell line is SK6.

Although whole inactivated porcine pestiviruses according to the invention and non-transmissible porcine pestivirus viruses according to then invention provide a good basis for inactivated vaccines, their production may be expensive, depending i.a. upon the type of host cells used, the substrate and the cell culture medium used.

In the specific case of pestiviruses, an attractive alternative for the use of whole inactivated viruses or non-transmissible porcine pestivirus viruses according to the invention is the use of porcine pestivirus subunits, especially of $E^{rns}$ and E2 protein.

The expression of such subunits, especially of $E^{rns}$ and E2 protein is known in the art and is extensively described for the porcine pestivirus CSFV both in baculovirus expression systems and in mammalian cells, by Hulst, M. M. et al.[27], Bouma, A. et al.[28], Van Rijn, P. A. et al.[29], Moorman, R. J. M. et al.[30], Donofrio, G. et al.,[31], Lutticken D. et al.[32], and Floegel-Niesmann et al.[33].

High yield expression of $E^{rns}$ and E2 in baculovirus expression systems is e.g. described in EP1049788.

Furthermore, baculovirus expression systems and baculovirus expression vectors in general have been described extensively in textbooks such as by O'Reilly at al.[34] and Murhammer[35].

Baculovirus-based expression systems are also commercially available, e.g. from Invitrogen Corporation, 1600 Faraday Avenue, Carlsbad, Calif. 92008, USA.

An alternative for Baculovirus-based expression systems are yeast-based expression systems. Yeast expression systems are e.g. described by Gellissen et al.[36].

Donofrio, G. et al.,[31] describe the expression of BVDV E2 in a mammalian cell line.

Ready-to-use expression systems are i.a. commercially available from Research Corp. Technologies, 5210 East Williams Circle, Suite 240, Tucson, Ariz. 85711-4410 USA. Yeast and insect cell expression systems are also e.g. commercially available from Clontech Laboratories, Inc. 4030 Fabian Way, Palo Alto, Calif. 94303-4607, USA.

Expression of the $E^{rns}$ and E2 proteins in mammalian cell based expression systems as described by Donofrio, G. et al[31] although very suitable, would most likely be more expensive to use when compared to the baculovirus-based expression systems.

Thus another form of this embodiment relates to a vaccine for combating Group A-II CT in pigs, characterized in that said vaccine comprises an immunogenically effective amount of an $E^{rns}$ and/or E2 and/or E1 protein according to the invention and a pharmaceutically acceptable carrier.

More preferably, such subunits are in the form of so-called pestivirus pseudo-particles.

Such pseudo-particles are basically virus-like particles that comprise the $E^{rns}$, E1 and E2 proteins.

However they differ from the wild-type virus in that they do not comprise the whole pestiviral genome and therefore they are not capable of replicating in the host. As a consequence, pestivirus pseudo-particles do not have to be inactivated before use in a vaccine, and therefore they have the additional advantage that they are intrinsically safe.

Pestivirus pseudo-particles can be obtained by expression of the $E^{rns}$, E1 and E2 proteins in a suitable expression system. Examples of pestivirus pseudo-particles and how to produce such pseudo-particles are described i.a. in EP1454981 and EP1170367.

Thus again another embodiment relates to pseudo-particles characterized in that they comprise an $E^{rns}$ protein according to the invention, an E2 protein according to the invention and an E1 protein according to the invention.

The amount of pseudo-particles in a vaccine and the route of administration would be comparable with that of inactivated whole virus particles, since in terms of immunogenicity and similarity of the capsid they are comparable to inactivated whole virus particles.

Usually, an amount of between 1 and 100 μg of the novel porcine pestivirus pseudo-particles would be very suitable as a vaccine dose. From a point of view of costs, a preferred amount would be in the range of 1-50 μg of pseudo-particles, more preferred in the range of 1-25 μg.

A vaccine according to the invention, more specifically a vaccine on the basis of inactivated whole virus, subunits such as $E^{rns}$ and E2 protein or pseudo-particles, preferably comprises an adjuvant. Conventional adjuvants, well-known in the art are e.g. Freund's Complete and Incomplete adjuvant, vitamin E, non-ionic block polymers, muramyl dipeptides, Quill A®, mineral oil e.g. Bayol® or Markol®, vegetable oil, and Carbopol® (a homopolymer), or Diluvac® Forte. The vaccine may also comprise a so-called "vehicle". A vehicle is a compound to which the polypeptide adheres, without being covalently bound to it. Often used vehicle compounds are e.g. aluminum hydroxide, -phosphate or -oxide, silica, Kaolin, and Bentonite.

In principle it may suffice to administer a vaccine according to the invention just once. However, especially in the case of inactivated vaccines, be it whole virus vaccines, sub-unit vaccines or pseudo-particle vaccines, preferably also a first and possibly a second booster vaccination is given. A first booster would usually be given at least two weeks after the first vaccination. A very suitable moment for a booster vaccination is between 3 and 16 weeks after the first vaccination. A second booster, if necessary, would usually be given between 4 and 50 weeks after the first booster.

An alternative to the inactivated whole virus, subunits such as $E^{rns}$, E2 and E1 protein or pseudo-particles approach is the use of live recombinant vector viruses that have pigs as their host animal, as carriers of the novel porcine pestiviral $E^{rns}$, E2 or E1 gene.

Amongst the suitable recombinant vector viruses that have pigs as their host animal, several vector viruses are especially suitable as carriers: Pseudorabies virus (PRV), Porcine Adeno virus (PAV), Swine Pox virus (SPV) and Classical Swine Fever virus (CSFV). In addition, vaccinia virus has been described as a suitable vector virus.

The use of such recombinant vector viruses in vaccines has the additional advantage that the vaccinated animals become at the same time vaccinated against both the vector virus and the novel pestivirus according to the invention.

The use of Pseudorabies virus (PRV) as a live recombinant vector virus for the porcine pestivirus CSFV E2 gene is described by van Zijl et al.[38] and by Peeters et al.[39] for a replication defective PRV recombinant vector virus.

A live recombinant porcine adenovirus (PAV) vector virus as a vector virus for the porcine pestivirus CSFV E2 gene is described by Hammond et al.[40,41].

A live recombinant Swine Pox virus (SPV) vector virus as a vector virus for the porcine pestivirus CSFV E2 gene is described by Hahn et al.[42]

In addition, vaccinia virus has been described as a suitable vector virus by Ruemenapf et al.,[37] who describes the expression of all four structural proteins, and i.a. the induction of protective immunity in pigs vaccinated with vaccinia virus recombinant vectors expressing E2.

Live attenuated CSFV virus is also very suitable as live recombinant vector virus. Merely as an example; live attenuated CSFV from which the $N^{pro}$ gene has been deleted, has been described by Mayer et al.[19]Such a live attenuated virus allows, i.a. at the site of the deletion of the $N^{pro}$ gene, for the insertion of the gene encoding the $E^{rns}$ or E2 gene. Thus, such a live recombinant CSFV virus equally forms a very suitable vector virus for the novel porcine pestiviral $E^{rns}$ or E2 gene.

Very suitable amounts of such live recombinant vector virus would be in the range of $10^5$ $TCID_{50}$ to $5\times10^9$ $TCID_{50}$ of vector virus per vaccine dose, depending on the level of attenuation of the virus.

The expression of the novel porcine pestiviral $E^{rns}$, E2 or E1 gene can be brought under the control of any suitable heterologous promoter that is functional in a mammalian cell (see below). A heterologous promoter is a promoter that is not the promoter responsible for the transcription of the novel porcine pestiviral $E^{rns}$, E2 or E1 gene in the wild-type form of the novel porcine pestivirus according to the invention.

Therefore, another embodiment of the present invention relates to a DNA fragment comprising a gene encoding the novel porcine pestiviral $E^{rns}$, E2 or E1 gene according to the invention, characterized in that said gene is under the control of a functional heterologous promoter.

A promoter that is functional in a mammalian cell is a promoter that is capable of driving the transcription of a gene that is located downstream of the promoter in a mammalian cell.

Examples of suitable promoters that are functional in a mammalian cell include classic promoters such as the CAG promoter (Niwa, H. et al., Gene 108: 193-199 (1991), the (human) cytomegalovirus immediate early promoter (Seed, B. et al., Nature 329, 840-842, 1987; Fynan, E. F. et al., PNAS 90, 11478-11482, 1993; Ulmer, J. B. et al., Science 259, 1745-1748, 1993), Rous sarcoma virus LTR (RSV, Gorman, C. M. et al., PNAS 79, 6777-6781, 1982; Fynan et al., supra; Ulmer et al., supra), the MPSV LTR (Stacey et al., J. Virology 50, 725-732, 1984), SV40 immediate early promoter (Sprague J. et al., J. Virology 45, 773, 1983), the SV-40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2 and the β-actin promoter (Tang et al., Nature 356, 152-154, 1992). The regulatory sequences may also include terminator and poly-adenylation sequences. Amongst the sequences that can be used are the well-known bovine growth hormone poly-adenylation sequence, the SV40 poly-adenylation sequence, the human cytomegalovirus (hCMV) terminator and poly-adenylation sequences.

Thus the present invention also relates to a live recombinant vector virus comprising a DNA fragment comprising a gene encoding an $E^{rns}$ and/or E2 and/or E1 protein according to the invention under the control of a functional promoter.

Another form of the embodiment of the present invention that relates to vaccines, relates to a vaccine for combating Group A-II CT in pigs, characterized in that said vaccine comprises a live recombinant vector virus comprising a DNA fragment comprising a gene encoding an $E^{rns}$ and/or E2 and/or E1 protein according to the invention under the control of a functional promoter and a pharmaceutically acceptable carrier.

It goes without saying that the live recombinant vector virus should be expressing an immunogenically effective amount of the $E^{rns}$ and/or E2 and/or E1 and/or E.

An alternative for vaccination with an inactivated whole virus vaccine, a pseudo-particle vaccine or a live recombinant vector virus, is the use of DNA vaccination.

Such DNA vaccination is based upon the introduction of a DNA fragment carrying the gene encoding the $E^{rns}$, E2 or E1 protein under the control of a suitable promoter, into the host animal. Once the DNA is taken up by the host's cells, the gene encoding the $E^{rns}$, E2 or E1 protein is transcribed and the transcript is translated into $E^{rns}$, E2 or E1 protein in the host's cells. This closely mimics the natural infection process of the porcine pestivirus.

Suitable promoters are promoters that are functional in mammalian cells, as exemplified above.

A DNA fragment carrying the gene encoding the $E^{rns}$, E2 or E1 protein under the control of a suitable promoter could e.g. be a plasmid. This plasmid may be in a circular or linear form.

An example of successful DNA vaccination of pigs is the successful vaccination against Classical Swine Fever virus as described by Tian, D. Y. et al.[(45)], by Sun, Y. et al.[(46)], and by Sun, Y. et al.[(47)].

Other examples of successful DNA vaccination of pigs are i.a. the successful vaccination against Aujeszky's disease as described in Gerdts et al.[(43)] They describe a DNA vaccine wherein a DNA fragment is used that carries glycoprotein C under the control of the major immediate early promoter of human cytomegalovirus. Vaccination was done four times with two weeks intervals with an amount of 50 µg of DNA. Vaccinated animals developed serum antibodies that recognized the respective antigen in an immunoblot and that exhibited neutralizing activity.

Another example of successful DNA vaccination of pigs is given by Gorres et al.[(44)] They described successful DNA vaccination of pigs against both pandemic and classical swine H1N1 influenza. They vaccinated with a prime vaccination and 2 homologous boosts at 3 and 6 weeks post priming, of a DNA vaccine comprising the HA gene of influenza H1N1 under the control of a functional promoter.

Since the E2 protein of the novel pestivirus according to the invention is the most immunogenic protein, this is the preferred protein for use in DNA vaccines. Still, it may be necessary to use the methods described above ([(45)],[(46)],[(47)]) or to rely on additional measures as described in[(9)] in order to enhance the immunogenicity of the DNA vaccine.

Thus, again another form of this embodiment relates to a vaccine for combating Group A-II CT in pigs, characterized in that said vaccine comprises a DNA fragment comprising a gene encoding an $E^{rns}$, E2 or E1 protein according to the present invention under the control of a functional promoter, and a pharmaceutically acceptable carrier.

It goes without saying that the DNA fragment comprising a gene encoding an $E^{rns}$, E2 or E1 protein should be expressing an immunogenically effective amount of $E^{rns}$, E2 or E1 protein.

What constitutes an "immunogenically effective amount" for a vaccine according to the invention that is based upon a whole porcine pestivirus according to the invention, a pseudo-particle according to the invention, a live recombinant vector or a DNA vaccine according to the invention depends on the desired effect and on the target organism.

The term "immunogenically effective amount" as used herein relates to the amount of CTAPV, pseudo-particle, live recombinant vector or DNA vaccine that is necessary to induce an immune response in pigs to the extent that it decreases the pathological effects caused by infection with a wild-type Group A-II CT pestivirus, when compared to the pathological effects caused by infection with a wild-type Group A-II CT pestivirus in non-immunized pigs.

It is well within the capacity of the skilled person to determine whether a treatment is "immunogenically effective", for instance by administering an experimental challenge infection to vaccinated animals and next determining a target animal's clinical signs of disease, serological parameters or by measuring re-isolation of the pathogen, followed by comparison of these findings with those observed in field-infected pigs.

The amount of virus administered will depend on the route of administration, the presence of an adjuvant and the moment of administration. This is exemplified below and, in addition, the literature quoted above and below relating to vaccines for other pestivirus vaccines provides further guidance.

A preferred amount of a live vaccine comprising virus according to the invention is expressed for instance as Tissue Culture Infectious Dose (TCID50). For instance for a live virus a dose range between 10 and $10^9$ TCID50 per animal dose may advantageously be used, depending on the rest virulence of the virus.

Preferably a range between $10^2$ and $10^6$ TCID50 is used.

Many ways of administration can be applied, all known in the art. Vaccines according to the invention are preferably administered to the animal via injection (intramuscular or via the intraperitoneal route) or per os.

The protocol for the administration can be optimized in accordance with standard vaccination practice. In all cases, administration through an intradermal injector (IDAL) is a preferred way of administration.

If a vaccine comprises inactivated virus or pseudo-particles according to the invention, the dose would also be expressed as the number of virus particles to be administered. The dose would usually be somewhat higher when compared to the administration of live virus particles, because live virus particles replicate to a certain extent in the target animal, before they are removed by the immune system. For vaccines on the basis of inactivated virus, an amount of virus particles in the range of about $10^4$ to $10^9$ particles would usually be suitable, depending on the adjuvant used.

If a vaccine comprises subunits, e.g. an $E^{rns}$, E2 or E1 protein according to the invention, the dose could also be expressed in micrograms of protein. For vaccines on the basis of subunits, a suitable dose would usually be in the range between 5 and 500 micrograms of protein, again depending on the adjuvant used.

If a vaccine comprises a DNA fragment comprising a gene encoding an $E^{rns}$, E2 or E1 protein, the dose would be expressed in micrograms of DNA. For vaccines on the basis of subunits, a suitable dose would usually be in the range between 5 and 500 micrograms of DNA, i.a. depending on the efficiency of the expression plasmid used. In many cases an amount of between 20 and 50 micrograms of plasmid per animal would be sufficient for an effective vaccination.

A vaccine according to the invention may take any form that is suitable for administration in the context of pig farming, and that matches the desired route of application and desired effect. Preparation of a vaccine according to the invention is carried out by means conventional to the person skilled in the art of making pestiviral vaccines.

Oral routes are preferred when it comes to ease of administration of the vaccine.

For oral administration the vaccine is preferably mixed with a suitable carrier for oral administration i.e. cellulose, food or a metabolisable substance such as alpha-cellulose or different oils of vegetable or animal origin.

In practice, swine are vaccinated against a number of different pathogenic viruses or micro-organisms. Therefore it is highly attractive, both for practical and economic reasons, to combine a vaccine according to the invention for pigs with e.g. an additional immunogen of a virus or micro-organism pathogenic to pigs, or genetic information encoding an immunogen of said virus or micro-organism.

Thus, a preferred form of this embodiment relates to a vaccine according to the invention, wherein that vaccine comprises at least one other pig-pathogenic microorganism or pig-pathogenic virus and/or at least one other immunogenic component and/or genetic material encoding said other immunogenic component, of said pig-pathogenic microorganism or pig-pathogenic virus. An immunogen or immunogenic component is a compound that induces an immune response in an animal. It can e.g. be a whole virus or bacterium, or a protein or a sugar moiety of that virus or bacterium.

The most common pathogenic viruses and micro-organisms that are pathogenic for swine are *Brachyspira hyodysenteriae*, African Swine Fever virus, Nipah virus, Porcine Circovirus, Porcine Torque Teno virus, Pseudorabies virus, Porcine influenza virus, Porcine parvovirus, Porcine respiratory and Reproductive syndrome virus (PRRS), Porcine Epidemic Diarrhea virus (PEDV), Foot and Mouth disease virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae.*

Therefore, a more preferred form of the invention relates to a vaccine according to the invention, wherein the virus or micro-organism pathogenic to swine is selected from the group of *Brachyspira hyodysenteriae*, African Swine Fever virus, Nipah virus, Porcine Circovirus, Porcine Torque Teno virus, Pseudorabies virus, Porcine influenza virus, Porcine parvovirus, Porcine respiratory and Reproductive syndrome virus (PRRS), Porcine Epidemic Diarrhea virus (PEDV), Foot and Mouth disease virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae.*

Still another embodiment relates to a method for the preparation of a vaccine according to the invention wherein the method comprises the mixing of a virus according to the invention and/or an $E^{rns}$ protein according to the invention and/or an E2 protein according to the invention and/or an E1 protein according to the invention and/or a DNA fragment according to the invention and/or a DNA fragment according to the invention and/or a DNA fragment according to the invention and/or a live recombinant vector virus according to the invention and/or a pseudo-particle according to the invention, and a pharmaceutically acceptable carrier.

Again another embodiment of the present invention relates to a virus according to the invention and/or an $E^{rns}$ protein according to the invention and/or an E2 protein according to the invention and/or an E1 protein according to the invention and/or a DNA fragment according to the invention and/or a DNA fragment according to the invention and/or a DNA fragment according to the invention and/or a live recombinant vector virus according to the invention and/or a pseudo-particle according to the invention, for use in a vaccine for combating Group A-II CT in pigs.

As mentioned above, A-II CT is frequently found, which means that it is important to know if the novel pestivirus according to the invention is present on a farm or in a certain pig-population well before the first clinical signs become manifest. Thus, for efficient protection against disease, a quick and correct detection of the presence of the novel pestivirus according to the invention is important.

Therefore it is another objective of this invention to provide diagnostic tools suitable for the detection of novel pestivirus according to the invention.

These tools partially rely on the availability of antibodies against the virus. Such antibodies can e.g. be used in diagnostic tests for novel pestivirus according to the invention.

Antibodies or antiserum comprising antibodies against the novel pestivirus according to the invention can quickly and easily be obtained through vaccination of e.g. pigs, poultry or e.g. rabbits with the virus according to the invention followed, after about four weeks, by bleeding, centrifugation of the coagulated blood and decanting of the sera. Such methods are well-known in the art.

Other methods for the preparation of antibodies raised against the novel pestivirus according to the invention, which may be polyclonal, monospecific or monoclonal (or derivatives thereof) are also well-known in the art. If polyclonal antibodies are desired, techniques for producing and processing polyclonal sera are well-known in the art for decades, see e.g. Mayer and Walter[35].

Monoclonal antibodies, reactive against the virus according to the invention can be prepared by immunizing inbred mice by techniques also long known in the art, see e.g. Kohler and Milstein[36].

Thus, another embodiment of the present invention relates to antibodies or antisera that are reactive with a virus according to the invention.

A diagnostic test kit based upon the detection of CTAPV may e.g. comprise a standard ELISA test. In one example of such a test the walls of the wells of an ELISA plate are coated with antibodies directed against the virus. After incubation with the material to be tested, labeled antibodies reactive with the virus are added to the wells. If the material to be tested would indeed comprise the novel pestivirus according to the invention, this virus would bind to the antibodies coated to the wells of the ELISA. Labeled antibodies reactive with the virus that would subsequently be added to the wells would in turn bind to the virus and a color reaction would then reveal the presence of antigenic material of the virus.

Therefore, still another embodiment of the present invention relates to diagnostic test kits for the detection of Group A-II congenital tremor associated porcine pestivirus, that comprise antibodies reactive with a virus according to the invention or with antigenic material thereof. Antigenic material of the virus is to be interpreted in a broad sense. It can be e.g. the virus in a disintegrated form, or viral envelope material comprising viral outer membrane proteins. As long as the material of the virus reacts with antiserum raised against the virus, the material is considered to be antigenic material.

A diagnostic test kit based upon the detection in serum of antibodies reactive with Group A-II congenital tremor associated porcine pestivirus may also e.g. comprise a standard ELISA test. In such a test the walls of the wells of an ELISA plate can e.g. be coated with the virus according to the invention or antigenic material thereof. After incubation with the material to be tested, e.g. serum of an animal suspected from being infected with the novel pestivirus according to the invention, labeled antibodies reactive with the virus according to the invention are added to the wells. If anti-novel pestivirus according to the invention antibodies would be present in the tested serum, these antibodies will bind to the viruses coated to the wells of the ELISA. As a consequence the later added labeled antibodies reactive with the virus would not bind and no color reaction would be found. A lack of color reaction would thus reveal the presence of antibodies reactive with the virus according to the invention.

Therefore, still another embodiment of the present invention relates to diagnostic test kits for the detection of antibodies reactive with Group A-II congenital tremor associated porcine pestivirus that comprise the virus according to the invention or antigenic material thereof.

The design of the immunoassay may vary. For example, the immunoassay may be based upon competition or direct reaction. Furthermore, protocols may use solid supports or may use cellular material. The detection of the antibody-antigen complex may involve the use of labeled antibodies; the labels may be, for example, enzymes, fluorescent-, chemoluminescent-, radio-active- or dye molecules.

Suitable methods for the detection of antibodies reactive with a virus according to the present invention in the sample include, in addition to the ELISA mentioned above, immunofluorescence test (IFT) and Western blot analysis.

An alternative but quick and easy diagnostic test for diagnosing the presence or absence of a Group A-II congenital tremor associated porcine pestivirus is a PCR test as referred to above, comprising a PCR primer set specifically reactive with the genome of novel pestivirus according to the invention. Specific in this context means unique for e.g. the genome of novel pestivirus according to the invention, i.e. not with the genome of other pestiviruses.

It goes without saying, that more primers can be used than the primers identified above. The present invention provides for the first time the unique sequence of the genome of the novel pestivirus according to the invention. This allows the skilled person to select without any additional efforts, other selective primers. By simple computer-analysis of the genome of novel pestivirus according to the invention gene sequence provided by the present invention with the, known, genome of other pestiviruses, the skilled person is able to develop other specific PCR-primers for diagnostic tests for the detection of a novel pestivirus according to the invention and/or for distinguishing between an novel pestivirus according to the invention and other viral (porcine) pathogens.

PCR-primers that specifically react with the genome of novel pestivirus according to the invention are understood to be those primers that react only with the genome of novel pestivirus according to the invention and not with the genome of another (porcine) pathogenic virus, or group of (porcine) pathogenic viruses.

Thus, another embodiment relates to a diagnostic test kit for the detection of Group A-II congenital tremor associated porcine pestivirus, characterised in that said test kit comprises a PCR primer set that is specifically reactive with the genome of the novel pestivirus according to the invention.

A preferred form of this embodiment relates to a diagnostic test kit for the detection of Group A-II congenital tremor associated porcine pestivirus, wherein said test comprises the primer set as depicted in SEQ ID NO: 15-16.

A special form of a diagnostic test is provided by the qRT-PCR test described in more detail in Example 10. This test is very suitable for the quantification of the amount of virus present in various samples such as serum samples, sperm samples and tissue samples. Such tests allow, in addition to the detection of viral RNA, for a quick and reliable quantification of the number of RNA copies present in such samples.

In Example 10, it is described how RNA was isolated and subjected to RT-reactions, whereafter oligonucleotide primers were used to amplify the 5' UTR genome of the CTAPV genome. This part of the viral genome was chosen based on conserved nucleotide sequence between CTAPV variants 1-9 (based on alignment of the nucleotide sequences). The primer sequences used in Example 10 were as follows: CTAPV-PAN2-F3-B: CGTGCCCAAAGAGAAATCGG (SEQ ID NO: 35) and CTAPV-PAN2-R3-B (SEQ ID NO: 36): CCGGCACTCTATCAAGCAGT.

The skilled person would however realise that any part of the viral genome that shows a conserved nucleotide sequence between CTAPV variants can be used for the selection of suitable primers.

Example 10 shows how the qRT-PCR reaction according to the invention was successfully used for the detection of viral RNA in e.g. the sperm of boars.

In Example 11 it is shown, using this diagnostic technique, that CTAPV-free gilts can become infected with CTAPV through the sperm of CTAPV-infected boars.

LITERATURE

1) Maplesden, D. C. and G. C. Brown, Can J Comp Med Vet Sci, 2: 170-2 (1957).
2) Bolske, G., T. Kronevi, andN. O. Lindgren, Nord Vet Med, 30: 534-7 (1978).
3) White, M. www.nadis.org.uk/bulletins/congenital-tremor.aspx.
4) Ha, Y., K. Jung, and C. Chae, Vet Rec, 156: 383-4 (2005).
5) Stevenson, G. W., et al., J Vet Diagn Invest, 13: 57-62 (2001).
6) Kennedy, S., et al., Journal of Veterinary Diagnostic Investigation, 15: 151-156 (2003).
7) Van Gennip, H. G. P. et al (A)., Vaccine 19: 447-459 (2001)
8) Reimann, I. et al (B)., Virology 322: 143-157 (2004)
9) Beer, M. et al (C)., Vaccine 25: 5665-5670 (2007)
10) Wehrle, F. et al (D)., Journal of General Virology 88: 2247-2258 (2007)
11) Dong, X. N. and Chen, Y. H., Vaccine 25:205-230 (2007).
12) Moennig, V., G. Floegel-Niesmann, and I. Greiser-Wilke, The Veterinary Journal 165: 11-20 (2003).
13) Deregt, D. and K. G. Loewen, Can. Vet. J. 36: 371-8 (1995).
14) Viralzone-Expasy. Pestivirus. 2010 16 Apr. 2013; Available from: http://viralzone.expasy. org/all_by_species/39.html.

15) Lindenbach, B. D., H.-J. Thiel, and C. Rice, Flaviviridae: the viruses and their replication. Fields virology: 1101-1152 (2007).
16) Stark, R., et al., J. Virol., 67: 7088-95 (1993).
17) Rumenapf, T., et al., J. Virol., 72: 2544-2547 (1998).
18) Tratschin, J. D., et al., J. Virol., 72: 7681-7684 (1998).
19) Mayer, D., M. A. Hofmann, and J. D. Tratschin, Vaccine. 22: 317-328 (2004).
20) Heimann, M., et al., J. Virol. 80: 1915-21 (2006).
21) Schneider, R., et al., Science 261: 1169-1171 (1993).
22) Risatti, G. R. et al., Journ. of Virol. 79: 3787-3796 (2005).
23) Risatti, G. R. et al., Virology 364: 371-82 (2007).
24) de Smit, A. J. et al., Vaccine 19: 1467-1476 (2001).
25) Widjojoatmodjo, M. N. et al., J. Virol. 74: 2973-2980 (2000).
26) Van Gennip, H. G., Vaccine 20: 1544-56 (2002).
27) Hulst, M. M. et al., J. Virol. 67:54355442 (1993)
28) Bouma, A. et al., Vet. Microbiol. 66: 101-114 (1999)
29) Van Rijn, P. A. et al., Vaccine 17: 433-440 (1999)
30) Moorman, R. J. M. et al., Vet. Microbiol. 73: 209-219 (2000)
31) Donofrio, G. et al., Clinical And Vaccine Immunol. 13: 698-701 (2006)
32) Lutticken D. et al., Proc. of the OIE symposium on Classical Swine Fever, Birmingham UK, July 9-10, Summaries p. 17 (1998)
33) Floegel-Niesmann et al., Vet Microbiol. 96:367-384 (2003)
34) Baculovirus Expression Vectors, A Laboratory Manual. By David R. O'Reilly, Lois K. Miller, and Verne A. Luckow. Publisher: Oxford University Press, USA ISBN-10:0195091310 (Sep. 23, 1993), ISBN-13: 978-0195091311 (May 1994).
35) Baculovirus and Insect Cell Expression Protocols. In: *Methods in Molecular Biology*™, Volume 388 (2007). Editors: David W. Murhammer. ISBN: 978-1-58829-537-8 (Print) 978-1-59745-457-5 (Online)
36) Production of recombinant proteins: novel microbial and eukaryotic expression systems by Gerd Gellissen, ISBN: 3-527-31036-3
37) Ruemenapf, T. et al., J. Virol. 65: 589-597 (1991)
38) Van Zijl, M. et al., J. Virol. 65: 2761-2765 (1991)
39) Peeters, B. et al., J. Gen. Virol. 78: 3311-3315 (1997)
40) Hammond, J. M. et al., Vaccine 18: 1040-1050 (2000)
41) Hammond, J. M. et al., Archives of Virology 146: 1787-1793 (2001)
42) Hahn, J. et al., J. Virol Methods 93: 49-56 (2001)
43) Gerdts et al, Journal of General Virology 78: 2139-2146 (1997)
44) Gorres et al., Clinical Vaccine Immunology 18: 1987-1995 (2011)
45) Tian, D. Y. et al., Vaccine 30: 3587-3594 (2012)
46) Sun, Y. et al., Vaccine 29: 8364-8372 (2011)
47) Sun, Y. et al., Vet. Immunol. Immunopathol. 137: 20-27 (2010)
48) Done, J. T. et al., Br. Vet. Journ. 142:145-150 (1986)
49) Becher, P. et al., Journal of General Virology 78: 1357-1366 (1997)
50) Patterson, D. S. P. et al., J. of Neurochem. 26: 481-485 (1976)

LEGEND TO THE FIGURES

FIG. 1: Schematic overview of primers designed in the RNA polymerase gene (NS5B) of CTAPV, and PCR products.

Figure 2:
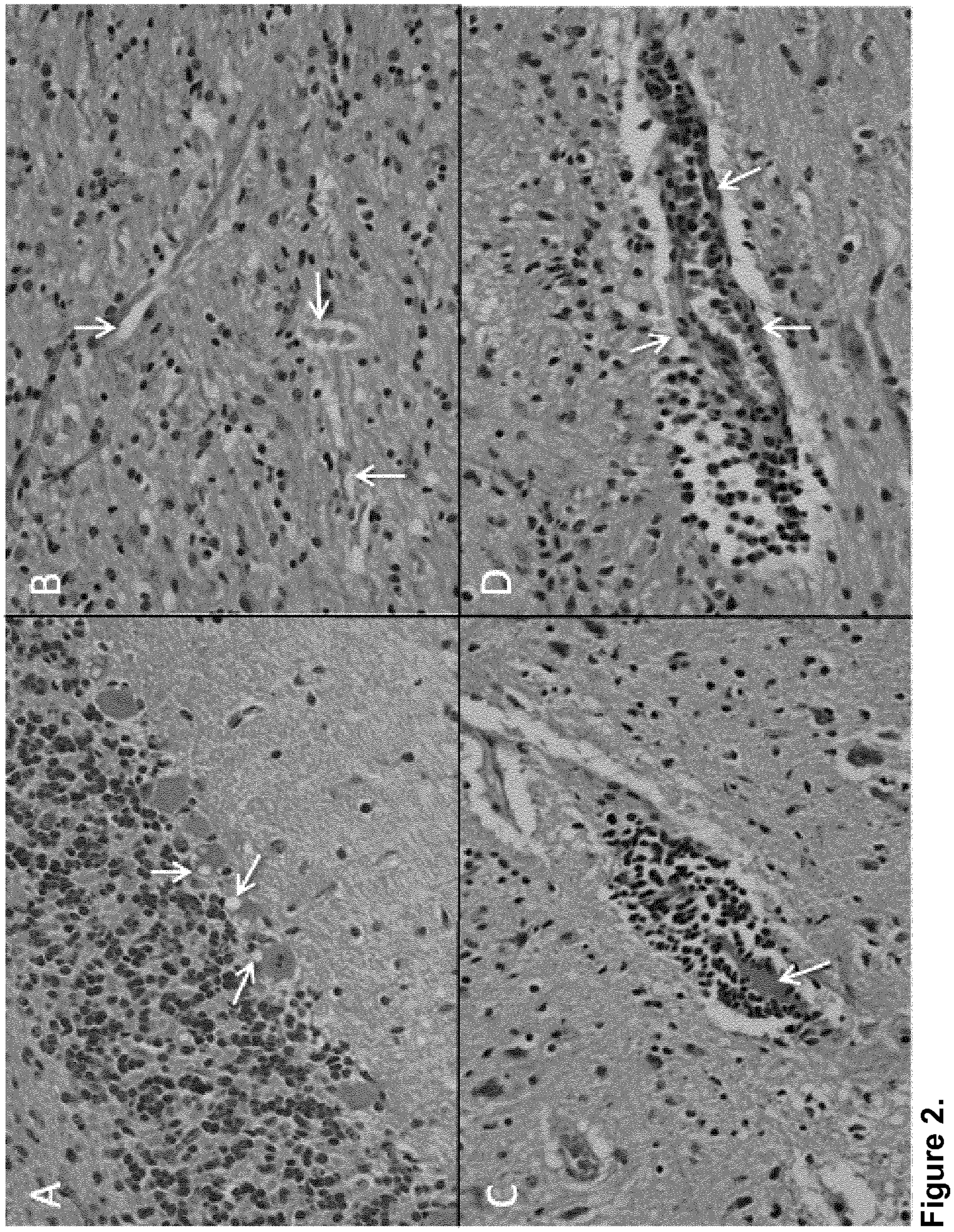

FIG. 2: Formalin fixed and hematoxyline-eosine stained 400× magnifications of the most distinct abnormalities in brain and spinal cord tissue. (A) Cross section of the cerebellum that shows vacuolisation of Purkinje cells (the layer of large cells between the granular layer and the white matter. White arrows show examples of vacuolization in some of the Purkinje cells. (B) Vacuolisation of the white matter, indicative for demyelination. Some examples of demyelination of axons in the spinal cord are indicated by white arrows. (C) Accumulation of microglia (stained dark purple) forming a microglial nodule around a degenerating neuron (neuronophagia) in the cerebrum. The neuron is indicated by the white arrow. (D) Perivascular cuffing in the thoracic spinal cord. Eosinophilic granulocytes are surrounding a blood vessel which is indicated by the arrows.

FIG. 3: Phylogenetic tree of CTAPV 1 and other previously identified pestiviruses of which the nucleotide sequence was deposited in Genbank (accession numbers indicated in the Figure). The amino acid sequences of the polyprotein were used for the nearest neighbor method. The bar in the left corner presents the average number of nucleotide substitution/site.

FIG. 4: Phylogenetic analysis of CTAPV variants. The amino acid sequences are used for the nearest neighbor method. The bar in the left corner presents the average number of nucleotide substitution/site. Analysis based on the first 5000 nucleotides of the genome. CTAPV type 7 not included. CTAPV 5 is identical to CTAPV 8.

FIG. 5: Amino acid sequence comparison of Erns-E1-E2 region of CTAPV 1 and 1B. The E2 protein sequence is in Italics. The Ems protein is underlined with a thick line, the E1 protein sequence is underlined with a thin line.

The subject sequence in FIG. 5 that is the thick underlined matches SEQ ID NO: 2. The subject sequence in FIG. 5 in italics matches SEQ ID NO: 4. The subject sequence in FIG. 5 that is thin underlined matches SEQ ID NO: 6.

Sequence ID NO: 21 is a partial genome sequence of CTAPV 1B (also called M1B in the application) in which includes the nucleotide sequences of Ems, E1 and E2. The Query amino acid sequence of FIG. 5 can be translated from this nucleotide sequence (nucleotides 1247-3190).

FIG. 6: Amino acid sequence comparison of Erns-E1-E2 region of CTAPV 1B and 8. The E2 protein sequence is in Italics. The Ems protein is underlined with a thick line, the E1 protein sequence is underlined with a thin line.

Sequence ID NO: 21 is a partial genome sequence of CTAPV_1B (also called M1B in the application) in which includes the nucleotide sequences of Ems, E1 and E2. The Query amino acid sequence of FIG. 6 can be translated from this nucleotide sequence (nucleotides 1247-3190).

Sequence ID NO:28 is a partial genome sequence of CTAPV_8 (also called M8 in the application) in which includes the nucleotide sequences of Ems, E1 and E2. The Subject amino acid sequence of FIG. 6 can be translated from this nucleotide sequence (nucleotides 1170-3113).

Figure 7:
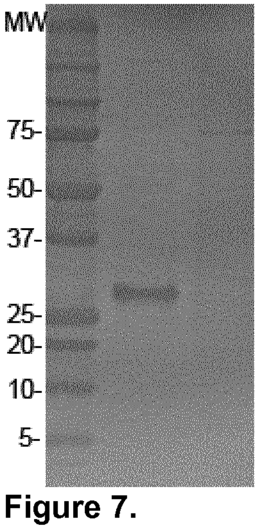

FIG. 7: Antibodies generated in rabbits specifically recognize the CTAPV E2 protein expressed in the baculovirus/SF9 expression system. Marker bands correspond (from bottom to top) to 5, 10, 20, 25, 37, 50, 75, 100, 150 and 250 kDa.

FIG. 8: Indication of the location of the Ems protein coding region (thick underlined), the E1 protein coding region (thin underlined) and the E2 protein coding region (in Italic). Sequence starts at nt 1259 of the reference genome. FIG. 8 is the Erns-E1-E2 nucleotide sequence and matches Seq ID: 19. The sequence in FIG. 8 that is thick underlined matches SEQ ID NO: 1. The sequence in FIG. 8 in italics matches SEQ ID NO: 3. The sequence in FIG. 8 that is thin underlined matches SEQ ID NO: 5.

Figure 9:
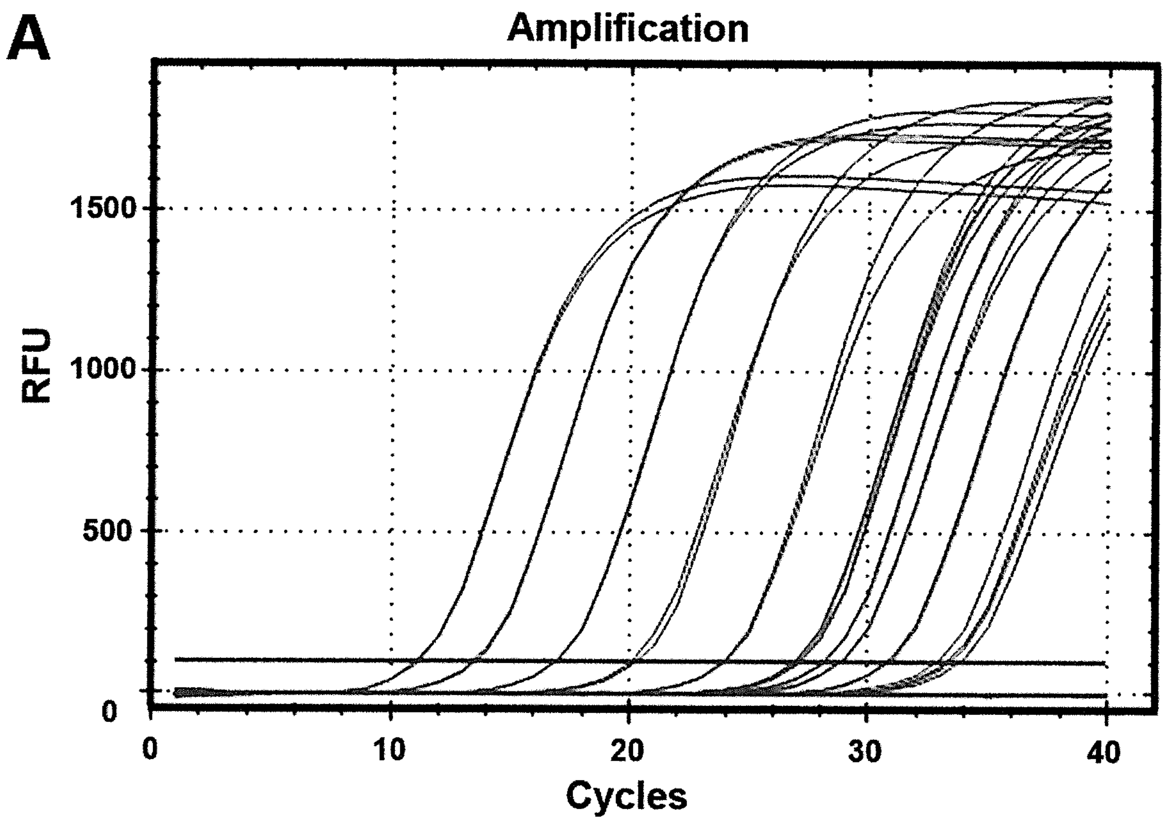
Figure 9:
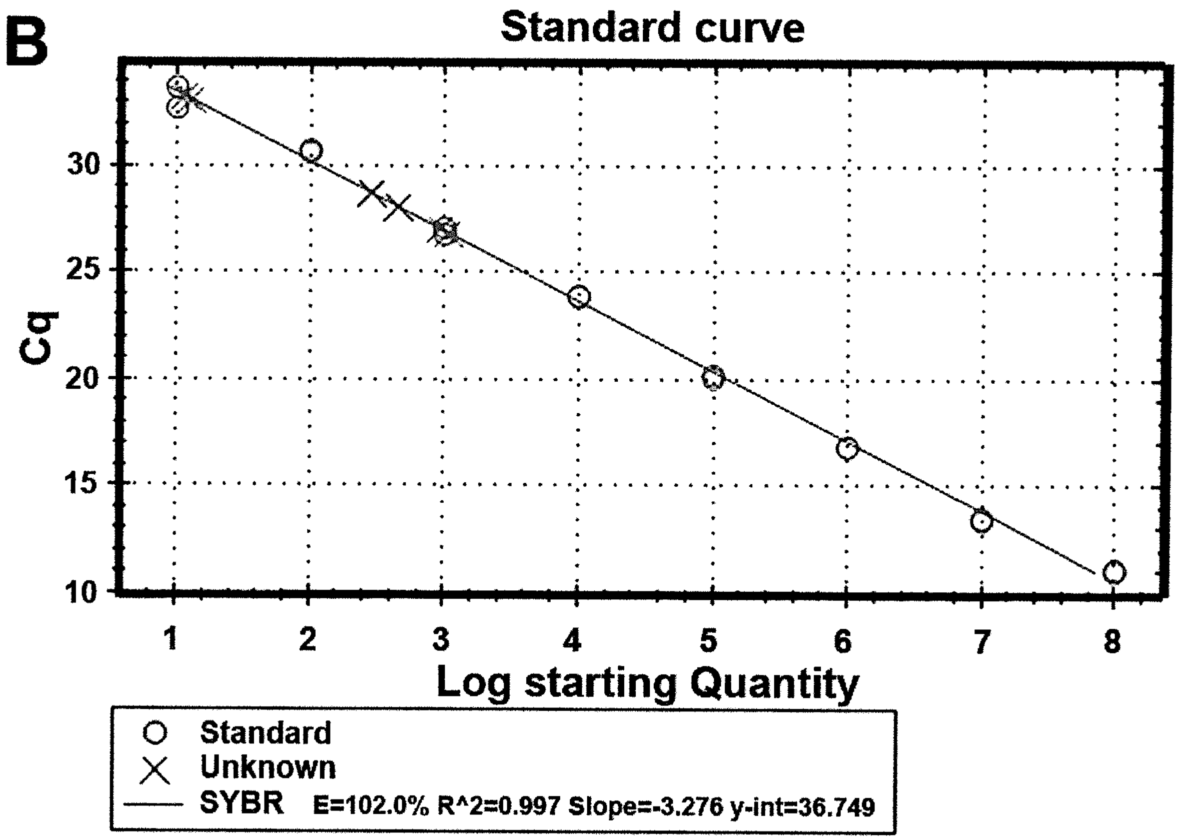
Figure 9:
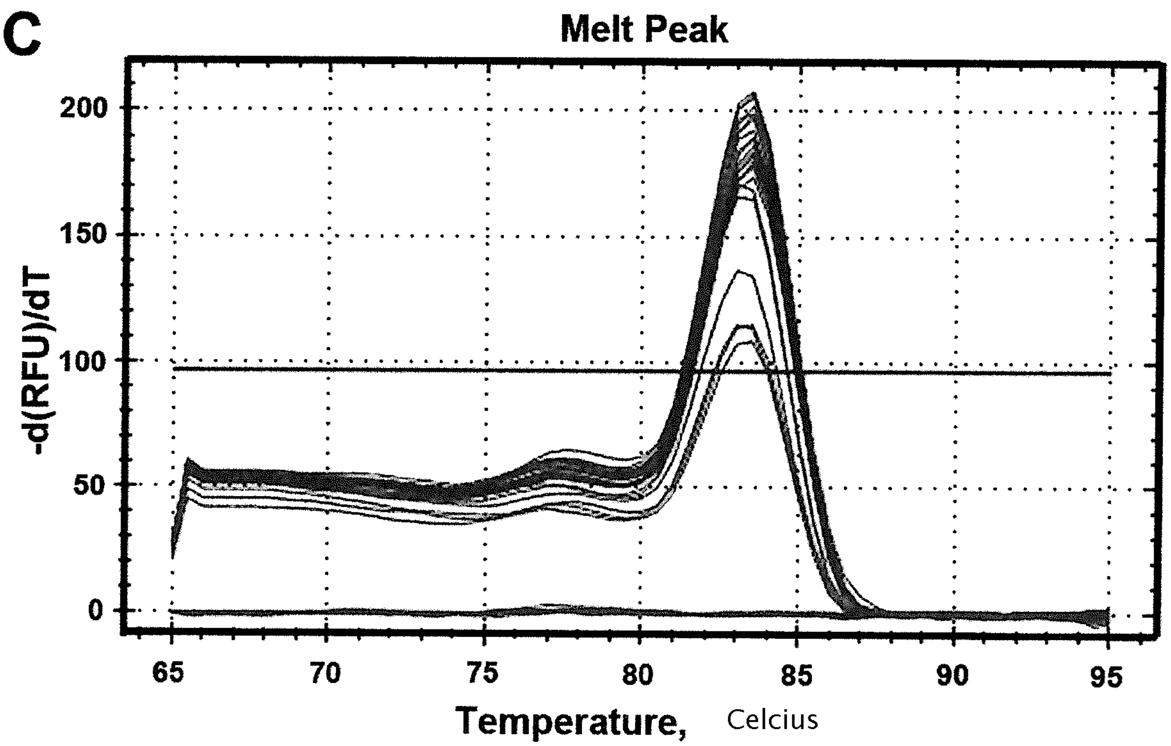

FIG. 9: RT-qPCR data of the standard line samples and the negative control sample. FIG. 9 A shows a diagram with Ct values with cycles plotted against RFU, FIG. 9 B shows the standard curve; Ct values plotted against log-transformed concentrations of serial ten-fold (log) dilutions of the target nucleic acid and FIG. 9 C shows the derivative melting curve in Real Time.

EXAMPLES

Example 1

Discovery of New Virus, CTAPV 1, on a Pig Farm in the Netherlands.

On a pig farm located in the Netherlands, an outbreak of congenital tremor type A-II was diagnosed in early 2012. Piglets born from gilt, first parity animals, were primarily affected but also higher parity sows were occasionally affected. Diagnosis was based on clinical observations and subsequent exclusion of congenital tremor types A-I, A-III, A-IV and A-V as the possible cause for disease. Clinically, affected piglets showed tremor in different grades, due to excessive muscle contractions during activity. The symptoms diminished when sleeping. Piglet loss was a secondary effect caused by the inability of affected animals to feed themselves, especially during the first week after birth. Histologically, the brain and the spinal cord were characterized by hypomyelinization. As further described below, not all affected pigs survived. In those that survived, the tremor diminished and finally disappeared as pigs grew older.

Based on the outbreak information, an infectious origin of the disease was suspected. In the first 20 weeks of the year 2012, a total of 48 μlitters with symptoms of congenital tremor were born from gilts, out of 231 litters born from gilts in total. This equals 21% of all litters born from gilts. At the peak of infection, 8 weeks after the initial outbreak, 85% of the gilt litters showed piglets with congenital tremor type A-II. The percentage piglet loss (piglet death) till weaning was 26% in affected litters, compared to 11% in non-affected litters. In affected litters, 60% of piglet death was attributable to congenital tremor. The total number of piglets born per litter was not affected. Congenital tremor affected both sexes, and prevalence within the litter varied between <10%-100%.

Prior to the outbreak in 2012, congenital tremor was observed in a few litters in November 2009 and December 2010.

Problems with outbreaks of congenital tremor have continued on this farm since 2012, and affected piglets were obtained in 2013 and 2014 (see below). However, the incidence rate decreased.

Blood plasma samples were obtained in March 2012 (6 samples, all piglets with symptoms of CT type A-II) and April 2012 (5 samples, all piglets with symptoms of CT type A-II). The new virus CTAPV 1 was detected in 11/11 samples.

More blood plasma samples were obtained from the same farm in July 2012. A total of 16 serum samples from piglets born from 2 sows and 1 gilt were analyzed. None of these piglets showed congenital tremor. CTAPV was found in 1/16 samples.

A new outbreak of the disease was diagnosed in January 2013. Four newborn pre-colostral piglets were obtained for necropsy, all showed CT type A-II. This virus was named CTAPV 1A because it originated from the same farm, but significant time had elapsed between the original outbreak and the occurrence of new clinical problems. The new virus CTAPV 1A was detected in 4/4 piglets.

A new outbreak of the disease was diagnosed in March 2013. Three newborn pre-colostral piglets were obtained for necropsy, all showed CT type A-II. This virus was named CTAPV 1B. The new virus CTAPV 1 was detected in 3/3 samples.

A new outbreak of the disease was diagnosed in January 2014. Four newborn pre-colostral piglets were obtained (rectal swabs), all showed CT type A-II. This virus was named CTAPV 1C. The new virus CTAPV 1 was detected in 4/4 samples. Necropsy on an additional 3 piglets was performed in February 2014, again all 3 piglets showed CT type A-II, and CTAPV was detected in 3/3 samples.

Post mortem examination was performed on piglets from outbreaks in January 2013, March 2013 and February 2014. Brains and spinal cord showed signs of demyelinization (see Example 2).

Seven piglets (6 pre-partus, last week of gestation; 1 newborn) from a farm with no history of congenital tremor type A-II were used as negative control for PCR and for post mortem examination. All plasma samples were negative for CTAPV virus, and no histological abnormalities were observed in these piglets.

Collection of Serum and Feces Samples

Feces and serum samples were obtained at farms in the Netherlands that have problems with CT type A-II in newborn pigs. Blood was collected in a tube (type: Vacuolette 8 ml Sep Clot Activator ref: 455071) and serum was isolated by centrifuging 20 minutes at 3000×g at 4° C. Feces were collected using a dry cotton-swab and put in a sterile tube containing 2 ml Phosphate-buffered saline solution (PBS). Then cotton swabs with feces were stirred strongly and discarded. Both serum and feces samples were stored at −70° C. until analysis.

Viral RNA Isolation with Optional DNAse Treatment

For viral RNA isolation, the QIAamp Viral RNA mini Kit (Qiagen) was used in combination with RNase free DNase kit (Qiagen).

In short, 1% solution of carrier-RNA/AVE in AVL buffer was prepared. 560 μl carrier-RNA/AVE in AVL was mixed with 140 μl sample and incubated 10 minutes at room temperature. Then 560 μl ethanol (>99%) was added and samples were transferred to a QIAamp mini spin column. Columns were centrifuged for 1 minute at 6000×g. Columns were washed by adding 250 μl AW1 and spinning the columns 30 seconds at 6000×g. DNase-mix was prepared by mixing 10 μL DNase with 70 μl RDD buffer per sample. 80 μl DNase-mix was incubated on the membrane during 15 minutes at room temperature. Washing was continued by putting 250 μl AW1 on the column and spinning it 30 seconds at 6000×g, followed by adding 500 μl AW2 to the columns and centrifuging 3 minutes at 13000×g. Collection tubes were replaced and columns were centrifuged for another minute. Spin columns were transferred into a 1.5 ml Eppendorf tube, where 65 μl AVE buffer was added on membranes and centrifuged 1 minute at 6000×g. The RNA samples were preceded to the Reverse Transcriptase-reaction immediately.

Reverse Transcriptase-Reaction

RNA was transcribed into cDNA using SuperScript® III First-Strand Synthesis System for RT-PCR (Invitrogen). The manufacturer's protocol was followed with some minor modifications. In summary, 1 μl random hexamers and 1 μl 10 mM dNTPs were mixed with 8 μl RNA. This was first incubated 5 minutes at 65° C., then chilled on ice. Then 10 μl cDNA synthesis mix, consisting of 2 μl 10×RT buffer, 4 μl $MgCL_2$, 2 μl DTT, 1 μl RNaseOUT and 1 μl Superscript®III RT, was added to the samples. The samples were first incubated 10 minutes at 25° C., then 50 minutes at 50° C., followed by 5 minutes at 85° C. and finally chilled on ice. 1 μl RNase H was added to the samples and this was incubated 20 minutes at 37° C. The obtained cDNA samples were stored at −20° C. until use.

PCR

A. Primer combination CTAPV-PAN2-F1R1, -F2R1, -F1R2, -F2R2, Table 1,2

Each PCR reaction contained 27 μl WFI, 1 μl Super Taq Plus 5 μl 10× Super Taq PCR buffer, 5 μl dNTPs, 5 μl forward primer and 5 μl reverse primer. Overview of used primers is depicted in Table 1. The PCR program used to detect CTAPV consisted of a 4 minute initialization-phase, at 95° C. This was followed by 35 cycles of sequentially denaturation for 30 seconds at 95° C., annealing for 30 seconds at the appropriate annealing temperature for the primer pair (see Table 1) and extension for 30 seconds at 72° C. A final extension at 72° C. was maintained for 10 minutes. All PCR products were analyzed with 1.5% agarose-gel electrophoresis. See FIG. 1.

B. Primer combination CTAPV-PAN-FW-RV, PANdeg-FW-PANdeg-REV, Table 1,2

Each PCR reaction contained 27 μl WFI, 1 μl Super Taq Plus 5 μl 10× Super Taq PCR buffer, 5 μl dNTPs, 5 μl forward primer and 5 μl reverse primer. Overview of used primers is depicted in Table 2. The PCR program used to detect CTAPV consisted of a 4 minute initialization-phase, at 95° C. This was followed by 40 cycles of sequentially denaturation for 30 seconds at 95° C., annealing for 30 seconds at the appropriate annealing temperature for the primer pair (see Table 2) and extension for 60 seconds at 72° C. A final extension at 72° C. was maintained for 10 minutes. All PCR products were analyzed with 1.5% agarose-gel electrophoresis.

C. Primer combination CTAPV-PAN2-F3R3, -F4R4, Table 1,2

Each PCR reaction contained 27 μl WFI, 1 μl Super Taq Plus 5 μl 10× Super Taq PCR buffer, 5 μl dNTPs, 5 μl forward primer and 5 μl reverse primer. Overview of used primers is depicted in Table 1. The PCR program used to detect CTAPV consisted of a 4 minute initialization-phase, at 95° C. This was followed by 35 cycles of sequentially denaturation for 30 seconds at 95° C., annealing for 30 seconds at the appropriate annealing temperature for the primer pair (see Table 1) and extension for 30 seconds at 72° C. A final extension at 72° C. was maintained for 10 minutes. All PCR products were analyzed with 1.5% agarose-gel electrophoresis.

TABLE 1

Overview of Primers

| Primer name | Short name | DNA Sequence | SEQ ID NO |
|---|---|---|---|
| CTAPV-PAN2-F2 | F2 | 5'-CGGATACAGAAATACTAC-3' | SEQ ID NO: 9 |
| CTAPV-PAN2-R2 | R2 | 5'-CCGAATGCAGCTARCAGAGG-3' | SEQ ID NO: 10 |
| CTAPV-PAN2-F1 | F1 | 5'-GCCATGATGGAGGAAGTG-3' | SEQ ID NO: 7 |
| CTAPV-PAN2-R1 | R1 | 5'-GGGCAGRTTTGTGGATTCAG-3' | SEQ ID NO: 8 |
| CTAPV-PAN-FW | PAN-FW | 5'-GAAACAGCCATGCCAAAAAATGAG-3' | SEQ ID NO: 11 |
| CTAPV-PAN-REV | PAN-RV | 5'-AGTGGGTTCCAGGGGTAGATCAG-3' | SEQ ID NO: 12 |
| CTAPV-PANdeg-FW | PANdeg-FW | 5'-GAAACAGCCATGCCMAARAATGAG-3' | SEQ ID NO: 13 |
| CTAPV-PANdeg-REV | PANdeg-RV | 5'-AGTGGGTTCCAGGRGTAGATYAG-3' | SEQ ID NO: 14 |
| CTAPV-PAN2-F3 | F3 | 5'-GAGTACGGGGCAGACGTCAC-3' | SEQ ID NO: 15 |
| CTAPV-PAN2-R3 | R3 | 5'-CATCCGCCGGCACTCTATCAAGCAG-3' | SEQ ID NO: 16 |
| CTAPV-PAN2-F4 | F4 | 5'-ATGCATAATGCTTTGATTGG-3' | SEQ ID NO: 17 |
| CTAPV-PAN2-R4 | R4 | 5'-GTGACGTCTGCCCCGTACTC-3' | SEQ ID NO: 18 |

TABLE 2

| Overview of primer combinations used, and characteristics of targets | | | |
|---|---|---|---|
| Primer combination | Anneal temperature (° C.) | PCR product size (bp) | Target |
| F1-R1 | 60.2 | 156 | NS5B |
| F1-R2 | 60.2 | 277 | NS5B |
| F2-R1 | 50.9 | 213 | NS5B |
| F2-R2 | 50.9 | 335 | NS5B |
| PAN-FW-PAN-RV | 58.0 | 896 | NS5B |
| PANdeg-FW-PANdeg-RV | 58.0 | 896 | NS5B |
| F3-R3 | 50.0 | 182 | 5'-UTR |
| F4-R4 | 50.0 | 182 | 5'-UTR |

D. SYBR Green Quantitative PCR

Standard Line for Quantification of qPCR Results

To obtain a standard for qPCR, a 155 bp PCR product of the CTAPV sequence containing the qPCR target sequence was cloned into a TOPO4 plasmid vector (Life Technologies) according to the manufacturer's instructions. The 155 bp CTAPV PCR product for cloning was obtained by performing a PCR with CTAPV-PAN2-F1 and CTAPV-PAN2-R1 primers, see Table 3. Subsequently, the PCR-product was electrophoresed on a 1.5% agarose-gel. The 155 bp band was cut out and DNA was extracted from the agarose-gel prior to cloning in the TOPO4 vector.

The TOPO TA Cloning Kit (Invitrogen) was used to ligate the PCR product into a pCR 4-TOPO4 vector and to transform this into One Shot TOP10 Chemically Competent *E. Coli*. In summary, 4 µl of DNA was mixed with 1 µl salt solution and 1 µl of TOPO vector. This ligation was incubated for 5 minutes at room temperature and then placed on ice. 2 µl ligation mix was added to One Shot® TOP10 Chemically Competent *E. Coli*. After 30 minutes incubation on ice, the mixture was heat shocked in a 42° C. water bath during 30 seconds and placed back on ice. Now 250 µl warm SOC medium was added and the mixture was incubated 1 hour at 37° C. in a shaking incubator, after which 100 µl mixture was spread out over an agar-LB+100 µg/ml ampicillin plate. The plate was incubated overnight in a 37° C. incubator.

Correctly cloned colonies were identified using colony-PCR using M13 Primers (see Table 3 below; (SEQ ID NO: 30 and 31)) in standard PCR assays, followed by gel electrophoresis. The correct colonies were grown in LBACF medium (MSD AH Media Production lot. No. 318781; Luria-Bertani medium, animal component free) with ampicillin, from which plasmid DNA was isolated using a QIAGEN® Plasmid Midi kit (Qiagen) according to manufacturer's protocol. To check for mutations, the plasmid DNA was sequenced using M13 primers.

TABLE 3

| Overview of primer combinations used for qPCR analysis | | | |
|---|---|---|---|
| Primer name | Primer DNA sequence | SEQ ID NO | Annealing Temperature |
| CTAPV-PAN2-F1 | 5'-GCCATGATGGAGGAAGTG-3' | SEQ ID NO: 7 | 60.0° C. |
| CTAPV-PAN2-R1 | 5'-GGGCAGRTTTGTGGATTCAG-3' | SEQ ID NO: 8 | 60.0° C. |
| M13 Fw | 5'-GTAAAACGACGGCCAG-3' | SEQ ID NO: 30 | 55.0° C. |
| M13 Rv | 5'-CAGGAAACAGCTATGAC-3' | SEQ ID NO: 31 | 55.0° C. |

Standard dilutions of the target sequence were calculated by measuring plasmid DNA concentrations of the vector. The formula for calculating plasmid copies/µl is depicted below (Formula 1). The DNA concentration (ng/µl) was measured using spectrophotometry. A, G, T and C are counts of the homonymous nucleotides in the plasmid. $6.02*10^{23}$ is the number of Avogadro. The multiplication by 2 converts ssDNA concentration into dsDNA concentration, and the multiplication by $10^9$ converts gram into nanogram. For qPCR reactions, eight dilutions were made containing $10^8$-$10^1$ copies/2 µl.

Formula 1: Formula for calculation of plasmid copies/µl $$\text{Plasmid copies/µl} = DNA\ \text{concentration}(ng/\text{µl}) \Big/ \left(\left(\frac{(A*328{,}24+G*344{,}24+T*303{,}22+C*304{,}16)}{(6{,}02*10\,\hat{}\,23)}\right)*2*10\,\hat{}\,9\right).$$

qPCR

A SYBR green based qPCR was developed. Each reaction contained 10 µl KAPA SYBR Fast qPCR master mix, 0.4 µl 10M forward primer, 0.4 µl 10M reverse primer, 7.2 µl WFI and 2 µl template. Primers CTAPV-PAN-F1 and CTAPV-PAN-R1 were used (See Table 4). The following program was used: 3 minutes at 95° C., followed by 39 cycles of sequentially 10 seconds at 95° C., 10 seconds at 60° C. and plate read in a Biorad CFX system. Results were analyzed using Biorad CFX software. Results were compared with a standard line as described above; a 10-fold dilution series of the 155 bp CTAPV product, cloned into a TOPO4 plasmid. A melting curve analysis between 65° C.→95° C.; per 0.5° C. 0.05 seconds was included in the qPCR program.

Specificity of the qPCR reaction was validated by gel electrophoresis of the amplified PCR product. The calibration curve slope and y-intercept were calculated by the CFX software. The $r^2$ was >0.99. The PCR efficiency calculated from the slope was between 95-105%.

TABLE 4 qPCR reaction mix

| | User solution | volume (µl)/reaction |
|---|---|---|
| KAPA SYBR Fast qPCR mastermix | 2× | 10 |
| CTAPV-PAN2-F1 | 10 µM | 0.4 |
| CTAPV-PAN2-R1 | 10 µM | 0.4 |
| WFI | n.a. | 7.2 |
| Template (cDNA) | n.a. | 2 |

Nucleotide Sequencing

Sanger sequencing was performed according to methods described in literature. Sequences were analyzed using Sequencer 5.0 and Clone Manager 9.

Phylogenetic Analysis

Phylogenetic analysis was performed to categorize CTAPV 1 as a pestivirus.

The amino acid sequences of the entire gene of the novel virus were used to make phylogenetic trees based on the Neighbor-Joining Maximum Likelyhood method, the Poisson correction model and bootstrap analysis (500 replicates).

These trees were made using the program MEGA, version 5, using standard settings. (MEGA5: Molecular Evolutionary Genetics Analysis Using Maximum Likelihood, Evolutionary Distance, and Maximum Parsimony Methods. Koichiro Tamura, Daniel Peterson, Nicholas Peterson, Glen Stecher, Masatoshi Nei and Sudhir Kumar. Mol. Biol. Evol. 28(10): 2731-2739. 2011 doi:10.1093/molbev/msr121 Advance Access publication May 4, 2011).

Example 2

Virus CTAPV can be Found in Organs and PBLs; Histology Indicative for Demyelination in Brain and Spinal Cord PCR analysis of the following organs of the necropsied pre-colostral new-born piglets (CTAPV 1A/1B, 2013) with congenital tremor type A-II indicated presence of CTAPV virus.

CTAPV could be detected in blood, serum, plasma, and PBLs (peripheral blood leukocytes), heart, small intestine, large intestine, brain, thoracic spinal cord, lumbar spinal cord, liver, inguinal lymph node, lung, gall bladder, bladder, kidney, tonsil and spleen. Highest quantities were detected in serum and tonsils.

The same organs were samples from pre-partus (last week of gestation) control piglets from a farm with no history of CT type A-II. All organs were negative in the PCR.

Brains and spinal cords of control and CTAPV-infected piglets were necropsied, formalin fixed and hematoxyline-eosine stained. Histological examination revealed indications for demyelination exclusively in CTAPV-infected piglets (FIG. 2 A-D).

CTAPV Variants from Farms at Different Geographical Locations.

CTAPV variants 2-9 were obtained from pig farms in the Netherlands from outbreaks in 2013 and onwards.

Table 5 shows the number of piglets tested on each farm, and the number of CTAPV PCR positive piglets (serum/rectal swabs).

TABLE 5

Overview of CTAPV variants from different farms in The Netherlands. Results of PCR analysis of CTAPV in serum and/or rectal samples.

| Variant | Farm | CTAPV pos. with symptoms | CTAPV neg. with symptoms | CTAPV pos. without symptoms | Total number of samples | Date |
|---|---|---|---|---|---|---|
| CTAPV 1 | 1 | 6 | 0 | 0 | 6 | 15-mrt-2012 |
| CTAPV 1 | 1 | 5 | 0 | 0 | 5 | 5-apr-2012 |
| CTAPV 1 | 1 | 0 | 0 | 1 | 15 | 20-jul-2012 |
| CTAPV 1A | 1 | 4 | 0 | 0 | 4 | 28-jan-2013 |
| CTAPV 1B | 1 | 3 | 0 | 0 | 3 | 5-mrt-2013 |
| CTAPV 1C | 1 | 4 | 0 | 0 | 4 | 31-jan-2014 |
| CTAPV 1C | 1 | 3 | 0 | 0 | 3 | 12-feb-2014 |

TABLE 5-continued

Overview of CTAPV variants from different farms in The Netherlands. Results of PCR analysis of CTAPV in serum and/or rectal samples.

| Variant | Farm | CTAPV pos. with symptoms | CTAPV neg. with symptoms | CTAPV pos. without symptoms | Total number of samples | Date |
|---|---|---|---|---|---|---|
| CTAPV 2 | 2 | 8 | 0 | 0 | 8 | 14-aug-2013 |
| CTAPV 3 | 3 | 8 | 0 | 0 | 8 | 11-okt-2013 |
| CTAPV 4 | 3 | 0 | 0 | 4 | 8 | 11-okt-2013 |
| CTAPV 5 | 4 | 5 | 0 | 0 | 5 | 31-mei-2013 |
| CTAPV 6 | 5 | 10 | 0 | 0 | 10 | 4-dec-2013 |
| CTAPV 7 | 6 | 15 | 0 | 0 | 15 | 8-jan-2014 |
| CTAPV 7 | 6 | 4 | 0 | 0 | 4 | 24-jan-2014 |
| CTAPV 8 | 7 | 4 | 0 | 0 | 4 | 6-mrt-2014 |
| CTAPV 9 | 8 | 4 | 0 | 0 | 4 | 12-feb-2014 |
| NEG. CONT. | 9 | 0 | 0 | 0 | 1 | 5-mrt-2013 |
| NEG. CONT. | 9 | 0 | 0 | 0 | 6 | 18-dec-2014 |
| TOTAL | | 83 | 0 | 5 | 113 | |

The disease association is 100% for piglets showing CT type A-II. CTAPV virus was detected in all piglets with congenital tremor type II, and not in control samples taken on a farm with no history of CT type A-II.

CTAPV 1 was found in one piglet that did not show congenital tremor. This piglet originated from Farm 1, a farm with history of CT type A-II.

CTAPV 4 was found in piglets that did not show congenital tremor. CTAPV 4 was found at the same farm where CTAPV 3 was found (Farm 3). Thus, CTAPV 4 was present on a farm with history of CT type A-II.

A total of 12 variants from 8 geographical different locations were found.

Variants CTAPV 1, 1A, 1B, 1C originate from the same farm at different points in time.

Variants CTAPV 3 and 4 originate from the same farm

Although found at different geographical locations, Variants CTAPV 5 and 8 are identical at the nucleotide level Table 6 shows reactivity of primer pairs.

TABLE 6

Reactivity of primer pairs.

| Variant | F1R1 | F1R2 | F2R1 | F2R2 | F3R3 | F4R4 | PAN-FW - PAN-RV | PANdeg-FW - PANdeg-RV |
|---|---|---|---|---|---|---|---|---|
| CTAPV 1 | + | + | + | + | + | + | + | + |
| CTAPV 1A | + | + | + | + | + | + | + | + |
| CTAPV 1B | + | + | + | + | + | + | + | − |
| CTAPV 1C | + | na | na | na | + | + | − | − |
| CTAPV2 | + | + | + | + | + | na | + | na |
| CTAPV 3 | − | − | + | + | + | na | na | na |
| CTAPV 4 | na | na | na | na | + | na | na | na |
| CTAPV 5 | + | + | + | + | + | na | + | na |
| CTAPV 6 | + | + | + | + | + | na | na | na |
| CTAPV 7 | + | na | na | + | + | + | + | + |
| CTAPV 8 | + | na | na | + | + | + | + | + |
| CTAPV 9 | na | na | na | na | + | na | na | na |

All variants can be detected using PCR primer pair F3R3

All variants can be detected using one of the PCR primer combinations F1R1, F1R2, F2R1, F2R2, however, Variant CTAPV 9 was not tested.

Genome Sequencing

The complete genome sequence of CTAPV 1 was obtained by Sanger sequencing.

Of other variants, CTAPV 1A, 1B, 1C, 2, 3, 4, 6, 8 and 9, the first 5000 bp including the coding sequences for $E^{rns}$, E1 and E2 were obtained.

Only a limited nucleotide sequence of 1073 nt is available for M7

Based on genome sequencing, it was concluded that CTAPV 5=CTAPV 8

Example 3

Phylogenetic Analysis of CTAPV and CTAPV Variants

The phylogenetic tree of the CTAPV 1 and other known pestiviruses is presented in FIG. 3. The percentage bootstrap support is specified at the nodes. Distance bars indicate the number of nucleotide substitutions per site.

The phylogenetic tree of 10 of the CTAPV variants described in this patent application is presented in FIG. 4. Only variants CTAPV 1, 1A, 1B, 1C, 2, 3, 4, 6, 8 and 9 were included in this analysis. The nucleotide sequence 1-5000 bp were included in this analysis, which includes the coding sequences for $E^{rns}$, E1 and E2.

CTAPV 7 was not included because only 1073 nt are available for M7.

CTAPV 5 is not included, because CTAPV 5=CTAPV 8

Example 4

Analysis of the Predicted E2 Protein/Nucleotide Sequence Shows that CTAPV 1B E2 Protein=CTAPV 1 E2 Protein. CTAPV 8 Protein Shows 14 Amino Acid Substitutions Compared to CTAPV 1.

Necropsied organs that could serve as starting material for infection experiments were available for CTAPV 1B, but not for CTAPV 1. We analyzed the nucleotide and amino acid sequence of the $E^{rns}$-E1-E2 genes/proteins of CTAPV 1 and 1B. The amino acid sequence is 100% identical (FIG. 5). The E2 protein sequence is in Italic. The $E^{rns}$ protein is underlined with a thick line, the E1 protein sequence is underlined with a thin line.

Necropsied organs that could serve as starting material for infection experiments were also available for CTAPV 8. We analyzed the nucleotide and amino acid sequence of the $E^{rns}$-E1-2 genes/proteins of CTAPV 1B and 8 (amino acid comparison in FIG. 6). The amino acid sequence is 95% identical. The E2 protein sequence is in Italic. The $E^{rns}$ protein is underlined with a thick line, the E1 protein sequence is underlined with a thin line. CTAPV 8 has 14 amino acid substitutions (93.3% identity) compared to CTAPV 1B, of which 9 are positives (positives 97.6%).

Example 5

Preparation of Challenge Material

Challenge material was obtained from necropsied organs (field material) of piglets affected by CTAPV 1B (2013) and CTAPV 8 (2014). Necropsied organs were stored at −70° C. until use.

CTAPV 1B

Brains of 3 piglets of the affected litter were pooled prior to homogenization.

Spinal cord of 3 piglets of the affected litter were pooled prior to homogenization Spleens of 3 piglets of the affected litter were pooled prior to homogenization Tonsils of 3 piglets of the affected litter were pooled prior to homogenization

CTAPV 8

Brains of 4 piglets of the affected litter were pooled prior to homogenization

Spinal cord of 4 piglets of the affected litter were pooled prior to homogenization Spleens of 4 piglets of the affected litter were pooled prior to homogenization Tonsils of 4 piglets of the affected litter were pooled prior to homogenization Pooled tissues were weighted after thawing. Subsequently, 9 times tissue-weight PBS (CTAPV 1B) or M6B8 medium with 1 μM HEPES (Sigma H3375-250G, CTAPV 8) was added to the tissue material. The tissue was homogenized using a blender, followed by shaking with small glass beads for 5 minutes. During homogenizing organ-pulp was kept on ice. The organ-pulp was centrifuged 1 hour at 3200×g. Supernatant was first passed over a 0.45 μm filter, and subsequently over a 0.22 μm filter. The filtered homogenate was stored at −70° C. until use.

Example 6

Infection Experiment in Weaner Aged Piglets to Obtain Infectious Material:

Challenge experiments with CTAPV 1B and CTAPV 8 organ homogenates originating from field isolates were conducted in 4 to 8 week old weaning-aged SPF/high health piglets of a commercial finisher pig breed.

At the time of placing in the test facility, CPDA (citrate phosphate dextrose adenine) blood samples, rectal swabs, oropharynx swabs and nasal swabs were obtained from the animals. Animals were housed in two separate experiment rooms: group A 8 animals and group B 8 animals. There was no physical contact or indirect contact via animal caretakers between the rooms.

In group A, six pigs were inoculated with CTAPV 1B homogenates via the intramuscular (IM), subcutaneous (SC), intranasal (N) and oral (OR) routes.

Two pigs received inoculum from mixed spleen+spinal cord+brain homogenate

Two pigs received inoculum from mixed spleen+tonsil+brain homogenate

Two pigs received inoculum from mixed brain+spinal cord homogenate

Two pigs served as contact sentinels

IM, SC and N volumes were 1.0 ml per dose, left and right. OR volume was 4 ml. Nasal dose was sprayed. Challenge doses are given in Table 7.

After inoculation, all pigs were observed daily for clinical signs, but the animals remained asymptomatic during the course of the experiment.

CPDA-blood, nose swabs, oropharynx swabs and rectal swabs were taken on day 0, day 3, day 7, day 10 and day 14 after inoculation to monitor infection and excretion of CTAPV 1B via qPCR analysis. Plasma was obtained from CPDA blood using the Leucosep® kit (Greiner Mat. no. 163 288). The results of qPCR analysis on plasma samples are presented in Table 7.

All inoculated animals showed a positive CTAPV qPCR result in blood plasma at day 10. Based on excretion of virus, animals were sacrificed at different time points to obtain fresh infectious material for subsequent in vitro and in vivo studies.

At the time of necropsy, brain, spinal cord, spleen, tonsils, and blood were taken from the animals.

TABLE 7

Challenge doses and Results challenge CTAPV 1B
CTAPV 1B:

| Animal | Challenge Material | Challenge Route | | challenge load RNA copies/ml in 10% homogenate | T = 0 Plasma RNA copies/ml | T = 3 d p chall Plasma RNA copies/ml | T = 7 d p chall Plasma RNA copies/ml | T = 10 d p chall Plasma RNA copies/ml | T = 14 d p chall Plasma RNA copies/ml |
|---|---|---|---|---|---|---|---|---|---|
| 326 | | sentinels | | | n.d. | n.d. | n.d. | n.d. | n.d. |
| 365 | | | | | n.d. | n.d. | n.d. | n.d. | n.d. |
| 366 | spleen + | IM, | 4 ml oral; | 6.15E+05 | n.d. | n.d. | n.d. | 2.38E+05 | N/A |
| 367 | spinal | nasal | 2 x 1 ml IM | | n.d. | n.d. | n.d. | 3.24E+04 | 2.00E+06 |
| | c + brain | oral + | 2 x 1 ml nasal; | | | | | | |
| | | SC | 2 x 1 ml SC | | | | | | |
| 368 | spleen + | IM, | 4 ml oraal; | 8.65E+05 | n.d. | n.d. | n.d. | 3.50E+05 | N/A |
| 369 | tonsil + brain | nasal | 2 x 1 ml IM | | n.d. | n.d. | n.d. | 2.16E+05 | 2.67E+06 |
| | | oral + | 2 x 1 ml nasal; | | | | | | |
| | | SC | 2 x 1 ml SC | | | | | | |
| 370 | brain + | IM, | 4 ml oral; | 3.91E+05 | n.d. | n.d. | n.d. | 3.24E+05 | 3.31E+06 |
| 371 | spinal cord | nasal | 2 x 1 ml IM | | n.d. | n.d. | 4.06E+04 | 5.23E+05 | N/A |
| | | oral + | 2 x 1 ml nasal; | | | | | | |
| | | SC | 2 x 1 ml SC | | | | | | |

n.d.: not detectable
N/A: not analysed (animal already sacrificed)

In group B, six pigs were inoculated with CTAPV 8 homogenates via the intramuscular (IM), subcutaneous (SC), Intranasal (N) and oral (OR) routes.

Two pigs received inoculum from spleen+tonsil+brain+spinal cord homogenate

Two pigs received inoculum from spleen+tonsil homogenate

Two pigs received inoculum from brain+spinal cord homogenate

Two pigs served as contact sentinels.

IM, SC and N volumes were 2.0 ml per dose, left and right. OR volume was 3 or 4 ml. Nasal dose was sprayed. Challenge doses are given in Table 8.

After inoculation, all pigs were observed daily for clinical signs, but the animals remained asymptomatic during the course of the experiment.

CPDA-blood, nose swabs, oropharynx swabs and rectal swabs were taken on day 0, day 3, day 7 and day 14 after inoculation to monitor infection and excretion of CTAPV-8 via qPCR analysis. Plasma was obtained from CPDA blood using the Leucosep® kit (Greiner Mat. no. 163 288). The results of qPCR analysis on plasma samples are presented in Table 8.

All inoculated animals showed a positive CTAPV qPCR result in blood plasma at day 3 and/or day 7. Based on excretion of virus, animals were sacrificed at different time points to obtain fresh infectious material for subsequent in vitro and in vivo studies.

At the time of necropsy, brain, spinal cord, spleen, tonsils, and blood were taken from the animals.

The organ materials were used as challenge material in the vaccination-challenge study as described in Example 8/9

TABLE 8

Challenge doses and Results challenge CTAPV 8
CTAPV 8:

| Animal | Challenge Material | Challenge Route | | challenge load RNA copies/ml in 10% homogenate | T = 0 Plasma RNA copies/ml | T = 3 d p chall Plasma RNA copies/ml | T = 7 d p chall Plasma RNA copies/ml | T = 14 d p chall Plasma RNA copies/ml |
|---|---|---|---|---|---|---|---|---|
| 394 | | sentinels | | | n.d. | n.d. | n.d. | n.d. |
| 395 | | | | | n.d. | n.d. | n.d. | n.d. |
| 397 | mix 4 | IM, | 3 ml oral; | 1.04E+06 | n.d. | 5.50E+03 | 2.55E+06 | N/A |
| 398 | organs | nasal | 2 x 2 ml IM | | n.d. | 5.22E+03 | 8.35E+04 | N/A |
| | | oral + | 2 x 2 ml nasal; | | | | | |
| | | SC | 2 x 2 ml SC | | | | | |
| 399 | spleen + | IM, | 4 ml oral; | 1.03E+06 | n.d. | 7.92E+03 | N/A | N/A |
| 400 | tonsil | nasal | 2 x 2 ml IM | | n.d. | 2.46E+03 | 1.57E+05 | N/A |
| | | oral + | 2 x 2 ml nasal; | | | | | |
| | | SC | 2 x 2 ml SC | | | | | |

TABLE 8-continued

Challenge doses and Results challenge CTAPV 8 CTAPV 8:

| Animal | Challenge Material | Challenge Route | | challenge load RNA copies/ml in 10% homogenate | T = 0 Plasma RNA copies/ml | T = 3 d p chall Plasma RNA copies/ml | T = 7 d p chall Plasma RNA copies/ml | T = 14 d p chall Plasma RNA copies/ml |
|---|---|---|---|---|---|---|---|---|
| 401 | brain + spinal cord | IM, nasal oral + SC | 4 ml oral; 2 x 2 ml IM 2 x 2 ml nasal; 2 x 2 ml SC | 4.02E+05 | n.d. | 3.28E+03 | 1.73E+04 | N/A |
| 402 | | | | | n.d. | 5.07E+03 | 4.77E+06 | N/A |

n.d.: not detectable

N/A: not analysed (animal already sacrificed)

Example 7

Preparation of Challenge Material for Vaccination-Challenge Experiment

Challenge material was obtained from Example 6.

CTAPV 1B

Brains, spinal cord, spleen and tonsils of 1 necropsied animal of example 6, group A

CTAPV 8

Brains, spinal cord, spleen and tonsils of 1 necropsied animal of example 6, group B Pooled tissues were weighted after thawing. Subsequently, 9 times tissue-weight M6B8 medium with 10 μM HEPES (Sigma H3375-250G) was added to the tissue material. The tissue was homogenized using a blender, followed by shaking with small glass beads for 5 minutes. During homogenizing organ-pulp was kept on ice. The organ-pulp was centrifuged 1 hour at 3200×g. Supernatant was first passed over a 0.45 μm filter, and subsequently trough a 0.22 μm filter with exception of the material for oral administration. The filtered homogenate was stored at −70° C. until use.

Example 8

Vaccination-Challenge Experiment

Vaccine Design: Expression of E2 Protein:

The amino acids sequence of CTAPV 1 virus was analyzed. The start and stop of the E2 gene were determined using an alignment of the CTAPV virus genome with Classical Swine Fever virus (CSF) E2 protein (Genbank: AAS 20412.1) and Bovine Virus Diarrhea virus (BVDV) E2 protein (Genbank: AGN03787.1), and predicted cleavage sites of the E2 protein were determined using SignalP4.1 software (www.cbs.dtu.dk/services/SignalP/)

The predicted amino acid sequence of CTAPV 1 E2 (SEQ ID NO: 32):

SCHKRQDYYSIQLVVDGKTGVEKRSIVGKWTVITREGREPRLMEQISMVS

NDSLSETYCYNRLNTSSWGRQPARQRGCGQTVPFWPGDNVLEEQYYSTGY

WVNATGGCQLREGVWLSRKGNVQCQRNGSSLILQLAIKEENDTMEIPCDP

VETESMGPVTQGTCVYSWAFAPRGWYYNRKDGYWLQYVKKNDYQYWTKMP

TASSATTMYRH

Subsequently, the CTAPV E2 nucleotide sequence for expression of CTAPV E2 protein in the Baculovirus expression system in insect cells was optimized using the Genscript OptimumGene™ algorithm (www.genscript.com) (SEQ ID NO: 33).

CGCGGATCCAAAT*ATG*TCATGTCACAAGCGTCAAGACTACTACTCTATCC

AACTGGTGGTGGACGGAAAAACTGGCGTGGAAAAGCGTTCTATCGTGGGC

AAGTGGACGGTCATCACCAGGGAGGGCAGAGAACCGCGCCTAATGGAGCA

AATTTCGATGGTATCTAACGACTCTCTTTCAGAAACCTACTGCTATAACC

GTCTCAATACTAGCTCTTGGGGTCGTCAACCTGCCCGTCAGCGCGGATGT

GGGCAAACCGTCCCCTTCTGGCCTGGTGACAACGTACTCGAGGAACAGTA

CTATAGCACCGGATACTGGGTTAACGCTACTGGCGGTTGCCAACTACGCG

AGGGAGTTTGGTTATCTCGTAAGGGGAACGTGCAATGTCAGCGTAATGGC

TCATCGCTGATCCTTCAACTCGCTATTAAAGAGGAAAACGACACCATGGA

AATCCCGTGCGATCCAGTCGAGACTGAATCAATGGGCCCCGTTACTCAAG

GCACGTGTGTGTACAGCTGGGCTTTCGCCCCTAGGGGATGGTACTATAAC

CGTAAGGACGGCTACTGGCTTCAATACGTGAAGAAAAACGATTACCAGTA

CTGGACCAAAATGCCCACTGCATCCAGCGCGACCACTATGTACCGTCACC

ATCACCATCACCATCACTAAGAATTCTCGAG

The restriction sites BamHI and EcoRI are underlined. The start codon is indicated in Italic and the stop codon is indicated in bold.

Transformation and Expression:

The E2 gene of CTAPV was synthesized at Genscript and directly cloned in a plasmid vector (pFastbac1) using the BamHI and EcoRI restriction sites. The plasmid was transformed to *E. coli* using standard transformation techniques, and subsequently plasmid DNA was purified and used for transfection of SF9 insect cells. The transfection was carried out as follows:

2 ml cell suspension of $5*10^5$ cells/ml was added to each well of a 6 well plate. The cells were allowed to attach to the plate for 1 hour at 27° C. The following transfection solution (200 μl medium without antibiotics, 5 μl miniprep DNA and 6 μl cellfectin (Invitrogen)) was prepared and incubated at room temperature for 45 minutes. After 45 minutes 0.8 ml medium was added to the transfection solution and this was added to the attached cells. The transfected cells were incubated for 4 hours at 27° C. After 5 hours another 1 ml of medium (supplemented with gentamycin and natamycin)

was added to the cells. Cells were grown for 3 days at 27° C. The supernatant was stored at −70° C. as P1 virus stock.

The expression of the CTAPV E2 protein in the SF9 cultures was checked by SDS-page gel electrophoresis. The obtained samples from the SF9 cultures were diluted 1:1 with Bio-Rad Laemmli sample buffer with 5% P3-mercaptoethanol, and subsequently samples were heated to 99° C. for 10 minutes. All samples and a Precision Plus Protein™ All Blue (Bio-Rad) marker were loaded into a Bio-Rad CriterionMTGX™ precast gel (any kD™) and electrophoresed at 200 V for 42 minutes. The electrophoresis buffer used was 1× Tris/Glycine/SDS. After electrophoresis, the gel was stained for 1 hour in InstantBlue™ (Expedeon) protein staining buffer.

Purification:

After expression in SF9 cells, the E2 protein was purified in two different ways. The first purification method was by making a whole cell lysate. A SF9 culture expressing E2 of CTAPV was pelleted, resuspended in PBS and sonicated using a Branson sonifier (2 times 30 pulses, output 5, duty cycle 55%). After sonication the lysate was centrifuged for 10 minutes at 8,000 rpm. The pellet containing the overexpressed E2 was resuspended in PBS. Another way of purifying the E2 protein was by a purification method using IMAC and anionic detergents. This method is described in BMC Biotechnology 2012, 12:95. (BMC Biotechnology 2012, 12:95; Use of anionic denaturing detergents to purify insoluble proteins after overexpression; Benjamin Schlager, Anna Straessle and Ernst Hafen). A lysis buffer containing an anionic denaturing detergent (SDS) was used to lyse the overexpressed E2 culture. The excess of detergent was removed by cooling and purification, prior to affinity purification.

E2 proteins expressed in SF9 cells and purified as describe above were run on SDS-page gel together with Bovine Serum Albumin standards with known protein concentration. Protein concentration was estimated by comparison of band intensities using Genetools software (Syngene version 3.08.07).

Formulation

The final vaccine was formulated in a water-in-oil emulsion based on mineral oil. The water: oil ratio based on weight was 45:55. Droplet size of the emulsion was mainly smaller than 1 m and viscosity was about 80-150 mPa·sec.

Vaccine 1: water phase consisted of purified E2 protein (estimated E2 concentration 60 μg/ml)

Vaccine 2: water phase consisted of whole cell lysate (estimated E2 concentration 62 μg/ml)

Vaccination-Booster

For this experiment, 48 weaner-aged piglets at 5 weeks of age were available. 3×8 animals per group were housed in stable 1, and 3×8 animals per group were housed in stable 2. No contact between animals was possible between stables.

Per group of 8 animals, 6 piglets receive a primo vaccination with vaccine 1, the other 2 piglets were not vaccinated at the beginning of the study.

At t=21 days, 5 out of 6 primo-vaccinated animals in each of the groups received a booster vaccination with vaccine 2.

Blood samples were collected prior to primo vaccination, at day 21 after infection prior to booster vaccination, and at day 39, prior to challenge Of each group, 4 animals that received primo and booster vaccination, plus 2 non-vaccinated animals were moved to the challenge facilities prior to challenge.

Of each group, 1 animal that received only primo vaccination, and 1 animal that received both primo and booster vaccination were monitored for an additional two weeks.

Challenge

The 36 animals for this experiment were housed in stable 3, 3×6 animals per group, group 1-3, and in stable 4, 3×6 animals per group, group 4-6, were housed. The animals in stable 3 originated form stable 1, the animals in stable 4 originated from stable 2.

No contact between animals was possible between stables. No physical contact was possible between animals of different groups within a stable, but air-contact was possible.

Animals were challenged with live virus material on day 39 after primo vaccination.

In stable 3, 3×6 piglets (group 1-3) were challenged with CTAPV 1 challenge material (see above).

Group 1: 10.0 ml oral and 2×2.0 ml nasal

Group 2: 2×1.0 ml IM

Group 3: 2×1.0 ml IM

In stable 4 3×6 piglets (group 4-6) were challenged with CTAPV 8 challenge material (see above).

Group 1: 10.0 ml oral and 2×2.0 ml nasal

Group 2: 2×1.0 ml IM

Group 3: 2×1.0 ml IM

Serum blood samples and nasal, rectal and oropharynx swabs were collected prior to challenge, and at 3, 6, 9, 13, 16, 20, 23 and 27 days post challenge to monitor infection and excretion of CTAPV viruses via qPCR analysis. Three animals (two vaccinated, one non-vaccinated) per group were necropsied at day 13 post challenge, the other 3 animals (two vaccinated, one non-vaccinated) were necropsied at day 27 post challenge. Inguinal lymph nodes, mesenteric lymph nodes and tonsils were sampled at the time of necropsy.

Example 9

Antibodies to CTAPV E2 Protein

Expression of E2 Protein in *E. Coli:*

The amino acids sequence of CTAPV 1 virus was analyzed. The start and stop of the E2 gene were determined using an alignment of the CTAPV virus genome with Classical Swine Fever virus (CSF) E2 protein (Genbank: AAS 20412.1) and Bovine Virus Diarrhea virus (BVDV) E2 protein (Genbank: AGN03787.1), and predicted cleavage sites of the E2 protein were determined using SignalP4.1 software (www.cbs.dtu.dk/services/SignalP/)

The predicted amino acid sequence of CTAPV 1 E2 (SEQ ID NO: 32):

```
SCHKRQDYYSIQLVVDGKTGVEKRSIVGKWTVITREGREPRLMEQISMVS

NDSLSETYCYNRLNTSSWGRQPARQRGCGQTVPFWPGDNVLEEQYYSTGY

WVNATGGCQLREGVWLSRKGNVQCQRNGSSLILQLAIKEENDTMEIPCDP

VETESMGPVTQGTCVYSWAFAPRGWYYNRKDGYWLQYVKKNDYQYWTKMP

TASSATTMYRH
```

Protein Sequence for Expression in *E. Coli* (Includes a HIS-Tag)

```
SCHKRQDYYSIQLVVDGKTGVEKRSIVGKWTVITREGREPRLMEQISMVS
NDSLSETYCYNRLNTSSWGRQPARQRGCGQTVPFWPGDNVLEEQYYSTGY
WVNATGGCQLREGVWLSRKGNVQCQRNGSSLILQLAIKEENDTMEIPCDP
VETESMGPVTQGTCVYSWAFAPRGWYYNRKDGYWLQYVKKNDYQYWTKMP
TASSATTMYRHHHHHHH
```

Subsequently, the CTAPV E2 nucleotide sequence for expression of CTAPV E2 protein in *E. Coli* was optimized using the Genscript OptimumGene™ algorithm (www.genscript.com) (SEQ ID NO: 34).

CATATGTCGTGTCACAAACGCCAAGATTATTATTCTATTCAACTGGTCGT

GGATGGTAAAACGGGTGTCGAAAAACGCTCTATCGTCGGTAAATGGACCG

TGATTACGCGTGAAGGCCGCGAACCGCGTCTGATGGAACAGATCAGTATG

GTTTCCAACGATAGCCTGTCTGAAACCTATTGCTACAACCGCCTGAATAC

GAGCTCTTGGGGTCGTCAGCCGGCACGTCAACGCGGCTGTGGTCAGACCG

TCCCGTTTTGGCCGGGCGACAACGTGCTGGAAGAACAATATTACAGTACC

GGTTATTGGGTGAATGCAACGGGCGGTTGCCAGCTGCGTGAAGGCGTTTG

GCTGTCTCGTAAGGGTAACGTCCAGTGTCAACGCAATGGCAGTTCCCTGA

TTCTGCAACTGGCGATCAAAGAAGAAAACGATACCATGGAAATCCCGTGC

GACCCGGTCGAAACCGAATCAATGGGCCCGGTGACCCAGGGCACGTGTGT

TTATTCGTGGGCATTCGCACCGCGCGGCTGGTATTACAACCGTAAAGATG

GTTATTGGCTGCAGTACGTGAAGAAAAACGACTATCAATACTGGACCAAA

ATGCCGACGGCATCATCGGCTACCACGATGTACCGTCATCACCATCACCA

TCACCATTAACTCGAG

Restriction sites added (in bold) are NdeI and XhoI.

Transformation and Expression:

The E2 gene of CTAPV was synthesized at Genscript and directly cloned in a plasmid vector (pET22b) using the NdeI and XhoI restriction sites. The plasmid was transformed to *E. coli* BL21star+pLysS using standard transformation techniques, and expression was induced.

Expression was achieved by growing the expression strains in autoinducing media for 18 hours at 37° C.

Expression was verified by running SDS-page gel electrophoresis.

E2 was found to be in the insoluble fraction. The E2 protein was purified by applying a purification method using IMAC and anionic detergents. This method is described in BMC Biotechnology 2012, 12:95. (BMC Biotechnology 2012, 12:95; Use of anionic denaturing detergents to purify insoluble proteins after overexpression; Benjamin Schlager, Anna Straessle and Ernst Hafen). A lysis buffer containing an anionic denaturing detergent (SDS) was used to lyse the overexpressed E2 culture. The excess of detergent was removed by cooling and purification, prior to affinity purification.

The purified protein was checked on SDS-page as described in Example 8. The purified protein was formulated in GNE and used for injection of rabbits to generate antibodies. The estimated concentration of the protein in the water phase was 0.5 mg/ml.

FIG. 7 shows that the antibodies raised in rabbits (serum t=4 weeks after vaccination) specifically recognizes an approximately 25 kDa band that corresponds to the CTAPV E2 protein expressed in the baculovirus/SF9 expression system (lane 2). Lane 1 contains a marker and Lane 3 contains an unrelated expression product in the baculovirus/SF9 expression system.

Example 10

SYBR Green One-Step qRT-PCR

Animal Samples

Swine serum and spleen samples were collected from experimentally infected and control pigs. Blood was collected (Vacuolette 8 ml Sep Clot Activator ref: 455071; Greiner Bio-one) and serum was obtained by centrifugation 20 minutes at 3,000×g at 4° C. Sperm samples were obtained from a commercial breeding company and tested without pretreatment.

10% Tissue homogenates were prepared in PBS on ice. Homogenization was performed in Gentle Macs M tubes with the Gentle Macs Dissociator (Miltenyi Biotec). This homogenized material was then centrifuged twice, first at 3,200×g for 30 minutes and subsequently at 10,000×g for 10 minutes. Subsequently a DNase treatment was done: 24 μl 10× Turbo DNase buffer and 20 μl Turbo DNase (AMbion) was added to 250 μl supernatant and this mixture was incubated at 37° C. for 10 minutes.

RNA Extraction

RNA was extracted from these samples with the Magnapure 96 instrument (Roche) with external lysis. This system purifies DNA, RNA, and viral nucleic acids using magnetic glass particle technology. 200 μl sample was mixed with 250 μl magnapure total nucleic acid isolation kit lysis/binding buffer and the extraction was performed in the Magnapure instrument using the external lysis protocol. RNA samples were stored at −70° C. until further use.

SYBR Green One-Step qRT-PCR

Specific Primer Design

Oligonucleotide primers were used to amplify the 5' UTR genome of the CTAPV genome. This part of the viral genome was chosen based on conserved nucleotide sequence between CTAPV variants 1-9 (based on alignment of the nucleotide sequences). The primer sequences were as follows: CTAPV-PAN2-F3-B: CGTGCCCAAAGAGAAATCGG (SEQ ID NO: 35) and CTAPV-PAN2-R3-B (SEQ ID NO: 36): CCGGCACTCTATCAAGCAGT.

qRT-PCR Protocol

A SYBR green based one step qRT-PCR was developed using the Superscript III Platinum SYBR Green One-Step qRT-PCR kit (ThermoFisher). Each reaction contained 25 μl 2×SYBR Green Reaction Mix, 1 μl Superscript III RT/Platinum Taq Mix, 1 μl 10 μM CTAPV-PAN2-F3-B primer, 1 μl 10 μM CTAPV-PAN2-R3-B primer, 17 μl RNAse free water and 5 μl RNA template. All reaction were performed on a BioRad CFX96 with the following cycling parameters; a RT reaction at 55° C. for 3 min, Pre-denaturation at 95° C. for 5 min and then 40 cycles of 95° C. for 15 sec, 60° C. for 30 sec followed by a melting curve program from 60° C. until 95° C. with 0.5° C./5 sec.

Standard Line Creation

For quantification of the detected RNA in the SYBR Green One-Step qRT-PCR a standard line was constructed containing the q-PCR target sequence of which standard dilutions can be calculated. A 177 base pairs long sequence from the 5'UTR part (162-338) of the CTAPV genome was synthesized (Genscript) and ligated in a pUC57 vector that was subsequently transfected in *E. coli*. Plasmid DNA was isolated by midiprep.

The formula for calculating plasmids copies/μl is:

$$\text{Plasmid copies}/\mu l=\text{DNA concentration}(ng/\mu l)/((A\times 328.4+G\times 344.24+T\times 303.22+C\times 304.16)/(6.02\times 10^{23}))\times 2\times 10^{9}).$$

The DNA concentration of the plasmid was 100 ng/l. Eight dilutions were made containing $10^8$ until $10^1$ copies/2 μl.

Results

Validation of the qRT-PCR.

A standard line with eight dilutions containing $10^8$ until $10^1$ copies/5 μl and a negative control sample were included in an experiment to validate the qRT-PCR. FIG. 1A shows a diagram in which the qPCR cycli are plotted against the relative fluorescence units in real time. Each sample was tested in duplicate. The straight line at about 100 RFU is the cut-off line, the straight line at 0 RFU is the negative control sample. The duplicate sample with the highest quantity of template is the sample that shows the initial fluorescence increase around cycle 10 ($10^8$, followed by $10^7$ at cycle 12 etc). FIG. 1B was prepared from the same experimental data, but here the Log starting quantity standard curve (o) is plotted against the quantification cycle. The standard line has an efficiency of 102% and a $R^2$ of 0.997, this is within the range for a specific and quantifiable qPCR in which the efficiency should be between 95% and 105% and the $R^2$ must be above 0.990. FIG. 1C shows the melting curves of the samples shown in panels A and B. All positive samples show identical curves and a specific melting point, which means a specific fragment is amplified and that the fragment is identical in each of the reactions.

These data show that the developed qRT-PCR meets the requirements for the detection and quantification of CTAPV. The qRT-PCR was subsequently used for sample analysis of suspected CTAPV positive samples and control samples. Interpretation of the data was based on the RFU per cycle plus the characteristics of the melting curve. Aberrant melting curves would be indicative for non-specificity of the amplicon.

Detection and Quantification of CTAPV RNA in Serum, Spleen and Sperm Samples.

Serum and spleen from experimentally infected and from control gilts were tested in duplicate for CTAPV RNA presence. Also, sperm samples were tested. The (average) results are presented in Table 9. In the assays performed, the standard lines were confirmed to be within the quality range for an accurate qPCR (FIG. 9B, see above). Also, the CTAPV specific melting point was confirmed in the melting curves of all these samples. Based on these data, we can conclude that the qRT-PCR is appropriate for the detection and quantification of CTAPV RNA in serum, spleen and sperm samples.

TABLE 9

CTAPV RNA quantification of swine serum, sperm and spleen samples.

| | Ct values* | RNA copies/5 μl* | RNA copies/ml* |
|---|---|---|---|
| Serum CTAPV positive gilt 1 | 27.41 | 9.99E+02 | 5.00E+04 |
| Serum CTAPV negative gilt 2 | ND | — | — |
| Spleen CTAPV positive gilt 3 | 29.45 | 7.93E+02 | 3.97E+04 |
| Spleen CTAPV negative gilt 4 | ND | — | — |
| Sperm CTAPV positive boar 1 | 29.75 | 5.39E+02 | 2.70E+04 |
| Sperm CTAPV negative boar 2 | ND | — | — |

*Means of duplicate experiments; ND: not detectable; spleen refers to 10% (w/v) homogenate sample.

Column RNA copies/5 μl shows the number of copies of the virus in 5 μl extracted RNA sample obtained from 200 μl of the original sample.

Column RNA copies/mL shows the number of copies of the virus in the original sample (serum, sperm) or the 10% homogenate (spleen).

Example 11

CTAPV Positive Sperm Infects Gilts and Offspring

Animals

Six gilts were obtained from an SPF/High Health farm. Sperm from a CTAPV-positive boar was used for artificial insemination of the gilts.

Methods

Blood was collected from gilts and offspring (Vacuolette 5/8 ml Sep Clot Activator ref: 455071; Greiner Bio-one) and serum was obtained by centrifugation 20 minutes at 3,000×g at 4° C. Sperm samples were tested without pretreatment.

RNA extraction and qRT-PCR were performed as described in the section "SYBR Green One-Step qRT-PCR" of Example 10.

Results

Tested gilts were serum-negative for CTAPV prior to insemination (qRT-PCR). Boar sperm was positive for CTAPV as analysed by qRT-PCR. At t=+4 weeks after insemination, gilts 4 and 5 contained detectable levels of CTAPV in serum. At the day of farrowing, gilts 1, 2 and 6 contained detectable levels of CTAPV in serum. Piglets with detectable levels of CTAPV in serum were born out of 5 of 6 gilts (see Table 10 for results). Piglets were healthy and showed no clinical tremor or increased incidence of other clinical symptoms related to congenital tremor type AII such as splay legs.

TABLE 10

CTAPV positive sperm infects gilts and offspring

| gilt | RNA copies t = 4 w gestation | RNA copies/mL at farrowing* | Results qRT-PCR serum piglets: | clinical score: |
|---|---|---|---|---|
| 52 | | 1.65E+02 | 6 out of 10 CTAPV positive | 10× no congenital tremor |
| 53 | | 4.15E+01 | 6 out of 11 CTAPV positive | 11× no congenital tremor |
| 54 | | ND** | 0 out of 16 CTAPV positive | 16× no congenital tremor |

TABLE 10-continued

CTAPV positive sperm infects gilts and offspring

| gilt | RNA copies t = 4 w gestation | RNA copies/mL at farrowing* | Results qRT-PCR serum piglets: | clinical score: |
|---|---|---|---|---|
| 55 | 2.47E+02 | ND | 1 out of 15 CTAPV positive | 15× no congenital tremor |
| 56 | 8.70E+01 | ND | 3 out of 17 CTAPV positive | 17× no congenital tremor |
| 57 | ND | 3.19E+04 | 11 out of 18 CTAPV positive | 18× no congenital tremor |

*Column RNA copies shows the number of RNA copies of the virus per mL in the original sample (serum)
**ND: not detected/below detection level Example 12

Infection of Pregnant Gilts with CTAPV Variant 1B Obtained from "Shaking Piglets" and Effect on Newborn Piglets: CTAPV Positive Sperm Animals Six gilts were obtained from a SPF/high health farm. Gilts were inseminated via artificial insemination with CTAPV positive sperm. Pregnancy was confirmed at day 28 of gestation using ultrasound. All gilts gave birth to a litter of piglets on day 115 or day 116 of gestation.

Infection

Three of the gilts were infected on day 32 after insemination with a CTAPV1B inoculum consisting of organ homogenates of spleen and brain obtained from necropsied pig 371 at t=11 days after infection with CTAPV1B infected material. This experiment was described in Example 6/Table 7. The homogenate was prepared as follows. To 14 grams of spleen and 8 grams of brain, 9 times tissue-weight M6B8 medium (MSD AH) with 10 μM HEPES (Sigma H3375-250G) was added. The tissue was homogenized using a blender, followed by shaking with small glass beads for 5 minutes. During homogenizing and subsequent processing, organ-pulp was kept on ice. The organ-pulp was centrifuged 1 hour at 3200×g at 4° C. Supernatant was passed over a 0.22 μm filter. The filtered homogenate was stored at −70° C. until use. These three gilts received an intramuscular injection of 5 mL inoculum (two injections of 2.5 mL each in the left and right neck).

The other three gilts were infected with an inoculum of serum obtained from the same pig at the time of necropsy. The serum was filtered over a 0.22 μm filter prior to injection. These three gilts received an intramuscular injection of 5 mL inoculum (two injections of 2.5 mL each in the left and right neck).

The quantitative amount of CTAPV in the inoculums was determined by qRT-PCR as described in Example 10.

Serum Collection

Serum was collected prior to infection of the gilts, and at t=10 days after insemination. Serum was also collected from newborn piglets within hours after birth. Blood was collected (Vacuolette 5/8 ml Sep Clot Activator ref: 455071; Greiner Bio-one) and serum was obtained by centrifugation 20 minutes at 3,000×g at 4° C. RNA extraction and qRT-PCR were performed as described in the section "SYBR Green One-Step qRT-PCR", Example 10.

Results

The mixed homogenate of spleen and brain used for infection of the first three gilts contained 4.5 E+02 genomes copies per 5 μl of the extracted RNA. This equals 2.3 E+04 genome copies per mL in the homogenate that was used for infection of the gilts.

The serum inoculum used for infection of the other three gilts contained 1.2 E+04 genomes per 5 μl of the extracted RNA, which equals 6.0E+05 genome copies per mL that was used for infection of gilts. Table 11 presents the quantitative amount (genomes per mL serum) at day 10 post infection as determined by qRT-PCR results. Five out of six gilts gave birth to piglets with severe congenital tremor type A-II. One gilt, the gilt with a relatively low virus quantity in the serum at t=10 days after infection, gave birth to a relatively healthy litter where only 2 piglets with mild symptoms were observed. Litter information scored after farrowing is presented in Table 11. An increased incidence of splay legs was associated with clinical tremor, as described by M. White (www.nadis.org.uk/bulletins/congenital-tremor.aspx?altTemplate=PDF).

Presence of CTAPV in three piglets per litter (those with severe clinical tremor, except those piglets born from gilt 44 which showed no clinical tremor) was tested by the qRT-PCR test described in Example 10. The number of CTAPV positive piglets is depicted in Table 11

TABLE 11

RNA quantitation in gilt serum samples on day 10 after inoculation, and litter information.

| Gilt | Infection | RNA copies/mL* | CT type A-II piglets born (live piglets-# severe/# mild/# no symptoms) | CTAPV presence in piglets (piglets tested/piglets positive) |
|---|---|---|---|---|
| 42 | Organ homogenate | 1.1E+05 | 9-4/4/1 | 3/3 |
| 43 | Organ homogenate | 4.5E+04 | 15-7/7/1 | 3/3 |
| 44 | Organ homogenate | 5.5E+02 | 14-0/2/12 | 3/2 |
| 45 | Serum | 1.2E+05 | 18-9/8/0 (1 not scored) | 3/3 |
| 47 | Serum | 1.3E+05 | 16-11/4/1 | 3/3 |
| 48 | Serum | 1.2E+05 | 15-8/7/0 | 3/3 |

*Means of duplicate experiments; Column RNA copies/mL shows the number of copies of the virus in the original sample (serum).

Example 13

Infection of Pregnant Gilts with CTAPV Variant 1B Obtained from "Shaking Piglets" and Effect on Newborn Piglets: CTAPV Negative Sperm Animals Three gilts were obtained from a SPF/high health farm. Gilts were inseminated via artificial insemination with CTAPV negativeregnancy was confirmed at day 28 of gestation using ultrasound. All gilts gave birth to a litter of piglets on day 114 or day 115 of gestation.

Infection

The three gilts were infected with an inoculum of serum obtained from pig 371 at the time of necropsy (see example 12). The serum was filtered over a 0.22 μm filter prior to injection. Three gilts received an intramuscular injection of 5 mL inoculum (two injections of 2.5 mL each in the left and right neck) at 32 days of gestation.

The quantitative amount of CTAPV in the inoculum was determined by qRT-PCR as described in Examples 10 and 12.

Serum Collection

Serum was collected prior to infection of the gilts, and at t=10 days after insemination. Serum was also collected from newborn piglets within hours after birth. Blood was collected (Vacuolette 5/8 ml Sep Clot Activator ref: 455071; Greiner Bio-one) and serum was obtained by centrifugation 20 minutes at 3,000×g at 4° C. RNA extraction and qRT-PCR were performed as described in the section "SYBR Green One-Step qRT-PCR", Example 10.

Results

Table 12 presents the quantitative amount (genomes per mL serum) at day 10 post infection as determined by qRT-PCR results. Two of three gilts gave birth to piglets with mild congenital tremor type A-II. One gilt, the gilt with a relatively low virus quantity in the serum at t=10 days after infection, gave birth to a healthy litter. Litter information scored after farrowing is presented in Table 11.

Presence of CTAPV in piglets with CT type A-II was confirmed by the qRT-PCR test described in Example 10. The number of CTAPV positive piglets is depicted in Table 12. An increased incidence of splay legs was associated with clinical tremor.

TABLE 12

RNA quantitation in gilt serum samples on day 10 after inoculation, and litter information.

| Gilt | Infection | RNA copies/ mL* | CT type A-II piglets born (live piglets -# severe/# mild/# no symptoms) | CTAPV presence in piglets (piglets tested/ piglets positive) |
|---|---|---|---|---|
| 49 | Serum | 5.85E+02 | 13-0/0/13 | 13/0 |
| 50 | Serum | 1.39E+04 | 13-3/8/2 | 13/11 |
| 51 | Serum | 2.32E+04 | 15-1/12/2 | 15/15 |

*Means of duplicate experiments; Column RNA copies/mL shows the number of copies of the virus in the original sample (serum).

The invention claimed is:

1. A gene encoding an E2 protein produced by heterologous expression in a non-pestivirus expression system, wherein the nucleotide sequence of said gene has a level of identity of at least 80% to the nucleotide sequence of SEQ ID NO: 3.

2. The gene of claim 1, wherein the non-pestivirus expression system is a baculovirus or yeast expression system.

3. A DNA fragment comprising the E2 gene of claim 1, wherein the E2 gene is under the control of a functional heterologous promoter.

4. A method of generating the E2 protein of claim 1, comprising expressing a gene encoding the E2 protein in a non-pestivirus expression system, wherein the nucleotide sequence of said gene has a level of identity of at least 80% to the nucleotide sequence of SEQ ID NO: 3.

5. A method of generating the E2 protein of claim 1, comprising incubating cells transfected with the non-pestivirus expression system, lysing the incubated cells, purification of the E2 protein from the lysed cells, and subsequent formulation of the purified E2 protein.

* * * * *

SEQUENCE LISTING

```
<160> NUMBER OF SEQ ID NOS: 36

<210> SEQ ID NO 1
<211> LENGTH: 642
<212> TYPE: DNA
<213> ORGANISM: novel virus

<400> SEQUENCE: 1

aaggttcagt ggttcttaaa ggacgaaaac tcgacgggga tcaatcagat cctgtggcaa      60

agacagatta acagaaccct gcatggagaa tggcctaacc agatctgcca tggcatgcca     120

aatgaaacta ttacagatga ggaattacgt agcctgggaa tgatagacac aagccccaga     180

acaaactaca cttgctgcca gttgcaatat catgaatgga agaaacatgg ttggtgcaac     240

tatccacaaa aacaggtctg gatcaggagg ataacggccc tacaagctaa cctcaccgga     300

gcctatgagg ggcctgagtg tgccgtcatt tgtagattta acggcagcta taacatcgta     360

aaacaagcca gagatgaggt gagtccactg acagggtgca aggaagggca cccttttcta     420

ttctctggtg aaagatccga cacctcatgc ctgaggcccc cttccactag ttgggtaaga     480

ccggtaaaaa tggacgaggc gtcattggct gatagcttcg cccatggggt tgacaaggca     540

ataatactaa tcagaaaagg ggcatcagga ataattaatt tcctagacac tattgggagg     600

tggctaccgg tagctgaggc agctatagta ccatattgtg aa                        642


<210> SEQ ID NO 2
<211> LENGTH: 214
<212> TYPE: PRT
<213> ORGANISM: novel virus

<400> SEQUENCE: 2

Lys Val Gln Trp Phe Leu Lys Asp Glu Asn Ser Thr Gly Ile Asn Gln
1               5                   10                  15

Ile Leu Trp Gln Arg Gln Ile Asn Arg Thr Leu His Gly Glu Trp Pro
            20                  25                  30

Asn Gln Ile Cys His Gly Met Pro Asn Glu Thr Ile Thr Asp Glu Glu
        35                  40                  45
```

```
Leu Arg Ser Leu Gly Met Ile Asp Thr Ser Pro Arg Thr Asn Tyr Thr
    50                  55                  60

Cys Cys Gln Leu Gln Tyr His Glu Trp Lys Lys His Gly Trp Cys Asn
65                  70                  75                  80

Tyr Pro Gln Lys Gln Val Trp Ile Arg Arg Ile Thr Ala Leu Gln Ala
                85                  90                  95

Asn Leu Thr Gly Ala Tyr Glu Gly Pro Glu Cys Ala Val Ile Cys Arg
            100                 105                 110

Phe Asn Gly Ser Tyr Asn Ile Val Lys Gln Ala Arg Asp Glu Val Ser
        115                 120                 125

Pro Leu Thr Gly Cys Lys Glu Gly His Pro Phe Leu Phe Ser Gly Glu
    130                 135                 140

Arg Ser Asp Thr Ser Cys Leu Arg Pro Pro Ser Thr Ser Trp Val Arg
145                 150                 155                 160

Pro Val Lys Met Asp Glu Ala Ser Leu Ala Asp Ser Phe Ala His Gly
                165                 170                 175

Val Asp Lys Ala Ile Ile Leu Ile Arg Lys Gly Ala Ser Gly Ile Ile
            180                 185                 190

Asn Phe Leu Asp Thr Ile Gly Arg Trp Leu Pro Val Ala Glu Ala Ala
        195                 200                 205

Ile Val Pro Tyr Cys Glu
    210


<210> SEQ ID NO 3
<211> LENGTH: 633
<212> TYPE: DNA
<213> ORGANISM: novel virus

<400> SEQUENCE: 3

tcgtgccaca agagacaaga ctattacagt atccagctag tcgttgacgg aaaaacgggc      60

gtagaaaaac gatctatagt gggcaagtgg acagtgataa ctagggaagg tcgggaacca     120

agattaatgg agcaaataag catggtgtca aatgatagct tatcagaaac ttactgctac     180

aataggctaa atactagcag ttgggggcga caaccggcaa gacagagagg gtgtggtcaa     240

accgtaccct tttggcctgg tgacaatgtc ctggaagaac aatactatag cacaggttac     300

tgggtaaatg caacaggtgg ttgccagttg agagaaggcg tgtggctatc aagaaagggc     360

aatgtacagt gccagcgtaa cggctcatcc ttgatactgc aactggcgat aaaagaagag     420

aatgacacta tggaaatacc atgtgacccg gtggaaaccg aaagtatggg tccagttaca     480

cagggcactt gcgtgtacag ctgggcattc gccccaagag ggtggtatta caacaggaaa     540

gatggttatt ggctccagta cgtaaagaaa aacgactacc agtactggac gaaaatgccc     600

actgcttcat ccgccacaac gatgtaccgc cat                                   633


<210> SEQ ID NO 4
<211> LENGTH: 210
<212> TYPE: PRT
<213> ORGANISM: novel virus

<400> SEQUENCE: 4

Ser Cys His Lys Arg Gln Asp Tyr Tyr Ser Ile Gln Leu Val Val Asp
1               5                   10                  15

Gly Lys Thr Gly Val Glu Lys Arg Ser Ile Val Gly Lys Trp Thr Val
            20                  25                  30

Ile Thr Arg Glu Gly Arg Glu Pro Arg Leu Met Glu Gln Ile Ser Met
        35                  40                  45
```

```
Val Ser Asn Asp Ser Leu Ser Glu Thr Tyr Cys Tyr Asn Arg Leu Asn
    50                  55                  60

Thr Ser Ser Trp Gly Arg Gln Pro Ala Arg Gln Arg Gly Cys Gly Gln
65                  70                  75                  80

Thr Val Pro Phe Trp Pro Gly Asp Asn Val Leu Glu Glu Gln Tyr Tyr
                85                  90                  95

Ser Thr Gly Tyr Trp Val Asn Ala Thr Gly Gly Cys Gln Leu Arg Glu
            100                 105                 110

Gly Val Trp Leu Ser Arg Lys Gly Asn Val Gln Cys Gln Arg Asn Gly
        115                 120                 125

Ser Ser Leu Ile Leu Gln Leu Ala Ile Lys Glu Glu Asn Asp Thr Met
    130                 135                 140

Glu Ile Pro Cys Asp Pro Val Glu Thr Glu Ser Met Gly Pro Val Thr
145                 150                 155                 160

Gln Gly Thr Cys Val Tyr Ser Trp Ala Phe Ala Pro Arg Gly Trp Tyr
                165                 170                 175

Tyr Asn Arg Lys Asp Gly Tyr Trp Leu Gln Tyr Val Lys Lys Asn Asp
            180                 185                 190

Tyr Gln Tyr Trp Thr Lys Met Pro Thr Ala Ser Ser Ala Thr Thr Met
        195                 200                 205

Tyr Arg
    210


<210> SEQ ID NO 5
<211> LENGTH: 579
<212> TYPE: DNA
<213> ORGANISM: novel virus

<400> SEQUENCE: 5

acttacactg tgacagggat gtatgtccat gtgaagaatt gtctccctag agggttaccg      60

aagcattcaa agataatttc cccgacaata atatacttgg gggaaggtga cccagcccat     120

aatattcagc acttatttgg ctcaggtata gcaaagtggg tcttagtcct actcggggtt     180

ctgggtgagt ggtatggaga attggcctct acaatatact tactactaga gtatgggtct     240

gagtggttgg aacatgaaag tctggtcacg gaagggttga tccctggcat caatattaca     300

atagaactcc cagctagtca tactgtacct ggttgggtgt gggtcgcagg ccggtgggta     360

tgcgtgaaac cagattggtg gcccacacag atttggattg aaactatagt ggcagaggtc     420

tggcatatac taaaaatatt ggcatcagcc ctggtaaaca tagtcactgc attcgtaaac     480

ctggaattgg tatacctggt cataatatta gtcaaaatat caaaggggaa cctgataggc     540

gctatattgt ggtgcctatt actgtcaggg gctgaaggc                            579


<210> SEQ ID NO 6
<211> LENGTH: 193
<212> TYPE: PRT
<213> ORGANISM: novel virus

<400> SEQUENCE: 6

Thr Tyr Thr Val Thr Gly Met Tyr Val His Val Lys Asn Cys Leu Pro
1               5                   10                  15

Arg Gly Leu Pro Lys His Ser Lys Ile Ile Ser Pro Thr Ile Ile Tyr
            20                  25                  30

Leu Gly Glu Gly Asp Pro Ala His Asn Ile Gln His Leu Phe Gly Ser
        35                  40                  45
```

-continued

```
Gly Ile Ala Lys Trp Val Leu Val Leu Leu Gly Val Leu Gly Glu Trp
    50                  55                  60

Tyr Gly Glu Leu Ala Ser Thr Ile Tyr Leu Leu Leu Glu Tyr Gly Ser
65                  70                  75                  80

Glu Trp Leu Glu His Glu Ser Leu Val Thr Glu Gly Leu Ile Pro Gly
                85                  90                  95

Ile Asn Ile Thr Ile Glu Leu Pro Ala Ser His Thr Val Pro Gly Trp
            100                 105                 110

Val Trp Val Ala Gly Arg Trp Val Cys Val Lys Pro Asp Trp Trp Pro
        115                 120                 125

Thr Gln Ile Trp Ile Glu Thr Ile Val Ala Glu Val Trp His Ile Leu
    130                 135                 140

Lys Ile Leu Ala Ser Ala Leu Val Asn Ile Val Thr Ala Phe Val Asn
145                 150                 155                 160

Leu Glu Leu Val Tyr Leu Val Ile Ile Leu Val Lys Ile Ser Lys Gly
                165                 170                 175

Asn Leu Ile Gly Ala Ile Leu Trp Cys Leu Leu Leu Ser Gly Ala Glu
            180                 185                 190

Gly


<210> SEQ ID NO 7
<211> LENGTH: 18
<212> TYPE: DNA
<213> ORGANISM: artificial sequence
<220> FEATURE:
<223> OTHER INFORMATION: primer

<400> SEQUENCE: 7

gccatgatgg aggaagtg                                                    18


<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8

gggcagrttt gtggattcag                                                  20


<210> SEQ ID NO 9
<211> LENGTH: 18
<212> TYPE: DNA
<213> ORGANISM: artificial sequence
<220> FEATURE:
<223> OTHER INFORMATION: primer sequence

<400> SEQUENCE: 9

cggatacaga aatactac                                                    18


<210> SEQ ID NO 10
<211> LENGTH: 20
<212> TYPE: DNA
<213> ORGANISM: artificial sequence
<220> FEATURE:
<223> OTHER INFORMATION: primer

<400> SEQUENCE: 10

ccgaatgcag ctarcagagg                                                  20


<210> SEQ ID NO 11
```

<211> LENGTH: 24
<212> TYPE: DNA
<213> ORGANISM: artificial sequence
<220> FEATURE:
<223> OTHER INFORMATION: primer

<400> SEQUENCE: 11
gaaacagcca tgccaaaaaa tgag 24

<210> SEQ ID NO 12
<211> LENGTH: 23
<212> TYPE: DNA
<213> ORGANISM: artificial sequence
<220> FEATURE:
<223> OTHER INFORMATION: primer

<400> SEQUENCE: 12
agtgggttcc aggggtagat cag 23

<210> SEQ ID NO 13
<211> LENGTH: 24
<212> TYPE: DNA
<213> ORGANISM: artificial sequence
<220> FEATURE:
<223> OTHER INFORMATION: primer

<400> SEQUENCE: 13
gaaacagcca tgccmaaraa tgag 24

<210> SEQ ID NO 14
<211> LENGTH: 23
<212> TYPE: DNA
<213> ORGANISM: artificial sequence
<220> FEATURE:
<223> OTHER INFORMATION: primer

<400> SEQUENCE: 14
agtgggttcc aggrgtagat yag 23

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
gagtacgggg cagacgtcac 20

<210> SEQ ID NO 16
<211> LENGTH: 25
<212> TYPE: DNA
<213> ORGANISM: artificial sequence
<220> FEATURE:
<223> OTHER INFORMATION: primer

<400> SEQUENCE: 16
catccgccgg cactctatca agcag 25

<210> SEQ ID NO 17
<211> LENGTH: 20
<212> TYPE: DNA
<213> ORGANISM: artificial sequence
<220> FEATURE:
<223> OTHER INFORMATION: primer

<400> SEQUENCE: 17
atgcataatg ctttgattgg 20

<210> SEQ ID NO 18
<211> LENGTH: 20
<212> TYPE: DNA
<213> ORGANISM: artificial sequence
<220> FEATURE:
<223> OTHER INFORMATION: primer

<400> SEQUENCE: 18
gtgacgtctg ccccgtactc 20

<210> SEQ ID NO 19
<211> LENGTH: 11561
<212> TYPE: DNA
<213> ORGANISM: novel pestivirus

<400> SEQUENCE: 19
gcataatgct ttgattggct gcattatgta tgggacatcc taaattgttg tgagccctgt 60
ggtgagtggg ggaaaggggt taaccaggcc tctagtacca caggcaccaa cagacagggc 120
aactcgaacc tgagagagag gtaccgagct cttaagcccc gagtacgggg cagacgtcac 180
cgagtagtac acccaaagac caccacttct aggtgtaggg tctactgagg ctcgggtgga 240
cgtgggcgtg cccaaagaga aatcggtggt gggcctgggg gtcggggcca ccatgcccct 300
ttatggggta gaccttactg cttgatagag tgccggcgga tgcctcgggt aagagtataa 360
aatccgttgt ctattaacat ggaaaaacag attgcacatt acttaaaaaa agaaaaacaa 420
aggaatgggt ggacggaact ggtggtagga gaaagtcaca ctaaaataac tacgctttct 480
ggaaagacct atcgaggtac ttgggaaatg gagaaacggc caaatcctta cggaacctat 540
tttcccagac ctagtcccca gcagctcaca gccctacacc cccacccagt ggtaaattgc 600
aaggtgatag agtacaaggg gacggaccct aattatggtg attgcccaaa tacaaacggg 660
gtgttcatcg atgaaaaggg tagaaggttg agcagccctc cattaggtat ttggaagata 720
agattggact acagcgacct gataaatata aacagaccag tccccactag aggggaaaac 780
tcttatcgag tcgagacctg cagtggggag ctggctactg taatgctggt acacaatagg 840
gtacttgtgg aagactgtag ggggctatac caatggaaac ccaactgtga aggaattgtg 900
ctctatgtaa aaacttgttc tgattgggca gatcaggtgg aaaaacagga gaagggaagc 960
cccccaaaac cacaacggcc accaaggcga gacccacgaa aaggcttaca accacaagtc 1020
cccagagaaa ctgaggttac ggaaaagaag aggcaaccta gtgtcacctt agtagcaggg 1080
gggcagaagg cccaaatcat ctacaaaggc aggactaaaa ataaaaagac tccggatggg 1140
gtctataagt acccaggagc taaagaaggg gatgtggtaa aggtcaggaa gatgcttaag 1200
aattggcata tagccttgat aatgtacctg atatatatta taactccagg ttttgccaag 1260
gttcagtggt tcttaaagga cgaaaactcg acggggatca atcagatcct gtggcaaaga 1320
cagattaaca gaaccctgca tggagaatgg cctaaccaga tctgccatgg catgccaaat 1380
gaaactatta cagatgagga attacgtagc ctgggaatga tagacacaag ccccagaaca 1440
aactacactt gctgccagtt gcaatatcat gaatggaaga aacatggttg gtgcaactat 1500
ccacaaaaac aggtctggat caggaggata acggccctac aagctaacct caccggagcc 1560
tatgaggggc ctgagtgtgc cgtcatttgt agatttaacg gcagctataa catcgtaaaa 1620
caagccagag atgaggtgag tccactgaca gggtgcaagg aagggcaccc ttttctattc 1680

-continued

```
tctggtgaaa gatccgacac ctcatgcctg aggccccctt ccactagttg ggtaagaccg   1740

gtaaaaatgg acgaggcgtc attggctgat agcttcgccc atggggttga caaggcaata   1800

atactaatca gaaaaggggc atcaggaata attaatttcc tagacactat tgggaggtgg   1860

ctaccggtag ctgaggcagc tatagtacca tattgtgaaa cttacactgt gacagggatg   1920

tatgtccatg tgaagaattg tctccctaga gggttaccga agcattcaaa gataatttcc   1980

ccgacaataa tatacttggg ggaaggtgac ccagcccata atattcagca cttatttggc   2040

tcaggtatag caaagtgggt cttagtccta ctcggggttc tgggtgagtg gtatggagaa   2100

ttggcctcta caatatactt actactagag tatgggtctg agtggttgga acatgaaagt   2160

ctggtcacgg aagggttgat ccctggcatc aatattacaa tagaactccc agctagtcat   2220

actgtacctg gttgggtgtg ggtcgcaggc cggtgggtat gcgtgaaacc agattggtgg   2280

cccacacaga tttggattga aactatagtg gcagaggtct ggcatatact aaaaatattg   2340

gcatcagccc tggtaaacat agtcactgca ttcgtaaacc tggaattggt atacctggtc   2400

ataatattag tcaaaatatc aaaggggaac ctgataggcg ctatattgtg gtgcctatta   2460

ctgtcagggg ctgaaggctc gtgccacaag agacaagact attacagtat ccagctagtc   2520

gttgacggaa aaacgggcgt agaaaaacga tctatagtgg gcaagtggac agtgataact   2580

agggaaggtc gggaaccaag attaatggag caaataagca tggtgtcaaa tgatagctta   2640

tcagaaactt actgctacaa taggctaaat actagcagtt gggggcgaca accggcaaga   2700

cagagagggt gtggtcaaac cgtacccttt tggcctggtg acaatgtcct ggaagaacaa   2760

tactatagca caggttactg ggtaaatgca acaggtggtt gccagttgag agaaggcgtg   2820

tggctatcaa gaaagggcaa tgtacagtgc cagcgtaacg gctcatcctt gatactgcaa   2880

ctggcgataa aagaagagaa tgacactatg gaaataccat gtgacccggt ggaaaccgaa   2940

agtatgggtc cagttacaca gggcacttgc gtgtacagct gggcattcgc cccaagaggg   3000

tggtattaca acaggaaaga tggttattgg ctccagtacg taaagaaaaa cgactaccag   3060

tactggacga aaatgcccac tgcttcatcc gccacaacga tgtaccgcca tttgctccct   3120

ttactggtgg cctgcctcat gggcggtaga atatcggtat ggattgtggc gatgctcctg   3180

tctttacagg tggaagctag tgaagtaggt accaagcaac tggctgtcac gctaactctg   3240

tggaaaatgg actggacaga attactcttc tatattgtta taatgctagc cgttaaggaa   3300

gaactcataa aaaaaatagt gactgcaagc cttgtggcct taaaaaatag tccagtagcc   3360

ttgagcttcc ttattgtact caggcttgtg gggggtagtg aggcactccc agtgggtttg   3420

ttattagaaa agatgtgcat agaccaaccg gagtttggaa ccccttttcct gatctaccta   3480

tgggacaatt ggaagtggac tgtactagtc agcttctccg cactgaatca tgaaaaaact   3540

ataaaactgg caagaaaact gctgttggca acacacataa cagcgctcac attgactggt   3600

ctgagtgatt caatcttcta tatgatgctt ataatgacta atttattaat aaagacattc   3660

atatatctac tgggagccag tataaattgg gtcgagagag aaaaaaagaa gttgctagtg   3720

aagagaacac taatatataa gaaagccgcg atttgcagtc aagatggaaa tgaattggag   3780

aataaattta ataagataac tgtaaatgcg gatttcaccc catgtaaact tgaacttctg   3840

caactactca gggctttttt agtctctcta tgcttttcct attacaagcc tctcctgtat   3900

gcggaaacta ctctaaccgt aatagtaatt ggcgtacagg agtacaacgt agctatggct   3960

cgcgggcgaa gcgtggtcca tagactgcta gccatggcct actacatata cggccgtata   4020

cagggtgaca tgttccagct cgccactatc cagtgcctgt tgtcaagtcc taggaaaatt   4080
```

-continued

```
atgaaacaca tgatagaaaa tccaactctt aagaagctct ggcaaggtga aacagagctt   4140
tttaaccagg gtgtcagcca gtccaaaata gtgaatccaa agagtattgg gctggaagaa   4200
ttacacaagg gtatgtgcgg cctcccaact gtagtgcaaa atttggtcat atatgctaag   4260
aagaatgact ctcttatctt aggagagctg ggttaccccc ctggggacct caccagtgac   4320
gggtgggaaa ttttaggtcc tggcagaatc ccaaagatta ccaacgttga gtccgctaaa   4380
atggacttac tctccaagct tatgaccttt ctgggggttg agagctcaag agtccccagg   4440
accccagtcc actcgacaag gaaattattg aagatagtga gaggcttaga aactggatgg   4500
ggatacaccc atgcaggggg gataagtagc gcaaaacacg tcacaggtga aaaaaacttg   4560
atgactcaca tggaaggcag gaagggaaag tatatcctac aatcccaaga acatggtgct   4620
gatgaggtag aatatggagt gaaaactgac caaaaagcac ccgacaatgc cttatgctac   4680
tgctttaacc ctgaagccac aaacataaaa ggagaaacgg gagccatggt gtttatgaag   4740
aagataggaa aaaaatggac tctcgtaaca tcagatggta acaaagccta ttataatgta   4800
aacaacctga aagggtggtc tggactaccg ataatgttgc actctaccgg ggctatagta   4860
gggaggatta agtcagcgta ttcagatgaa aacgacttgg tagaggaact tatcgactcc   4920
aggactatca gcaagagcaa tgaggcaaac ctggatcacc ttatcaagga attagcagat   4980
atgcggaggg gggagtttcg ctccatcacc cttggaacag gagctgggaa aactacagaa   5040
ctgcccaggc aataccttac aacggtgggt gcccataaat cagtgttggt cctagtccct   5100
ttaaaagcac ctgctgaaag tgtctgtcgc ttcatgaggt ccaaataccc tactatcaac   5160
ttttccttga gagtgggggga gcggaaagag ggggatgtga gcagtggcat cacttacgcc   5220
acgtacggat tctgctgcca gctaaaccta gtccaactca aagaatggat atccaggtac   5280
tcaatggtgt tttttgatga ataccacaca gcaactccag aacaaatagc aataataagt   5340
aagatccatg cactgaaggt caaaaccagg atagtggcta tgtcagcaac tcccccgggt   5400
accgtgacga ctgaaggcag gaaatttgat attgaagagg taggggttgc cactatagag   5460
aaaggagagg aaccaaaaag ggggcgtata gcggtagctg gtatgcaggt cccattagaa   5520
gacttgacgg ggaagaactg cctagtgttc gtcgcaacca aagaagctgc ggagacagag   5580
gctaaagaac tgcgtgccag gggagttaat gccacctact actattcagg catagaccct   5640
aagactctgg aacatgggat gaccaatcag ccatattgta ttgtggctac caatgctatc   5700
gaatcaggca taacttgtcc tgacttagac gtggtcatag ataccatgca gaagtatgaa   5760
aaagtagtga atttttcagc aaagctgccc ttgattgtca cttcattagt aaagaagaaa   5820
attactaggg aagaacaggg ccagaggaaa ggtcgggtag gtagacaaaa gaagggaaaa   5880
tactactacc cttcaggagt ggtaccgaat gggtcaaaag acctaagcta tttaatcctg   5940
caggctcaag agtacggtat cttggaacaa gttaatataa cagagtactt catcataatg   6000
aatgaggact ggggtcttta tgatgtagat gaggtagagg taagaatact tgagagaatg   6060
aacaaggaaa ttctgcttcc gctaggtatc gtggagaagc aaatcctgga aagaagcact   6120
cacccggaaa aagtggcatt gttgtataac aaattagtac agaaaaaccc tatagtatac   6180
cctaaagtac aggaaggtga ggtcagcaag gaatacaata cccataatct ggccgtatac   6240
gataaactaa aagatgtcaa cccacaagcc atttatgtcc tagctgaaga ggagagagcc   6300
acggaaatga tgggccttga gtttgaacaa gacccttctg acttacagga ctcagtagct   6360
caactttgtg aagacatcaa gaggtataca aaactctctg ggatcactga gaaattatta   6420
```

-continued gtaggcacga tggtggggta tattggatat aaagccctaa ccagaaacca cgtgccctgg 6480
gtcagtaagg agtatagtta tgagctgacc gattcaccgg acacttacga aaattcattt 6540
gcacctttgg atgtcgacgt ccaaaacccc ggtgagggaa aacacccaga gcaactggca 6600
gaccatcaac tgaggcaact actggagacc gggagagaca aggcgattga cttcttaaaa 6660
ggaatccgcg agttcgctag tggggccatt aacagtccaa aggcattaag tatatgggag 6720
aaaatgtatc agtacttgag gaagcatcag ggtgagatta tcgcatcagc ggcgtggggc 6780
agtgcaacag ccctccacga cagtattaaa tctaggcttg gagatgaggt cgctactgca 6840
gtaataatcc tcaagtatct agcatttggt gaaagagaac tgtccggact gactaggcaa 6900
gtcctaattg acattatagt gtattatata gtcaacaagc cccggtttga aggggatgac 6960
tatgcaaaga gaaagggaag aaggctagtc attgaagtct tgatgggggc actggcaact 7020
tatgcagtgt ccaacttttg gggcgtgtcc atcaataaga tactgcaacc aatatctgac 7080
tatttaccct atgccaccgc cactttggct ttccttcgcc caactttcat ggaatcagca 7140
gtggtggtcg cttcctctat ctatagagct ttcctctcca ttaaacatgc ggaaaacagg 7200
agtcttgtca cacaggttgc ttctgccgcc cttgaagtca tgggcttgac cccagtatca 7260
gccggcctag gcgtcttact ggggctcggg ctatgcgtgc tccatatgaa catcgacaaa 7320
aacgaggaga aaaggacact gatactgaaa atgtttgtca aaaactttat agaccaggcg 7380
gcactagacg agttagacaa actggagcca gaaaaaataa tcctctcatt gttggagggt 7440
attcaaactt gcacaaaccc ggtcagagca atcatgattt tgtacagggt gtactataag 7500
ggggaatcgt tcacagaagc tttgtctaag atggctggca agtccctcat cgtgatggtc 7560
atagtcgagt tcctagaact gacgggccaa acccaagggg ggtacataga tcttagtgcc 7620
aatttgctga cccttctcct agaaaaacta aaaaagatga ccaacctcgc catcggggaa 7680
gctagaaagg tcttacttcc tatcccatac ttgtactgtg aaacctggca gtctgacgcc 7740
agaatcaagg ctcctgagtc ctatgatcaa gtggtagtgg aatgcaaatg tggtgcttca 7800
gcaaggtatt ccttccgaca tggggttcac gagatactgg aagaaaaaag aaccaagtgg 7860
tgtaagaact tcttcttgtg ggacctaac tttcacaacc cggatccaaa gaggatgaca 7920
ttctatgagt tcggccaagc aaaaaaatgt cctgttgtca taatgggtga agacataacc 7980
ttcggcaaat atggtatata tatcaaattc ggccataagc ctgatggggg aaggttaata 8040
aggggcacca cccacgccac tattagcagg gaggaactgc tggaaattct aacggctcca 8100
agccaagtgg ccataggcaa agtcaagctg accgattact gtaatcaaaa aggaataata 8160
gacaggaaac tggccgtact tgaaggtgac aaaatacatt tttggaaagc acaccgtgga 8220
tccaagatca cagatcaact cactattgag agtctgacag atgatttggg gtcagaaatc 8280
agggacatta catgggagct gtacacaggc gggacgtgca ccgttaaggg gatatccctt 8340
agatcatgcg cgccaggtca aagaaataag gctacggtct tgtgcgattg cactgacgta 8400
cttagcccct gttacttagt caacggaagg agaccatccc catttgacgt cgtggaaggt 8460
tatgaatgcc accatcggaa gccccgagcg acgtatgagg acttagaaat ggaggaaata 8520
ctaaagagaa gggtccctgt ttatgatcct ttgagtctgt ttgacactga cagtaaactg 8580
ctgcctcctg acacctatta cttggaagaa gatcaagaag acttcgagta tgcattgagg 8640
tgttggggcc tcggggttta tgtaacggac gggcctgcta tttctccccc ggacataagg 8700
gtacaccaca gttctgtact gttactgttg acacctggag tggactctga gttgccctta 8760
cagtacatac gttgttactc tcatcaggtg gaggtggaca tctatattag gggccaactt 8820

```
ctggaggagg aagatactgc cacggaggcg gaagactctc aggaagatag tgatgaaggg   8880
atgggcgacg tggtaataaa agatgaggat acattgtcca caacagaatc aatacccccca   8940
ctagaagagg aggaaggggg cgaagagcca atcacttatg tggtcattag ggattacaa   9000
gaagaaagat atactagcca tcttaaatta agtgactgga tcagtgaaaa tatttcggag   9060
ccacatagag tccaaattat gcttgatgga acggtgagag tcacaataaa agagggcaaa   9120
gtcaaacacc tatttggggt ctacagaatc gaaaactccc tggaagcaat gtttaaagag   9180
accatagctg accttcctgt agccacccaa ccgccccgag ggccaatcta cacggccaaa   9240
gagttggctc aagggaacat tgccccgatc caacccgcag caaactttta tggaatgata   9300
gaggggagag gtgatccaat gacggcattc gaagccttat cagtcctgcg gtcacaaaaa   9360
gtctcagcta aggaagtgaa gatgaacacc cgcagggctc aagcttttct gaataaagtc   9420
agggggactg ctgaggtcag agcatcagaa ttaacattaa aatgcttgcc agcacttggt   9480
aaagtaaatg ggaggaaatt gattagagag gaaaccaaca tccccaacca aaggttggca   9540
tcaataatga cctcaatagg aattagatta gaaaaactgc cggtggttag agcaaacacc   9600
tctggctcta agttcaggca gtcgatctta gaaaaaatgg ataaatatga aaatgaacaa   9660
gttccagggt tacatgagaa aatgtgggca gcattcttgg caactgccag gcaagactta   9720
agaaacacat atgaagaagt aacttatctt gaactggaga ccggaatcaa ccggaaggga   9780
gctccaggtt tttttgagaa agaaagttca ataggagaag tgctggaaag aaaaggaaaa   9840
attgacgttg taatccaaga gattgaaaaa ggcaaccact tgtactatga aacagccatg   9900
ccaaaaaatg agaaaagaga cgtgcttgat gattggttgt ctgaggactt cgtcacttat   9960
aagaaaccac gtgtaataca gtaccctgag gcagtcaccc ggttggccat caccaaaata  10020
atgtacaagt gggtaaaaca gaaacctata gtgattcccg gttacgaggg aaaaaccccg  10080
atctttgaaa tattcgaaaa agttagtgca gattgggctc agttcagaaa cccggtagca  10140
gtcagctttg ataccaaagc ttgggacaca caagtaacta gagaggacct caggctggtg  10200
gggcggatac agaaatacta ctacaaaaaa aagtattgga aattcattga caatttgacg  10260
gccatgatgg aggaagtgcc tgtgatcact gtagaaggag atatgttcct cagagttgga  10320
cagcgcgggt ccgggcagcc tgatacctca gcaggcaatt ccatattaaa tgtgctaaca  10380
atgttagtag ccttctctga atccacaaac ctgcccatag cggccgcctg gaaggcttgt  10440
cggatccacg tctgtgggga cgatggcttt ttaatcacgg aatcagaatt agggcggaaa  10500
ttcgctgaaa aaggtgtccc tctgctagct gcattcggca aacctcaaaa gattacagag  10560
ggagcaagcc taaagataac cagtaatttt gacggaatag agttttgtag tcattctccc  10620
attagagtcc aaacaccaaa cataaggtgg atgccagcga ggcctacagc aacaattcta  10680
ggcaaaatga gtaccaggct gggtgagggt gctaccagat caggagaaga atatgaaaaa  10740
caggtggcat ttgcatatct actgatgtac ccctggaacc cactggtcag gagaatcagc  10800
ctcctactgt tgtcaaccac tgacccaatg gggagagagg aaaccccatg ctctgatgag  10860
ggggtgaagt atgttgggga ccctatcgct gcatacaggg atgtatgggg gcacaaatta  10920
gaggacgtag gacacgtcga tcagccgcag ttatcccgga tgaattatag catgacttac  10980
ttagggatct ggaaaccaaa gacgagccag cggttagttg aacaatgctg tcgactggcc  11040
gagaaaaaca attgtgtggc acgtgctgat tccctaatta agaaaaaggt caagatcacc  11100
tatgacccgg ggataggagc ggctcaggtc attcgtaggt gggaagagct tgagtggacc  11160
```

agaaggaaac ctgaaccttc taatgcaacc gcagaagatg atatcttcct agtcctgtgg 11220
aaaagatttt caaagtacat tttccagaaa atgaagttca tgcagagaat gctggccccc 11280
tactaagtgg gaagcgttca tttaattata accagtatct ggtaagtata agacttgtgt 11340
aaataaaaca tataactgaa aggggcaggt ggccgtacag gctggggcga tcgccgcacc 11400 ccccttcgc caggcgcctc aaccccatac accatggggt tgttgtaaat acttgaaaga 11460
atggagtaat acgggtaata aacttacagg ccagtattgc cccatttgct ttgtagtggt 11520
gacgacctgt ataggtctga tctagatgaa gcaagggggc c 11561

<210> SEQ ID NO 20
<211> LENGTH: 5048
<212> TYPE: DNA
<213> ORGANISM: novel pestivirus

<400> SEQUENCE: 20
gcataatgct ttgattggct gcattatgta tgggacatcc taaattgttg tgagccctgt 60
ggtgagtggg ggaaaggggt taaccaggcc tctagtacca caggcaccaa cagacagggc 120
aactcgaacc tgagagagag gtaccgagct cttaagcccc gagtacgggg cagacgtcac 180
cgagtagtac acccaaagac caccacttct aggtgtaggg tctactgagg ctcgggtgga 240
cgtgggcgtg cccaaagaga aatcggtggt gggcctgggg gtcggggcca ccatgcccct 300
ttatggggta gaccttactg cttgatagag tgccggcgga tgcctcgggt aagagtataa 360
aatccgttgt ctattaacat ggaaaaacag attgcacatt acttaaaaaa agaaaaacaa 420
aggaatgggt ggacggaact ggtggtagga gaaagtcaca ctaaaataac tacgctttct 480
ggaaagacct atcgaggtac ttgggaaatg gagaaacggc caaatcctta cggaacctat 540
tttcccagac ctagtcccca gcagctcaca gccctacacc cccacccagt ggtaaattgc 600
aaggtgatag agtacaaggg gacggaccct aattatggtg attgcccaaa tacaaacggg 660
gtgttcatcg atgaaaaggg tagaaggttg agcagccctc cattaggtat ttggaagata 720
agattggact acagcgacct gataaatata aacagaccag tccccactag aggggaaaac 780
tcttatcgag tcgagacctg cagtggggag ctggctactg taatgctggt acacaatagg 840
gtacttgtgg aagactgtag gggctatac caatggaaac ccaactgtga aggaattgtg 900
ctctatgtaa aaacttgttc tgattgggca gatcaggtgg aaaaacagga gaagggaagc 960
cccccaaaac cacaacggcc accaaggcga gacccacgaa aaggcttaca accacaagtc 1020
cccagagaaa ctgaggttac agaaaagaag aggcaaccta gtgtcacctt agtagcaggg 1080
gggcagaagg cccaaatcat ctacaaaggc aggactaaaa ataaaaagac tccggatggg 1140
gtctataagt acccaggagc taaagaaggg gatgtggtaa aggtcaggaa gatgcttaag 1200
aattggcata tagccttgat aatatacctg atatatatta taactccagg ttttgccaag 1260
gttcagtggt tcttaaagga cgaaaactcg acggggatca atcagatcct gtggcaaaga 1320
cagattaaca gaaccctgca tggagaatgg cctaaccaga tctgccacgg catgccaaat 1380
gaaactatta cagatgagga attacgtagc ctgggaatga tagacacaag ccccagaaca 1440
aactacactt gctgccagtt gcaatatcat gaatggaaga aacatggttg gtgcaactat 1500
ccacaaaaac aggtctggat caggaggata acggccctac aagctaacct caccggagcc 1560
tatgaggggc ctgagtgtgc cgtcatttgt agatttaacg gcagctataa catcgtaaaa 1620
caagccagag atgaggtgag tccactgaca gggtgcaagg aagggcaccc ttttctattc 1680
tctggtgaaa gatccgacac ctcatgcctg aggcccccctt ccactagttg ggtaagaccg 1740

-continued gtaaaaatgg acgaggcgtc attggctgat agcttcgccc atggggttga caaggcaata 1800
atactaatca gaaaaggggc atcaggaata attaatttcc tagacactat tgggaggtgg 1860
ctaccggtag ctgaggcagc tatagtacca tattgtgaaa cttacactgt gacagggatg 1920
tatgtccatg tgaagaattg tctccctaga gggttaccga agcattcaaa gataatttcc 1980
ccgacaataa tatacttggg ggaaggtgac ccagcccata atattcagca cttatttggc 2040
tcaggtatag caaagtgggt cttagtccta ctcggggttc tgggtgagtg gtatggagaa 2100
ttggcctcta caatatactt actactagag tatgggtctg agtggttgga acatgaaagt 2160
ttggtcacgg aagggttgat ccctggcatc aatattacaa tagaactccc agctagtcat 2220
actgtacctg gttgggtgtg ggtcgcaggc cggtgggtat gcgtgaaacc agattggtgg 2280
cccacacaga tttggattga aactatagtg gcagaggtct ggcatatact aaaaatattg 2340
gcatcagccc tggtaaacat agtcactgca ttcgtaaacc tggaattggt atacctggtc 2400
ataatattag tcaaaatatc aaaggggaac ctgataggcg ctatattgtg gtgcctatta 2460
ctgtcagggg ctgaaggctc gtgccacaag agacaagact attacagtat ccagctagtc 2520
gttgacggaa aaacgggcgt agaaaaacga tctatagtgg gcaagtggac agtgataact 2580
agggaaggtc gggaaccaag attaatggag caaataagca tggtgtcaaa tgatagctta 2640
tcagaaactt actgctacaa taggctaaat actagcagtt gggggcgaca accggcaaga 2700
cagagagggt gtggtcaaac cgtacccttt tggcctggtg acaatgtcct ggaagaacaa 2760
tactatagca caggttactg ggtaaatgca acaggtggtt gccagttgag agaaggcgtg 2820
tggctatcaa gaaagggcaa tgtacagtgc cagcgtaacg gctcatcctt gatactgcaa 2880
ctggcgataa aagaagagaa tgacactatg gaaataccat gtgacccggt ggaaaccgaa 2940
agtatgggtc cagttacaca gggcacttgc gtgtacagct gggcattcgc cccaagaggg 3000
tggtattaca acaggaaaga tggttattgg ctccagtacg taaagaaaaa cgactaccag 3060
tactggacga aaatgcccac tgcttcatcc gccacaacga tgtaccgcca tttgctccct 3120
ttactggtgg cctgcctcat gggcggtaga atatcggtat ggattgtggc gatgctcctg 3180
tctttacagg tggaagctag tgaagtaggt accaagcaac tggctgtcac gctaactctg 3240
tggaaaatgg actggacaga attactcttc tatattgtta taatgctagc cgttaaggaa 3300
gaactcataa aaaaaatagt gactgcaagc cttgtggcct taaaaaatag tccagtagcc 3360
ttgagcttcc ttattgtact caggcttgtg gggggtagtg aggcactccc agtgggtttg 3420
ttattagaaa agatgtgcat agaccaaccg gagtttggaa ccccttcct gatctaccta 3480 tgggacaatt ggaagtggac tgtactagtc agcttctccg cactgaatca tgaaaaaact 3540
ataaaactgg caagaaaact gctgttggca acacacataa cagcgctcac attgactggt 3600
ctgagtgatt caatcttcta tatgatgctt ataatgacta atttattaat aaagacattc 3660
atatatctac tgggagccag tataaattgg gtcgagagag aaaaaaagaa gttgctagtg 3720
aagagaaaac taatatataa gaaagccgcg atttgcagtc aagatggaaa tgaattggag 3780
aataaattta ataagataac tgtaaatgcg gatttcaccc catgtaaact tgaacttctg 3840
caactactca gggctttttt agtctctcta tgcttttcct attacaagcc tctcctgtat 3900
gcggaaacta ctctaaccgt gatagtaatt ggcgtacagg agtacaacgt agctatggct 3960
cgcgggcgaa gcgtggtcca tagactgcta gccatggcct attacatata cggccgtata 4020
cagggtgaca tgttccagct cgccactatc cagtgcctgt tgtcaagtcc taggaaaatt 4080

-continued atgaaacaca tgatagaaaa tccaactctt aagaagctct ggcaaggtga aacagagctt 4140
tttaaccagg gtgtcagcca gtccaaaata gtgaatccaa agagcattgg gctggaagaa 4200
ttacacaagg gtatgtgcgg cctcccaact gtagtgcaaa atttggtcat atatgctaag 4260
aagaatgact ctcttatctt aggagagctg ggttaccccc ctggggacct caccagtgac 4320
gggtgggaaa ttttaggtcc tggcagaatc ccaaagatta ccaacgttga gtccgctaaa 4380
atggacttac tctccaagct tatgaccttt ctgggggttg agagctcaag agtccccagg 4440
accccagtcc actcgacaag gaaattattg aagatagtga gaggcttaga aactggatgg 4500
ggatacaccc atgcaggggg gataagtagc gcaaaacacg tcacaggtga aaaaaacttg 4560
atgactcaca tggaaggcag gaagggaaag tatatcctac aatcccaaga acatggtgct 4620
gatgaggtag aatatggagt gaaaactgac caaaaagcac ccgacaatgc cttatgctac 4680
tgctttaacc ctgaagccac aaacataaaa ggagaaacgg gagccatggt gtttatgaag 4740
aagataggaa aaaaatggac tctcgtgaca tcagatggta acaaagccta ttataatgta 4800
aacaacctga aagggtggtc cggactaccg ataatgttgc actctaccgg ggctatagta 4860
gggaggatta agtcagcgta ttcagatgaa aacgacttgg tagaggaact tatcgactcc 4920
aggactatca gcaagagcaa tgaggcaaac ctggatcacc ttatcaagga attagcagat 4980
atgcggaggg gggagtttcg ctccatcacc cttggaacag gagctgggaa aactacagaa 5040
ctgcccag 5048

<210> SEQ ID NO 21
<211> LENGTH: 5037
<212> TYPE: DNA
<213> ORGANISM: novel pestivirus

<400> SEQUENCE: 21
tgattggctg cattatgtat gggacatcct aaattgttgt gagccctgtg gtgagtgggg 60
gaaaggggtt aaccaggcct ctagtaccac aggcaccaac agacagggca actcgaacct 120
gagagagagg taccgagctc ttaagccccg agtacggggc agacgtcacc gagtagtaca 180
cccaaagacc accacttcta ggtgtagggt ctactgaggc tcgggtggac gtgggcgtgc 240
ccaaagagaa atcggtggtg ggcctggggg tcggggccac catgcccctt tatggggtag 300
accttactgc ttgatagagt gccggcggat gcctcgggta agagtataaa atccgttgtc 360
tattaacatg gaaaaacaga ttgcacatta cttaaaaaaa gaaaaacaaa ggaatgggtg 420
gacggaactg gtggtaggag aaagtcacac taaaataact acgctttctg gaaagaccta 480
tcgaggtact tgggaaatgg agaaacggcc aaatccttac ggaacctatt ttcccagacc 540
tagtccccag cagctcacag ccctacaccc ccacccagtg gtaaattgca aggtgataga 600
gtacaagggg acggacccta attatggtga ttgcccaaat acaaacgggg tgttcatcga 660
tgaaaagggt agaaggttga gcagccctcc attaggtatt tggaagataa gattggacta 720
cagcgacctg ataaatataa acagaccagt ccccactaga ggggaaaact cttatcgagt 780
cgagacctgc agtggggagc tggctactgt aatgctggta cacaataggg tacttgtgga 840
agactgtagg gggctatacc aatggaaacc caactgtgaa ggaattgtgc tctatgtaaa 900
aacttgttct gattgggcag atcaggtgga aaaacaggag aagggaagcc ccccaaaacc 960
acaacggcca ccaaggcgag acccacgaaa aggcttacaa ccacaagtcc ccagagaaac 1020
tgaggttacg gaaaagaaga ggcaacctag tgtcacctta gtagcagggg ggcagaaggc 1080
ccaaatcatc tacaaaggca ggactaaaaa taaaaagact ccggatgggg tctataagta 1140

-continued

```
cccaggagct aaagaagggg atgtggtaaa ggtcaggaag atgcttaaga attggcatat   1200
agccttgata atgtacctga tatatattat aactccaggt tttgccaagg ttcagtggtt   1260
cttaaaggac gaaaactcga cggggatcaa tcagatcctg tggcaaagac agattaacag   1320
aaccctgcat ggagaatggc ctaaccagat ctgccatggc atgccaaatg aaactattac   1380
agatgaggaa ttacgtagcc tgggaatgat agacacaagc cccagaacaa actacacttg   1440
ctgccagttg caatatcatg aatggaagaa acatggttgg tgcaactatc cacaaaaaca   1500
ggtctggatc aggaggataa cggccctaca agctaacctc accggagcct atgaggggcc   1560
tgagtgtgcc gtcatttgta gatttaacgg cagctataac atcgtaaaac aagccagaga   1620
tgaggtgagt ccactgacag ggtgcaagga agggcaccct tttctattct ctggtgaaag   1680
atccgacacc tcatgcctga ggcccccttc cactagttgg gtaagaccgg taaaaatgga   1740
cgaggcgtca ttggctgata gcttcgccca tggggttgac aaggcaataa tactaatcag   1800
aaaaggggca tcaggaataa ttaatttcct agacactatt gggaggtggc taccggtagc   1860
tgaggcagct atagtaccat attgtgaaac ttacactgtg acagggatgt atgtccatgt   1920
gaagaattgt ctccctagag ggttaccgaa gcattcaaag ataatttccc cgacaataat   1980
atacttgggg gaaggtgacc cagcccataa tattcagcac ttatttggct caggtatagc   2040
aaagtgggtc ttagtcctac tcggggttct gggtgagtgg tatggagaat tggcctctac   2100
aatatactta ctactagagt atgggtctga gtggttggaa catgaaagtc tggtcacgga   2160
agggttgatc cctggcatca atattacaat agaactccca gctagtcata ctgtacctgg   2220
ttgggtgtgg gtcgcaggcc ggtgggtatg cgtgaaacca gattggtggc ccacacagat   2280
ttggattgaa actatagtgg cagaggtctg gcatatacta aaaatattgg catcagccct   2340
ggtaaacata gtcactgcat tcgtaaacct ggaattggta tacctggtca taatattagt   2400
caaaatatca aaggggaacc tgataggcgc tatattgtgg tgcctattac tgtcaggggc   2460
tgaaggctcg tgccacaaga gacaagacta ttacagtatc cagctagtcg ttgacggaaa   2520
aacgggcgta gaaaaacgat ctatagtggg caagtggaca gtgataacta gggaaggtcg   2580
ggaaccaaga ttaatggagc aaataagcat ggtgtcaaat gatagcttat cagaaactta   2640
ctgctacaat aggctaaata ctagcagttg gggcgacaa ccggcaagac agagagggtg   2700
tggtcaaacc gtaccctttt ggcctggtga caatgtcctg gaagaacaat actatagcac   2760
aggttactgg gtaaatgcaa caggtggttg ccagttgaga gaaggcgtgt ggctatcaag   2820
aaagggcaat gtacagtgcc agcgtaacgg ctcatccttg atactgcaac tggcgataaa   2880
agaagagaat gacactatgg aaataccatg tgacccggtg gaaaccgaaa gtatgggtcc   2940
agttacacag ggcacttgcg tgtacagctg ggcattcgcc ccaagagggt ggtattacaa   3000
caggaaagat ggttattggc tccagtacgt aaagaaaaac gactaccagt actggacgaa   3060
aatgcccact gcttcatccg ccacaacgat gtaccgccat ttgctccctt tactggtggc   3120
ctgcctcatg ggcggtagaa tatcggtatg gattgtggcg atgctcctgt ctttacaggt   3180
ggaagctagt gaagtaggta ccaagcaact ggctgtcacg ctaactctgt ggaaaatgga   3240
ctggacagaa ttactcttct atattgttat aatgctagcc gttaaggaag aactcataaa   3300
aaaaatagtg actgcaagcc ttgtggcctt aaaaaatagt ccagtagcct tgagcttcct   3360
tattgtactc aggcttgtgg ggggtagtga ggcactccca gtgggtttgt tattagaaaa   3420
gatgtgcata gaccaaccgg agtttggaac ccctttcctg atctacctat gggacaattg   3480
```

-continued gaagtggact gtactagtca gcttctccgc actgaatcat gaaaaaacta taaaactggc 3540
aagaaaactg ctgttggcaa cacacataac agcgctcaca ttgactggtc tgagtgattc 3600
aatcttctat atgatgctta taatgactaa tttattaata aagacattca tatatctact 3660
gggagccagt ataaattggg tcgagagaga aaaaaagaag ttgctagtga agagaacact 3720
aatatataag aaagccgcga tttgcagtca agatggaaat gaattggaga ataaatttaa 3780
taagataacc gtaaatgcgg atttcacccc atgtaaactt gaacttctgc aactactcag 3840 ggcttttta gtctctctat gcttttccta ttacaagcct ctcctgtatg cggaaactac 3900
tctaaccgta atagtaattg gcgtacagga gtacaatgta gctatggctc gcgggcgaag 3960
cgtggtccat agactgctag ccatggccta ctacatatac ggccgtatac agggtgacat 4020
gttccagctc gccactatcc agtgcctgtt gtcaagtcct aggaaaatta tgaaacacat 4080
gatagaaaat ccaactctta agaagctctg gcaaggtgaa acagagcttt ttaaccaggg 4140
tgtcagccag tccaaaatag tgaatccaaa gagtattggg ctggaagaat tacacaaggg 4200
tatgtgcggc ctcccaactg tagtgcaaaa tttggtcata tatgctaaga agaatgactc 4260
tcttatctta ggagagctgg gttacccccc tggggacctc accagtgacg ggtgggaaat 4320
tttaggtcct ggcagaatcc caaagattac caacgttgag tccgctaaaa tggacttact 4380
ctccaagctt atgacctttc tgggggttga gagctcaaga gtccccagga ccccagtcca 4440
ctcgacaagg aaattattga agatagtgag aggcttagaa actggatggg gatacaccca 4500
tgcagggggg ataagtagcg caaaaacacgt cacaggtgaa aaaaacttga tgactcacat 4560
ggaaggcagg aagggaaagt atatcctaca atcccaagaa catggtgctg atgaggtaga 4620
atatggagtg aaaactgacc aaaaagcacc cgacaatgcc ttatgctact gctttaaccc 4680
tgaagccaca aacataaaag gagaaacggg agccatggtg tttatgaaga agataggaaa 4740
aaaatggact ctcgtaacat cagatggtaa caaagcttat tataatgtaa acaacctgaa 4800
agggtggtcc ggactaccga taatgttgca ctctaccggg gctatagtag ggaggattaa 4860
gtcagcgtat tcagatgaaa atgacttggt agaggaactt atcgactcca ggactatcag 4920
caagagcaat gaggcaaacc tggatcacct tatcaaggaa ttagcagata tgcggagggg 4980
ggagtttcgc tccatcaccc ttggaacagg agctgggaaa actacagaac tgcccag 5037

<210> SEQ ID NO 22
<211> LENGTH: 5039
<212> TYPE: DNA
<213> ORGANISM: novel pestivirus

<400> SEQUENCE: 22
gcataatgct ttgattggct gcattatgta tgggacatcc taaattgttg tgagccctgt 60
ggtgagtggg ggaaaggggt taaccaggcc tctagtacca caggcaccaa cagacagggc 120
aactcgaacc tgagagagag gtaccgagct cttaagcccc gagtacgggg cagacgtcac 180
cgagtagtac acccaaagac caccacttct aggtgtaggg tctactgagg ctcgggtgga 240
cgtgggcgtg cccaaagaga aatcggtggt gggcctgggg gtcggggcca ccatgcccct 300
ttatggggta gaccttactg cttgatagag tgccggcgga tgcctcgggt aagagtataa 360
aatccgttgt ctattaacat ggaaaaacag attgcatatt acttaaaaaa agaaaaacaa 420
aggaatgggt ggacggaact ggtggtagga gaaagtcaca ctaaaataac tacgctttct 480
ggaaagacct atcgaggtac ttgggaaatg gagaaacggc caaatcctta cggaacctat 540
tttcccagac ctagtcccca gcagctcaca gccctacacc cccacccagt ggtaaattgc 600
aaggtgatag agtacaaggg gacggaccct aattatggtg attgcccaaa tacaaacggg 660
gtgttcatcg atgaaaaggg tagaaggttg agcagccctc cattaggtat ttggaagata 720
agattggact acagcgacct gatcaatata aacagaccag tccccactag tggggaaaac 780
tcttatcgag tcgagacctg cagtggggag ctggctactg taatgccggt acacaatagg 840
gtacttgtgg aagactgtag gggcctatac caatggaaac ccaactgtga aggaattgtg 900
ctctacgtaa aaacttgttc tgattgggca gatcaggtgg aaaaacagga gaagggaagc 960
cccccaaaac cacaacggcc accaaggcga gacccacgaa aggcttaca accacaagtc 1020
cccagagaaa ctgaggttac agaaaagaag aggcaaccta gtgttacctt agtagcaggg 1080
gggcagaagg cccaaatcat ctacaaaggc aggactaaaa ataaaaagac tccggatggg 1140
gtctataagt acccaggagc taaagaaggg gatgtggtaa aggtcaggaa gatgcttaag 1200
aattggcata tagccttagt aatgtacctg atatatatta taactccagg ttttgccaag 1260
gttcagtggt tcttaaagga cgaaaactcg acggggatca atcagatcct gtggcaaaga 1320
cagattaaca gaaccctgca tggagaatgg cctaaccaga tctgccacgg catgccaaat 1380
gaaactatta cggatgagga attacgtagc ctgggaatga tagacacaag ccccagaaca 1440
aactacactt gctgccagtt gcaatatcat gaatggaaga aacatggttg gtgcaactat 1500
ccacaaaaac aggtctggat caggagaata acggccctac aagctaacct caccggagcc 1560
tatgaggggc ctgagtgtgc cgtcatttgt agatttaacg gcagctataa catcgtaaaa 1620
caggccagag atgaggtgag tccactgaca gggtgcaagg aagggcaccc ttttctattc 1680
tctggtgaaa gatccgacac ctcatgcctg aggcccccctt ccactagttg ggtaagaccg 1740
gtaaaaatgg acgaggtgtc attggctgat ggcttcgccc atggggttga caaggcaata 1800
atactaatca gaaaaggggc atcaggaata attaatttcc tagacactat tgggaggtgg 1860
ctaccggtag ctgaggcagc tatagtacca tattgtgaaa cttacactgt gacagggatg 1920
tatgtccatg tgaagaattg tctccctaga gggttaccga agcattcaaa aataatttcc 1980
ccgacaatga tatacttggg ggaaggtgac ccagcccata atattcagca cttatttggc 2040
tcaggtatag caaagtgggt cttagtccta ctcggggttc tgggtgagtg gtatggagaa 2100
ttggcctcta caatatactt actactagag tatgggtctg agtggttgga acatgaaagt 2160
ctggtcacgg aagggttgat ccctggcatc aatattacaa tagaactccc agctagtcat 2220
actgtacctg gttgggtgtg ggtcgcaggc cggtgggtat gcgtgaaacc agactggtgg 2280
cccacacaga tttggattga aactatggtg gcagaggtct ggcatatact aaaaatattg 2340
gcatcagccc tggtaaacat agtcactgca ttcgtaaacc tggaattggt atacctggtc 2400
ataaatattag tcaaaatatc aaaggggaac ctgataggcg ctatattgtg gtgcctatta 2460
ctgtcagggg ctgaaggctc gtgccacaag agacaagact attacagtat ccagctagtc 2520
gttgaagaaa aaacgggcgt agaaaaacga tctataatgg gcaagtggac agtgataact 2580
agggaaggtc gggaaccaag attaatggag caaataagta tggtgtcaaa tgatagcttg 2640
tcagaaactt actgctacaa taggctaaat actagcagtt gggggcgaca accggcaaga 2700
cagagagggt gtggtcaaac cgtacccttt tggcctggtg acaatgtcct ggaagaacaa 2760
tactatagca caggttactg ggtaaatgca acaggtggtt gccagttgag agaaggcgtg 2820
tggctatcaa gaaagggcaa tgtacagtgc cagcgtaacg gctcatcctt gatactgcaa 2880
ctggcgataa aagaagagaa tgatactatg gaaataccat gtgacccggt ggaaaccgaa 2940

-continued

```
agtatgggtc cagttgcaca gggcacttgc gtgtacagct gggcattcgc cccaagaggg   3000

tggtattaca acaggaaaga tggttattgg ctccagtacg taaagaaaaa cgactaccag   3060

tactggacga aaatgcccac tgcttcatcc gccgcaacga tgtaccgcca tttgctccct   3120

ttactggtgg cctgccttat gggcggtaga atatcggtat ggattgtggc gatgctcctg   3180

tctttacagg tggaagctag tgaagtaggt accaagcaac tggctgtcac gctaactctg   3240

tggaaaatgg actggacaga attactcttc tatattgtta taatgctagc cgttaaggaa   3300

gaactcataa aaaaaatagt gactgcaagc cttgtggcct taaaaaatag tccagtagcc   3360

ttgagcttcc ttattgtact caggcttgtg gggggtagtg aagcactccc agtgggtttg   3420

ctattagaaa agatgtgcat agaccaaccg gagtttggaa ccccttttcct gatctaccta   3480

tgggacaatt ggaagtggac tgtactagtc agcttctccg cactgaatca tgaaaaaact   3540

ataaaactgg caagaaaact gctgttggca acacacataa cggcgctcac attgactggt   3600

ctgagtgatt caatcttcta tatgatgctt ataatgacta atttattaat aaagacattc   3660

atatatctac tgggagccag tatgaattgg gtcgagagag aaaaaaagaa gttgctagtg   3720

aagagaaaac taatatataa gaaagccgcg atttgcagtc aagatggaaa tgaattggag   3780

aataaattta ataagataac tgtaaatgcg gatttcaccc catgtaaact tgaacttctg   3840

caactactca gggctttttt agtctctcta tgcttttcct attacaagcc tctcctgtat   3900

gcggaaacta ctctaaccgt aatagtaatt ggcgtacagg agtacaacgt agctatggct   3960

cgcgggcgaa gcctggtcca tagactgcta gccatggcct actacatata cggccgtata   4020

cagggtgaca tgttccagct cgccactatc cagtgcctgt tgtcaagtcc taggaaaatt   4080

atgaaacaca tgatagaaaa tccaactctt aagaagctct ggcaaggtga aacagagctt   4140

tttaaccagg gtgtcagcca gtccaaagta gtgaatccaa agagcattgg gctggaagaa   4200

ttacacaagg gtatgtgcgg cctcccaact gtagtgcaaa atttggtcat atatgctaag   4260

aagaatgact ctcttatctt aggagagctg ggttaccccc ctggggacct caccagtgac   4320

gggtgggaaa ttttaggtcc tggcagaatc ccaaagatta ccaacgttga gtccgctaaa   4380

atggacttac tctccaagct tatgaccttt ctgggggttg agagctcaag agtccccagg   4440

actccagtcc actcgacaag gaaattattg aagatagtga gaggcttaga aactggatgg   4500

ggatacaccc atgcaggggg gataagtagc gcaaaacacg tcacaggtga aaaaaacttg   4560

atgactcaca tggaaggcag gaagggaaag tatatcctac aatcccaaga acatggtgct   4620

gatgaggtag aatatggagt gaaaactgac caaaaagcac ccgacaatgc cttatgctat   4680

tgctttaacc ctgaagccac aaacataaaa ggagaaacgg gagccatggt gtttatgaag   4740

aagataggaa aaaaatggac tctcgtaaca tcagatggta acaaagccta ttataatgta   4800

aacaacctga aagggtggtc cggactaccg ataatgttgc actctaccgg ggctatagta   4860

gggaggatta agtcagcgta ttcagatgaa aacgacttgg tagaggaact tatcgactcc   4920

aggactatca gcaagagcaa tgaggcaaac ctggatcacc ttatcaagga attagcagat   4980

atgcggaggg gggagtttcg ctccatcacc cttggaacag gagctgggaa aactacaga    5039
```

```
<210> SEQ ID NO 23
<211> LENGTH: 5035
<212> TYPE: DNA
<213> ORGANISM: novel pestivirus

<400> SEQUENCE: 23

cataatgctt tgattggctg cattatgtat gggacatcct aaattgttgt gagccctgtg     60
```

-continued

```
gtgagtgggg gaaaggggtt aaccaggcct ctagtaccac aggcaccaac agacagggca    120
actcgaacct gagagagagg taccgaactc ttaagtcccg agtacggggc agacgtcact    180
gagtagtaca cccaaagacc accacttcta ggtgtagggt ctactgaggc tcaggtggac    240
gtgggcgtgc ccaaagagaa atcggtggcg gacctggggg tcgggtccac catgcccctt    300
tagggggtag accttactgc ttgatagagt gccggcggat gcctcgggta agagtataaa    360
atccgttgtt tgttaacatg gaaaaacaga ttgcatatta cttaaaaaaa gaaaaacaaa    420
gaaatgggtg gacggaattg gtggtaggag aaagccatac aaaaataacc acactctctg    480
gaaagaccta tcgaggcact tgggaaatgg agaaacggtc gaatccttac ggaacctatc    540
tccccagacc tagtcctcga cagcttacag ccctacaccc ccacccagtg gtgaattgta    600
aggtgactga gtacaaagag ctagacccta attatggtga ctgcccaaat acaaacgggg    660
tgttcatcga cgaaaagggt agaaggctga gcagccctcc attgggcatt tggaaaataa    720
gactggacta cagcgacctg gtaaatataa acaaaccagc ctccgctagt ggaaaaaact    780
cttatcgagt cgagacctgt agtggggagc tggctactgt aacaccagta cacgacagag    840
tgcttgtaga agactgcagg gggctatacc aatggaaacc caattgtgaa ggaatggtgc    900
tctatgtgaa aacttgttct gattgggcag accaggtaga aaaacaggag aaggaaagcc    960
ccccaaaacc ccagcgacca ccgaggcgag acccacgaaa aggattacaa ccacaagtcc   1020
ccaaagagac tgaggtcaca gaaaagaaga gacaacccag cgttacctta gtatcggggg   1080
ggcagaaggc ccaagtcatc tacaagggca agactaagaa taaaaagact ccggatggag   1140
tctataagta tccaggagcc agagaagggg atgtagtaaa ggttaggaag atgctgaaga   1200
attggcatat agctgtagtg atgtacctga tttatatcat aaccccgagc tttgccaagg   1260
ttcagtggtt cttaaaggat gaaaactcga cggggatcaa ccagatactg tggcaaagac   1320
agatcaatag atccctgcat ggagaatggc ccaaccagat ctgccacggc atgccgaacg   1380
aaaccatcac ggatgaagaa ttacgcagtc tgggaatgat tgacacaagc cccagaacaa   1440
actatacttg ctgccagttg caatatcatg aatggaagaa acatggttgg tgcaactatc   1500
cacaaaaaca gacttggatt aggaggataa cggccctaca aactaacctc accggagctt   1560
atgagggacc tgagtgcgct gttatttgtc gatttaatgg cagctataac atcgtaaaac   1620
aggccagaga cgaggtgagt ccactgacag ggtgtaagga agggcaccct ttcctatttt   1680
ctggtgaaag atccgatacc tcatgcctga ggcctccttc cacaagttgg gtaagaccag   1740
tgaagatgga tgaggcatca atagccgatg gctttgccca tggggttgac aaggcgataa   1800
tactgattag aaaaggggca tcaggaatca ttaatttcct agacaccatt gggaggtggc   1860
taccggtagc cgaagcaact atagtaccat attgtgaaac ttacactgtg acagggatgt   1920
atgtccatgt gaagaattgc ctccctagag ggttacctaa gcattcaaaa ataatttccc   1980
caacaatgat atacctgggg gaaggtgacc cagctcataa catccaacac ttatttggct   2040
caggtatagc aaagtgggtt ctagtcttac tcggggtcct gggtgagtgg tatggagaat   2100
tggcttctac aatataccta ctgctagagt atgggtctga gtggttggaa catgaaagcc   2160
tgaccacgga agggttgatc cccggcatta atatcacaac agaactccca gctagtcata   2220
cagtgcctgg ctgggtgtgg gtcgcaggcc agtgggtgtg tgtgaagcca gactggtggc   2280
ctacacagat ttggattgaa accgtggtgg cggaggcctg gcatatacta aaaatattgg   2340
catcagccct ggtgaacata gtcactgcat ttgtaaacct agaactggtc tacttggtca   2400
```

-continued

```
taatattggt caaaatatca aaggggaacc tgataggcgc catattatgg tgcctattgt   2460
tgtcaggggc tgaaggctcg tgccacaaaa gacaagatta ttataaatatc cagctggttg  2520
tcgaagaaaa gacaggtgta gaaaaacgat ctataatggg caaatggact gtgataacta   2580
gggaaggccg ggaaccaaga ttaatggagc aaataaatat ggtgtcaaat gatacactgt   2640
cagaaactta ctgctataat aggctaaaca ccagtagttg gggcggcaa ccagtaagac    2700
agagagggtg tggtcagacc gtgccctatt ggcctggtga taatatcctg gaagaacaat   2760
actatagcac aggttactgg gtgaacgcga caggcggttg ccagctgaga gaaggtgtgt   2820
ggctgtcaag aaagggtaat gtacagtgcc agcgtaacgg ctcatccttg atactgcaat   2880
tagcgataaa agaagaaaat gacactatgg aaataccatg tgacccggtg gaaacagaaa   2940
gcatgggtcc ggtcgcacag ggcacttgcg tgtatagctg ggcattcgcc ccaagagggt   3000
ggtattacaa taggaaagat ggctattggc tccagtacat aaagaaaaac gactaccagt   3060
actggacaaa aatgcctacc acctcgtccg ctgcgacaat gtaccgccac ttgcttcccc   3120
tactggtggc ttgccttatg ggcggcagga tatcggtgtg gattgtagca atgctcctat   3180
ctctgcaggt ggaagctagc gaagtaggta ccaagcaact ggctgtcaca ctaacactgt   3240
ggaaaatgga ctggatagaa ctactcttct atattatcat aatgctagcc gtcaaggaag   3300
aacttataaa gaaaatagtg actgcaagcc tagtggcctt aaaaaatagt ccagtggctt   3360
tgagctttct tgttgtactc aggcttgtag gggcagtga agcactccca gtgggattac    3420
tattagaaaa gatgtgcata gaccaaccgg agtttggaac ccctttcctg atctacctgt   3480
gggacaattg gaagtggact gtattagtca gtttctccgc actgaaccat gaaaaaacta   3540
taaaactggc aagaaaactg ctattggcca cacatataac agcgctcata ctgactggtc   3600
tgagtgattc aatcttctac atgatgctta taataaccaa cctactggta aagacattca   3660
tatatttact gggggccagc atgaattggg tcgagaaaga aaaaaagaag ttgctggtaa   3720
agaggaaatt aatatataag aaagccgcga tttgcagtca ggatgagaat gaattggaga   3780
ataaattcaa taggatcact gtaaatgcgg atttcacccc atgcaaactt gaacttttac   3840
aactgcttag ggctttttta gtctctctat gcttttccta ttacaagcct ctcctgtatg   3900
cagagaccac tctaactgtc atagtaattg gcgtacaaga gtacaacgta gcaatggccc   3960
gcgggcggag tttggtccat agactactag ccatggccta ctacatatat ggccgcatgc   4020
agggtgacat gttccaactc gccaccattc agtgcctgtt gtcaagcccg aggaaaatta   4080
tgaaacatat gatagaaaat ccgactctta agaagctatg gcaaggcgaa acagaacttt   4140
ttaaccaggg tgtcaaccag tccaagatag tgaacccaag gaaaattggg ttggaggaat   4200
tacataaggg catgtgcggc ctcccaaccg tagtgcaaaa tttggtcata tatgcaaaga   4260
agaacgactc tcttatttta ggagagttgg gttactcccc tggggacctc accagcgatg   4320
ggtgggaaat tttaggccct ggcagaatcc caaagatcac taatgttgag tctgctaaaa   4380
tggacttact ttccaaactc atgaccttcc tggggattga aagctcaagg gtccccagaa   4440
ccccagtcca ctcaacaagg aaattattga agatagtaag aggcctggaa actggatggg   4500
ggtacaccca cgcaggagga attagcagcg cgaaacatgt tacaggtgaa aagaacttga   4560
tgacccacat ggagggcagg aagggtaagt atatcctaca atcccaagaa catggtgctg   4620
atgaggtaga atatggagta aaaactgacc aaaaagcgcc cgacaatgcc ttgtgctatt   4680
gctttaaccc tgaagctaca aacataaaag gtgaaacagg ggccatggtg ttcatgaaga   4740
agataggaaa aaaatggact ctcgtgacat cagatggtaa caaagcctat tataatgtaa   4800
```

-continued ataatctgaa agggtggtct ggactaccaa taatgttgca ctccaccggg gccatagtag 4860
ggaggattaa gtcagcatat tcagatgaaa atgacttggt ggaggaactt atcgattcta 4920
ggactatcag caagagtaat gaggcaaacc tggaccacct tatcaaggaa ttggccgata 4980
tgcggagggg ggagttccgc tcaattaccc ttggaacggg agccgggaaa actac 5035

<210> SEQ ID NO 24
<211> LENGTH: 4921
<212> TYPE: DNA
<213> ORGANISM: novel pestivirus

<400> SEQUENCE: 24
tgattggctg cattatgtat gggacatctt aaattgctat gagccccgtg gtgagtgggg 60
gaaaggggtt aaccaggcct ctaggtccac aggcaccgat agacggggca actcaagcct 120
gagagagagg taccgaactc ttaagtcccg agtacggggc agacgtcacc gagtagtaca 180
cccaacgacc accacttcta ggtgtagggt ctactgaggc tcgggtggac gtgggcgcgc 240
ccaaagagaa atcggtggtg gacctggggg tcggggccac catgcccctt tacggggtag 300
accttactgc ttgatagagt gccggcggat gcctcaggta agagtataaa atccgttgtc 360
tattaacatg gaaaagcaga tcacatatta cttaaaaaaa gaaaaacaaa caaatggatg 420
gacggaatta gtggtaggag aaagtaatac gaaaataacc acgctctctg gaaaaaccta 480
ccgaggtact tgggaaatgg agaaacggcc gaatccctac ggaacctatc tccccagacc 540
tagtccccaa cagcttacag ccctacaccc ccacccagta gtgaattgca aggtgattga 600
atacaaggat aaggacccta attatggtga ttgcccaaat acaaatgggg tgttcatcga 660
cgaaaaaggc agaaggctga gcagccctcc attgggtatt tggaagataa ggttggacta 720
cagcgacctg gtgaatataa acagaccaat ccccgctggt ggaaaaaact tctaccgagt 780
tgagacctgt agtggggagc tggctactgt gacactggta cacaaaagag tacttgtgga 840
agaccgtagg ggattgtacc aatggaaacc caactgtgaa gggatggtgc tctatgtgaa 900
aacttgttct gattgggcag atcaggtgga aaaacaggag aaggaaagcc ccccaaaacc 960
tcagcgacca ccaaggcgag atccccgaag agggttacaa ccacaagtcc ccaaagagac 1020
tgaggtcact gaaaagaaga gacaacccag tgtcacctta gtatcggggg ggcagaaggc 1080
ccaagtcatc tacaaaggca ggactaagaa caaaaagact ccggacgggg tctataagta 1140
tccgggggct aaagaggggg atgtgataaa ggtcaggaag atgctgaaga attggcacgt 1200
agctctggta atgtatctaa tatatatcat aaccccaggc ttcgccaagg ttcagtggtt 1260
cttaaaagat gaaaactcaa cggggatcag tcagatactg tggcgaagac agatcaacag 1320
atctctgcat ggagaatggc ctaatcagat ctgccacggt atgccaaatg aaactattac 1380
ggacgaggaa ttacgcagcc tgggaatgat agatacaagc cccagaacga actacacttg 1440
ttgccagttg caatatcatg agtggaagaa acatggttgg tgtaactatc cacaaaaaca 1500
ggcttggatt aggaggataa cggccttaca agccaacctc accggagctt acgcgggacc 1560
tgagtgcgct gtcatctgtc gatttaacgg tagctataac atcgtaaagc aagccagaga 1620
tgaggtaagt ccactgacag ggtgtaagga agggcacccc ttcctattct ctgacgaaag 1680
atccgacacc tcatgcctga ggcctccttc cactagctgg gtaagaccag taaaaatgga 1740
cgaggcatca attgccgatg gctttgccca tggggttgac aaggcaataa tactgatcag 1800
aaaaggggca actggaatta ttaatttcct agatactatc gggaggtggc taccggtagc 1860

-continued

```
tgaagcaacc ataacaccat attgtgaaac ttataccgtc acagggatgt atgtccatgt   1920
gaagaattgc ctccccaaag ggttacctaa gcattcaaaa ataatttccc caacgatgat   1980
atatctgggg gaaggtgacc cagcccataa tattcagcac ctgtttggct caggtatagc   2040
aaagtgggtt ctagtcttac tcggggttct gggtgagtgg tatggagaat tggcttctac   2100
gatataccta ctactagagt atgggtctga gtggttggaa catgaaagtc tgaccacgga   2160
agggttgatc cctggcatca acatcacaat agaactccca gccagtcaca cagtgcctgg   2220
ttgggtgtgg gtcgcaggcc agtgggtatg cgtgaagcca gactggtggc ctacacagat   2280
ctggatcgaa actatggtgg cggaggcctg gcatatacta aaaatattgg catcagccct   2340
ggtgaacata gtaactgcat ttgtgaacct ggaattagtc tacctggtca taatactagt   2400
taaaatatca aaggggaacc tgattggtgc catactatgg tgcctgttac tatcaggggc   2460
tgaaggctct tgccacaaaa gacaagacta ttacaatgtc cagctgatcg tcgatgaaaa   2520
gacaggcgta gaaagacgat ctataatggg caagtggact gtgataacca gggaaggcag   2580
ggaaccaaga ttaatggagc aaataaacat ggtgtcaaat gacagcctgt cagagactta   2640
ctgctataat aggctaaata ccagcagttg gaggcggcaa ccggcaaaac agagagggtg   2700
tggtcaaact gtgccctatt ggcctggcga caatgtctta gaagaacaat actatagtac   2760
agggtattgg gtgaacgtga caggcggttg tcagctgaga gaaggcgtgt ggctatcaag   2820
aaagggcaat gtacagtgcc agcgtaacgg ctcagccttg atgctgcaat tggcgataaa   2880
agaagaaaat gacactatgg aaataccgtg tgacccggtg gaaacagaaa gcatgggtcc   2940
agttgcacaa ggcacttgcg tgtatagctg ggcatttgcc ccaagagggt ggtactataa   3000
taagaaagat ggttactggc tccaatacat aaagaaaaac gactaccagt actggacaaa   3060
aatgcctgct gcctcgtccg ccgcaacgat gtaccgccat ttgcttccct tactagtggc   3120
ctgcctgatg ggcggcagga tatcggtgtg gattgtggcg atgctcctgt ctttgcaggt   3180
ggaagccagc gaagtgggta ctaagcaact ggctgtcact ctaaccctgt ggaaaatgga   3240
ctggacggaa ctgcttttct atgttgtcat aatgctagcc gttaaggaag agcttgttaa   3300
gaaaatagtg accgcaagcc ttgtggccct aaaaaacagt ccagtagctt tgagctttct   3360
tattgttctc aggcttgtgg ggggcagtga agcactccca gtaggtttac tattagaaaa   3420
gatgtgcata gaccaaccgg agttcggaac ccctttcctg atctacctgt gggacaattg   3480
gaagtggact gtactagtca gcttctctgc actgaatcat gaaaaaacta taaaactggc   3540
aagaaaactg ttattggcaa cacatataac agcgctcaca ctgaccggtc tgagtgattc   3600
aatcttttat gtgatgctta taatgaccaa cctactaata aagacattta tatatctact   3660
gggggctagt atgaattggg tcgagagaga aaagaagaag ttgctagtaa agaggaaact   3720
aatatataag aaagctgcaa tttgcaatca agatgagaat gaattggaga ataaatttaa   3780
caagataacc gtaaatgcgg acttcacccc atgtaaactt gaactcttac aactactcag   3840
ggctttttta gtctctttat gtttttccta ttacaagccc ctcctgtatg cagagaccac   3900
cctaactgtt atagtgattg gcgtacaaga gtacaatgtg gctatggccc gcgggcgaag   3960
cgtgattcat agattgctag ccatggccta ctacgtatac ggccgcatgc agggtgacat   4020
gtttcagctc gccaccatcc agtgcctgtt gtcgagtccg aggaaagtta tgaaacacat   4080
gatagaaaac ccaactctca agaagctctg gcaaggcgaa acagaacttt ttaaccaggg   4140
tgtcagccaa tccaaaatag tgaacccaaa gaagattggg ctagaggaat tacataaggg   4200
catgtgcggc ctcccaactg tagtgcaaaa tttggtcata tatgcgaaga agaatgactc   4260
```

```
tcttatctta ggagagttag gttacccccc cggggacctc actagtgatg ggtgggaaat   4320

actaggtcct ggcagaatcc caaagatcac taacgtcgag tctgctaaaa tggacttgct   4380

ctccaaactt atgacctttc tggggatcga aagctcaagg gtccccagga ctccaatcca   4440

cccaacaagg aaattactga agatagtaag aggcctggaa actggatggg ggtatactca   4500

tgcaggggga ataagcagcg caaaacatgt tacaggtgaa aaaaacttga tgacccacat   4560

ggagggccgg aagggcaagt atatcctaca atcccaagaa cacggtgccg atgaggtaga   4620

atatggagta aaaactgatc aaaaagcacc cgacaatgcc ttatgctact gctttaaccc   4680

tgaagccaca aatataaaag gagaaacggg agccatggta ttcatgaaga agataggaaa   4740

aaaatggact ctcgtaacat cagatggtaa caaggcctat tataatgtga acaacctgaa   4800

agggtggtct ggactaccga taatgttgca ctctactggg gccatagtag gaggataaag   4860

tcagcatatt cagatgaaaa cgacttggtg gaggaactta ttgactctag gactatcagc   4920

a                                                                   4921
```

```
<210> SEQ ID NO 25
<211> LENGTH: 4702
<212> TYPE: DNA
<213> ORGANISM: novel pestivirus

<400> SEQUENCE: 25

gagtacgggg cagacgtcac tgagtagtac acccaaagac caccactttt aggtgtaggg     60

tctactgagg ctcaggtgga cgtgggcgtg cccaaagaga aatcggtggt gaacctgggg    120

gtcgggttca ccatgcccct ttagggggta gaccttactg cttgatagag tgccggcgga    180

tgcctcgggt aagagtataa aatccgttgt acattaacat ggaaaaacag attgcatatt    240

atttaaaaaa agaaaaacaa agaaatgggt ggacggaact ggtagtagga gaaagctata    300

caaaaataac cacgctctct gggcggacct atcgaggtac ctgggaaatg gagaaacggc    360

cgaatcctta cggaacctac ctacccaagc ccagtcctca acagcttaca gccctacacc    420

cccacccagt agtgaattgt aaggtgactg agtacaaaga gctggaccct aattatggtg    480

attgcccgag cacaaatggg gtgttcatcg acgaaaaggg tagaaggctg agtggccctc    540

cattgggtat ttggaagata agactggact acagcgacct ggtaaatatg aacagaccag    600

cccccgctag taaaaaaaac tcgtatcgag tcgagacctg cagtggggag ctggctattg    660

tgacaccggt acacgatagg gtacttgtgg aggactgcag gggctatat caatggaaac    720

ccaactgtga aggaatggtg ctctatgtga aaacttgttc tgattgggca gatcaggtgg    780

aaaaacagga gaaggaaagc cccccaaaac ctcagcgacc accgaggcga gacccacgga    840

aagggttaca accacaagtc cccaaagaga ctgaggtcac agaaaagaag agacaaccta    900

gcgttacctt agtatcgggg gggcagaagg cccaagtcat ctacaaaggc aagactaaga    960

ataaaaagac cccggatgga gtctataaat atccaggagc cagacaaggg gatgtagtaa   1020

aagttaggaa gatgctgaag aattggcata tagcagtagt actatgcctg atttacatca   1080

taaccccaag ccttgccaag gttcagtggt tcctaaagga tgaaaactcg acggggatta   1140

accaggtact gtggcgaaga cagatcaata gatctctgca tggagaatgg cccaaccagg   1200

tctgccacgg tatgccaaat gaaaccatca cagatgagga attgcgcagc ctgggaatga   1260

tagatacaag ccccaaaaca aactatactt gttgccagtt gcaatatcat gagtggaaga   1320

aacatggctg gtgcaactat ccacaaaaac agacttggat taggaggata atggccctac   1380
```

-continued

```
aagccaacct caccggagct tatgagggac ctgagtgcgc tgttatctgt cgattcaacg   1440
gcagttataa catcgtaaaa caggccagag acgaagtaag tccactgacg gggtgcaagg   1500
aagggcaccc tttcctattt tccggtgaaa aatccggctc ctcatgcctg aggcctcctt   1560
ccactagttg ggtaaggcca gtgaagatgg atgaggcatc aatagctgat ggctttgccc   1620
atggggttga caaagcaata atactaatta gaaaaggggc atcaggaatt ataaatttcc   1680
tagacactat tgggaggtgg ctacctgtag ccgaagcagc tatagtacca tattgtgaaa   1740
cttacactgt gacagggatg tatgtccatg tgaggaattg cctccctaga gggttaccca   1800
agcattcaaa aataatttcc ccgacgttaa tatacctagg ggaaggtgac ccagcccata   1860
acatccagca cttatttggc tcaggtatag caaagtgggt tctagtctta ctcggggtcc   1920
tgggtgagtg gtatggagaa ttggcttcta caatatatct actactagag tatgggtctg   1980
agtggttgga acatgaaaac ctgatcacgg aagggttgat ccctggcatt aatatcacaa   2040
tagaactccc agctagtcat acagtgcctg gttgggtgtg ggttgcaggc caatgggtgt   2100
gtgtgaagcc agactggtgg cctacacaga tttggattga aaccatggta gcagaggcct   2160
ggcatatact aaaaatacta gcatcagccc tggtgaacat agtcactgca tttataaacc   2220
tggaattggt ctacctggtc ataatactag tcaaagtatc aaaggggaac ctgataggcg   2280
ccatactatg gtgcctatta ctgtcagggg ctgaaggctc atgccacaaa agagaagatt   2340
attacaatat ccagctagtt gttgaagaaa aaacaggtgt ggaaaaacga tctgtaatgg   2400
gcaaatggac tgtggtatcc agggaaggtc aggaaccaag gttaatggag caaataaata   2460
tggtgtcaaa tgataggctg tcagaaactt actgctacaa taggctaaat accagtagtt   2520
ggggacggca accggcaaga cagagagggt gtggtcagat tgtgccctat tggcctggtg   2580
acaatgtcct agaggaacaa tactatagca caggttactg ggtgaacgca acaggcggtt   2640
gccagctgag agaaggcgtg tggctatcaa gaaagggcaa tgtacagtgc cagcgtaacg   2700
gctcatcctt aacactgcaa ttagcgataa aagaagagaa tgacactatg gaaataccat   2760
gtgacccggt ggaaacagaa agcatgggtc cagtagcaca gggcacttgc gtgtatagct   2820
gggcattcgc cccaagaggg tggtattata ataggaaaga cggttattgg cttcagtaca   2880
taaagaaaaa cgactaccag tactggacaa aaatgcctac tgcctcgtcc gctgcaacga   2940
tgtaccgcca tttacttccc ttactggtgg cctgccttat gggcggcaga atatcggtgt   3000
ggattgtggc aatgctccta tctctacagg tggaagctag cgaagtaggc accaagcaac   3060
tggctgtcac actaactctg tggaaaatgg actggacaga actactcttc tatatcgtta   3120
taatgttagc cgtcaaggaa gaactcataa agaaaatagt gactgcaagc ctagtggcct   3180
taaaaaatag tccagtagcc ttgagctttc ttattgtact caggcttgta gggggcagtg   3240
aagcactccc agtgggttta ctattagaaa agatgtgcat agaccaaccg gagttcggaa   3300
cccctttcct gatctacctg tgggacaatt ggaagtggac tgtactagtc agcttctccg   3360
cactgaacca tgaaaaaact atcaaactgg caagaaaact gctattggcc acacatataa   3420
cagcgctcac attgactggt ctgagtgatt caatctttta catgatgctt ataatgacca   3480
acttactaat aaagacattc atatatctac tgggggccag cataaattgg gtcgagaaag   3540
aaaaaaagaa gctgctggta aagaggaaat taatatataa gaaagccgca atttgtagtc   3600
aggatgagaa tgaactggag aataaattca acaggataac tataaatgcg gatttcaccc   3660
catgcaaact tgaactttta caactactca gggctttttt agtctctata tgtttttcat   3720
attataagcc tctcctgtat gcagagacca ccttaactgt aatagtaatt ggtgtacaag   3780
```

-continued

```
agtacaatgt agcaatggcc cgcgggcgaa gcgtagtcca tagactacta gctatggcct   3840

actacatata tggccgcata cagggtgaca tgttccaact tgccactatt cagtgcctgt   3900

tgtcgagccc taggaaaatc atgaaacaca tgatagaaaa cccaactctt aagaagctct   3960

ggcaaggcga aacagaactt tttaaccagg gtgtcagcca gtccaaaata gtgaattcaa   4020

gaaaaattgg gctggaggaa ttacacaagg gcatgtgtgg cctcccaact gtagtgcaaa   4080

atttggtcat atatgcaaag aagaatgact ctctcatttt aggagagttg ggttaccccc   4140

ctggggacct caccagtgat gggtgggaaa ttttaggccc tggcagaatt ccaaagatca   4200

ctaatgtcga gtctgccaaa atggacttac tctccaaact catgaccttt ctggggattg   4260

aaagctcaag ggtccctaga accccagtcc actcaacaag gaaattactg aagatagtaa   4320

ggggcttgga aactggatgg gggtacactc acgcaggggg aatcagcagc gcaaaacacg   4380

ttacaggtga aaaaaacttg atgacccaca tggagggcag gaagggtaag tatatcctac   4440

aatcccaaga acatggtgcc gatgaggtag aatatggtgt aaaaactgac caaaaagcac   4500

ctgacaatgc cttatgctac tgctttaacc ctgaagccac aaacataaaa ggtgaaacgg   4560

gagccatggt gttcatgaag aagataggaa aaaaatggac tctcgtaaca tcagacggta   4620

acaaagccta ttataatgtg aacaacctga aagggtggtc tggactacca ataatgttgc   4680

actccaccgg ggccatagta gg                                             4702
```

<210> SEQ ID NO 26
<211> LENGTH: 4543
<212> TYPE: DNA
<213> ORGANISM: novel pestivirus

<400> SEQUENCE: 26

```
cggtggtgga cctgggggcc ggggccacca tgctccttta cggggtagac cttactgctt     60

gatagagtgc cggcggatgc ctcgggtaag agtataaaat ccgttgtcta ttaatatgga    120

aaaacagatc gcacattact taaaaaaaga aaaacaaaca aacggatgga cggaactggt    180

ggtaggagaa agtcatacaa aaataaccac gctctctgga aaaacctatc gaggaacttg    240

ggaaatggag aagcggtcaa atccttatgg aacctatctc cccagaccta gtccccaaca    300

gcttacagcc ctacaccccc acccagtggt aaattgcagg gtgatcgaat acaaggaaaa    360

tgaccctaat tatggtgatt gcccaaatac aaatggggtg ttcgtcgacg aaaaaggcag    420

gaggctgagt agccctccat tgggtatttg gaagataaga ttggactata gtgacctggt    480

gaacataaat agaccgaccc ccgctggtgg gaaaaactct taccgagtcg agacctgcag    540

tggggagctg gctactgtaa cactggtaca caaaagggta attgtggaag accgtagggg    600

attataccag tggaaaccca actgtgatgg gatggtgctc tatgtgaaaa cttgttctga    660

ttgggcagac caggtagaaa aacaggagaa ggaaagtccc ccaaaacctc agcggccacc    720

aaggcgagat ccccgaaaag ggttacaacc acaagtcccc aaagagattg aggttactga    780

aaagaagaga caacccagcg tcaccctagt atctgggggg cagaaggccc aagtcatcta    840

taaaggcagg actaagaata aaaggacccc ggatggggtc tataagtatc cgggagccaa    900

agaaggggat gtgacgaagg tcaggaagat gctaaagaat tggcatatag ccttggtaat    960

gtacctaata tatgttataa ccccaggttt cgccaaagtc cagtggttct taaaggatga   1020

aaactcgacg gggatcagtc agatactgtg gcaaagacag atcagcagat ccctgcatgg   1080

agaatggcct gatcagatct gccacggcat gccaaatgaa actattacgg atgaggaatt   1140
```

-continued

```
acgcagcctg ggaatgatag atacaagccc cagaacaaac tacacctgtt gccagttgca   1200
atatcacgag tggaagaaac atggctggtg taactatcca caaaaacaag cttggattag   1260
gagaataacg gccttacaag ccaacctcac cggagcttat gagggacccg agtgcgctgt   1320
catctgtcga ttcaatggca gctataacat cgtaaagcag gctagagatg aggtaagtcc   1380
gttgacaggg tgcaaggaag ggcacccctt cctattctct gacgaaagat ccgacacctc   1440
atgcctgagg cctccttcca ctagctgggt gagaccagta aaaatggacg aagcatcaat   1500
ggccgatggc tttgcccatg ggttgacaa ggcaataata ctaatcagaa aaggggcatc   1560
aggaatcatc aacttcttag acaccattgg gaggtggcta ccagtagctg aagcaactat   1620
aacaccatat tgtgaaactt acaccgtgac agggatgtat gtccatgtga agaattgcct   1680
ccccaaaggg ttacctaagc attcaaaaat aatttcccca acaatgatat atctggggga   1740
aggtgacccg gcccataata tccagcatct gtttggctca ggtatagcaa agtgggttct   1800
agtcttactc ggggttctgg gtgagtggta tggagaattg gcctctacaa tatacctgct   1860
actagagtat gggtctgagt ggttggaaca cgaaagtctg atcacggaag gattgattcc   1920
tggcatcaat atcacaatag aactcccagc cagtcataca gtgcctggtt gggtgtgggt   1980
cgcaggccag tgggtatgcg tgaaaccaga ctggtggcct acacagattt ggatcgaaac   2040
tgttgtggcg gaggcctggc atatactaaa aatactggca tcagccctgg tgaatatagt   2100
cactgcattt gtgaacctgg aattagtcta cctggtcata atactagtta aagtatcaaa   2160
ggggaacctg attggcgcta tactatggtg cctattgctg tcaggggctg aaggctcttg   2220
ccacaaaaga caagactatt acaatatcca gctagttgtc gaagaaaaga caggcgtaga   2280
aaaacgatct ataataggca agtggactgt gataaccaag gaaggtaggg aaccaagatt   2340
aatggagcaa ataaacatgg tgtcaaataa tagcctgtca gagacttact gctataatag   2400
gctaaatacc agcagttgga ggcggcaacc ggcaaatcag agagggtgtg gtcaaactgt   2460
gccctattgg cctggtgaca atgtcctaga ggaacaatac tatagcacag gttactgggt   2520
gaacgcaaca ggcggttgtc agctgaggga aggcgtatgg ctatcaagaa agggcaatgt   2580
acagtgccag cgtaacggct catccttgat gctgcaattg gcgataaaag aagaaaacga   2640
cactatggaa ataccatgtg acccggtgga aacagaaagc atgggtccag ttgcacaggg   2700
cacttgtgtg tacagctggg catttgcccc aagggggtgg tactataata ggaaagacgg   2760
ttactggctc caatacaaaa agaaaaacga ctaccagtac tggacaaaaa tgcccgctgc   2820
ctcgtccgcc gcaacaatgt accgccattt gctcccctta ctagtggcct gcctgatggg   2880
cggcaggata tcggtgtgga ttgtggcaat gctcctgtct ctacaggtgg aagccagtga   2940
agtgggtact aagcaactgg ctgtcactct aactctgtgg aaaatggact ggacagagct   3000
gcttttctat gttatcataa tgctagctgt taaggaagaa ctcgtaaaga aaatagtgac   3060
cgcaagcctt gtggccctaa aaaatagtcc agtagccttg agctttctta ttgttctcag   3120
gcttgtgggg ggcagtgaag cactcccagt gggtctacta ttagaaaaga tgtgtataga   3180
ccaaccggag ttcggaaccc ctttcctgat ctacctgtgg gacaattgga agtggactgt   3240
actagttagc ttctctgcac tgaatcatga aaaaactata aaactggcaa gaaaactgtt   3300
attggcaaca catataacag cactcacatt gaccggtctg agtgattcaa tcttttatgt   3360
aatgcttata acgaccaacc tactgataaa gacattcata tatttattgg gggctagcat   3420
gaattgggtt gagagagaaa aaaggaaatt actagtaaag aggagactaa tatataagaa   3480
agccgcaatt tgcaatcagg atgagaatga actggagaat aaatttaaca agataaccgt   3540
```

aaatacggat ttcaccccat gcaaacttga acttttgcaa ctactcaggg ctttttttagt 3600 ctcattatgt ttttcctatt acaagcctct cttgtatgca gagactaccc taactgttat 3660
agtgattggt gtacaagagt acaacgtagc tatggcccgc gggcgaagcg tggttcacag 3720
attgctagcc atggcctatt acatatatgg ccgcatgcag ggtgacatgt ttcagctcgc 3780
caccatccag tgcctgttgt cgagtccgag gaaagtcatg aagcacatga tagaaaatcc 3840
aactctcagg aagctctggc aaggcgaaac agaacttttt aaccagggtg tcagccagtc 3900
caaaatagtg aacccaaaga agattgggct agaagaatta cataagggta tgtgcggtct 3960
cccaaccgta gtccaaaact tggtcatata tgcaaagaag aatgactctc ttatcttagg 4020
ggagttgggt taccccccctg gggacctcac tagtgatggg tgggaaatat taggtcctgg 4080
cagaatccca aagattacca atgtcgagtc tgctaaaatg gacttactct ccaaactcat 4140
gacctttctg ggggattgaaa gctcaagggt ccccaggact ccagtccacc caacaaggaa 4200
attattgaag atagtaagag gcctggaaac tggatggggg tacactcatg caggggggaat 4260 aagcagcgca aaacatgtca caggtgaaaa aaacttgatg acccacatgg aaggccggaa 4320
gggcaagtat atcctacaat cccaagaaca tggtgctgac gaggtagaat atggagtaaa 4380
gactgatcaa aaagcacccg acaatgccct atgctactgc tttaaccctg aagccacaaa 4440
tataaaagga gaaacgggag ccatggtgtt catgaagaag ataggaaaaa aatggactct 4500
cgtaacatca gatggtaaca aggcctatta caatgtgaaa caa 4543

<210> SEQ ID NO 27
<211> LENGTH: 1073
<212> TYPE: DNA
<213> ORGANISM: novel pestivirus

<400> SEQUENCE: 27
ggcctggggg tcgggtccac catgcccctt taggggggtag accttactgc ttgatagagt 60
gccggcggat gcctcgggta agagtataaa atccgttgtt tgttaacatg gaaaaacaga 120
ttgtatatta cttaaaaaaa gaaaaacaaa gaaatgggtg gacggaattg gtggtaggag 180
aaagccatac aaaaataacc acactctctg gaaagaccta tcgaggtact tgggaaatgg 240
agaaacggtc gaatccttac ggaacctatc tccccagacc tagtcctcga cagcttacag 300
ccctacaccc ccacccagtg gtgaattgta aggtgactga gtacaaagag ctagacccta 360
attatggtga ctgcccaaat acaaacgggg tgttcatcga tgaaaagggt agaaggctga 420
gtagccctcc attgggcatt tggaagataa gactggacta cagcgacctg gtaaatataa 480
acaaaccagc ccccgctagt aggaaaaact cttatcgagt cgagacctgc agtggggagc 540
tggctactgt aacaccagta cacgacagag tgcttgtaga agactgcagg gggctatacc 600
aatggaaacc caattgtgaa ggaatggtgc tctatgtgaa aacttgttct gattgggcag 660
atcaggtaga aaaccaggag aaggaaagcc ccccaaaacc tcagcgacca ccgaggcgag 720
acccacgaaa aggattacaa ccacaagtcc ccaaagagac tgaggtcaca gaaaagaaga 780
gacaacccag cgtcacctta gtatcggggg ggcagaaggc ccaagtcatc tacaagggca 840
agactaagaa taaaaagact ccggatggag tctataagta tccaggagcc agagaaggag 900
atgtagtaaa ggttaggaag atgctgaaga attggcatat agctgtagtg atgtacctga 960
tctatatcat aaccccgagc tttgccaagg ttcagtggtt cttaaaggat gaaaactcga 1020
cggggattaa ccagatactg tggcaaagac agatcaatag atccctgcat gga 1073

<210> SEQ ID NO 28
<211> LENGTH: 5050
<212> TYPE: DNA
<213> ORGANISM: novel pestivirus

<400> SEQUENCE: 28
cctctagtac cacaggcacc gatagacggg gcaactcgaa cctgagagag aggtaccgaa 60
ctcttaagtc ccgagtacgg ggcagacgtc accgagtagt acacccaacg accaccactc 120
ctaggtgtag ggtctactga ggctcgggtg gacgtgggcg tgcccaaaga gaaatcggtg 180
gtggacctgg gggccggggc caccatgctc ctttacgggg tagaccttac tgcttgatag 240
agtgccggcg gatgcctcgg gtaagagtat aaaatccgtt gtctattaat atggaaaaac 300
agatcgcata ttacttaaaa aaagaaaaac aaacaaacgg atggacggaa ctggtggtag 360
gagaaagtca tacaaaaata accacgctct ctggaaaaac ctatcgagga acttgggaaa 420
tggagaagcg gtcaaatcct tatggaacct atctccccag acctagtccc caacagctta 480
cagccctaca cccccaccca gtggtgaatt gtaaggtgat cgaatacaag gagaaggacc 540
ctaattatgg cgattgccca aatacaaatg gggtgttcgt cgacgaaaaa ggcagaaggc 600
tgagtagccc tccattgggt atttggaaga taagattgga ctatagtgac ctggtgaaca 660
taaatagacc gacccccgct ggtgggaaaa actcttaccg agtcgagacc tgcagtgggg 720
agctggctac tgtaacactg gtacacaaaa gggtaattgt ggaagaccgt aggggattat 780
accagtggaa acccaactgt gatgggatgg tgctctatgt gaaaacttgt tctgattggg 840
cagaccaggt agaaaaacag gagaaggaaa gtcccccaaa acctcagcgg ccaccaaggc 900
gagatccccg aaaagggtta caaccacaag tccccaaaga gattgaggtt actgaaaaga 960
agagacaacc cagcgtcacc ctagtatctg gggggcagaa ggcccaagtc atctataaag 1020
gcaggactaa gaataaaagg accccggatg ggtctataa gtatccggga gccaaagaag 1080
gggatgtgac gaaggtcagg aagatgctaa agaattggca tatagccttg gtaatgtacc 1140
taatatatgt tataacccca ggtttcgcca aagtccagtg gttcttaaag gatgaaaact 1200
cgacggggat cagtcagata ctgtggcaaa gacagatcag cagatccctg catggagaat 1260
ggcctgatca gatctgccac ggcatgccaa atgaaactat tacggatgag gaattacgca 1320
gcctgggaat gatagataca agccccagaa caaactacac ctgttgccag ttgcaatatc 1380
acgagtggaa gaaacatggc tggtgtaact atccacaaaa acaagcttgg attaggagaa 1440
taacggcctt acaagccaac ctcaccggag cttatgaggg acccgagtgc gctgtcatct 1500
gtcgattcaa tggcagctat aacatcgtaa agcaggctag agatgaggta agtccgttga 1560
cagggtgcaa ggaagggcac cccttcctat tctctgacga aagatccgac acctcatgcc 1620
tgaggcctcc ttccactagc tgggtgagac cagtaaaaat ggacgaagca tcaatggccg 1680
atggctttgc ccatggggtt gacaaggcaa taatactaat cagaaaaggg gcatcaggaa 1740
tcatcaactt cctagacacc attggggggt ggctaccagt agctgaagca actataacac 1800
catattgtga aacttacacc gtgacaggga tgtatgtcca tgtgaagaat tgcctcccca 1860
aagggttacc taagcattca aaaataattt ccccaacaat gatatatctg ggggaaggtg 1920
acccggccca taatatccag catctgtttg gctcaggtat agcaaagtgg gttctagtct 1980
tactcggggt tctgggtgag tggtatggag aattggcctc tacaatatac ctgctactag 2040
agtatgagtc tgagtggttg gaacacgaaa gtctgatcac ggaaggattg attcctggca 2100
tcaatatcac aatagaactc ccagccagtc atacagtgcc tggttgggtg tgggtcgcag 2160
gccagtgggt atgcgtgaaa ccagactggt ggcctacaca gatttggatc gaaactgttg 2220
tggcggaggc ctggcatata ctaaaaatac tggcatcagc cctggtgaat atagtcactg 2280
catttgtgaa cctggaatta gtctacctgg tcataatact agttaaaata tcaaagggga 2340
acctgattgg cgctatacta tggtgcctat tgctgtcagg ggctgaaggc tcttgccaca 2400
aaagacaaga ctattacaat atccagctag ttgtcgaaga aaagacaggc gtagaaaaac 2460
gatctataat aggcaagtgg actgtgataa ccaaggaagg tagggaacca agattaatgg 2520
agcaaataaa catggtgtca aatgatagcc tgtcagagac ttactgctat aataggctaa 2580
ataccagcag ttggaggcgg caaccggcaa aacagagagg gtgtggtcaa actgtgccct 2640
attggcctgg tgacaatgtc ctagaggaac aatactatag cacaggttac tgggtgaacg 2700
caacaggcgg ttgtcagctg agggaaggcg tatggctatc aagaaagggc aatgtacagt 2760
gccagcgtaa cggctcatcc ttgatgctgc aattggcgat aaaagaagaa aacgacacta 2820
tggaaatacc atgtgacccg gtggaaacag aaagcatggg tccagttgca cagggcactt 2880
gtgtgtacag ctgggcattt gccccaaggg ggtggtacta taataggaaa gacggttact 2940
ggctccaata cataaagaaa aacgactacc agtactggac aaaaatgccc gctgcctcgt 3000
ccgccgcaac aatgtaccgc catttgctcc ccttactagt ggcctgcctg atgggcggca 3060
ggatatcggt gtggattgtg gcaatgctcc tgtctctaca ggtggaagcc agcgaagtgg 3120
gtactaagca actggctgtc actctaactc tgtggaaaat ggactggaca gagctgcttt 3180
tctatgttgt cataatgcta gctgttaagg aagaactcgt aaagaaaata gtgaccgcaa 3240
gccttgtggc cctaaaaaat agtccagtag ccttgagctt tcttattgtt ctcaggcttg 3300 tgggggcag tgaagcactc ccagtgggtc tactattaga aaagatgtgt atagaccaac 3360
cggagttcgg aacccctttc ctgatctacc tgtgggacaa ttggaagtgg actgtactag 3420
ttagcttctc tgcactgaat catgaaaaaa ctataaaact ggcaagaaaa ctgttattgg 3480
caacacatat aacagcactc acattgaccg gtctgagtga ttcaatcttt tatgtaatgc 3540
ttataacgac caacctactg ataaagacat tcatatattt attgggggct agcatgaatt 3600
gggttgagag agaaaaaagg aaattactag taaagaggag actaatatat aagaaagccg 3660
caatttgcaa tcaggatgag aatgaactgg agaataaatt taacaagata accgtaaata 3720
cggatttcac cccatgcaaa cttgaacttt tgcaactact cagggctttt ttagtctcat 3780
tatgtttttc ctattacaag cctctcttgt atgcagagac taccctaact gttatagtga 3840
ttggtgtaca agagtacaac gtagctatgg cccgcgggcg aagcgtggtt cacagattgc 3900
tagccatggc ctattacata tatggccgca tgcagggtga catgtttcag ctcgccacca 3960
tccagtgcct gttgtcgagt ccgaggaaag tcatgaagca catgatagaa aatccaactc 4020
tcaggaagct ctggcaaggc gaaacagaac tttttaacca gggtgtcagc cagtccaaaa 4080
tagtgaaccc aaagaagatt gggctagaag aattacataa gggtatgtgc ggtctcccaa 4140
ccgtagtcca aaacttggtc atatatgcaa agaagaatga ctctcttatc ttaggggagt 4200
tgggttaccc ccctggggac ctcactagtg atgggtggga aatattaggt cctggcagaa 4260
tcccaaagat taccaatgtc gagtctgcta aaatggactt actctccaaa ctcatgacct 4320
ttctggggat tgaaagctca agggtcccca ggactccagt ccacccaaca aggaaattac 4380
tgaagatagt aagaggcctg gaaactggat gggggtacac tcatgcaggg ggaataagca 4440
gcgcaaaaca tgtcacaggt gaaaaaaact tgatgaccca catggaaggc cggaagggca 4500

-continued agtatatcct acaatcccaa gaacatggtg ctgacgaggt agaatatgga gtaaagactg 4560
atcaaaaagc acccgacaat gccctatgct actgctttaa ccctgaagcc acaaatataa 4620
aaggagaaac gggagccatg gtgttcatga agaagatagg aaaaaaatgg actctcgtaa 4680
catcagatgg taacaaggcc tattacaatg tgaacaacct gaaagggtgg tctggactac 4740
caataatgtt gcactctact ggggccatag tagggaggat aaagtcagca tattcagatg 4800
aaaatgactt ggtggaggaa cttattgact ctaggactat cagcaagagc aatgagacaa 4860
acctggacca tcttatcaag gaattggcag atatgcggag gggggagttt cgctcaatca 4920
cccttggaac gggagctggg aaaactacgg aactgcccag gcaatatctc acaacggtag 4980
gtgcccataa atctgtgttg gtcctagtcc ctttaaaagc acccgccgag agtgtctgtc 5040
gcttcatgag 5050

<210> SEQ ID NO 29
<211> LENGTH: 4664
<212> TYPE: DNA
<213> ORGANISM: novel pestivirus

<400> SEQUENCE: 29
gcgtgcccaa agagaaatcg gtggtggacc tgggggtcgg gtccaccatg ccccttttagg 60 gggtagacct tactgcttga tagagtgccg gcggatgcct cgggtaagag tataaaatcc 120
gttgtctatt aacatggaaa agcagattgc atattactta aaaaaagaaa aacaaagaaa 180
tgggtggacg gaactggtag tgggagaaag ccatacgaaa ataaccacac tttctggaaa 240
gatctatcga ggtacatggg aaatggagaa acggtcgaat ccttacggaa cctatcttcc 300
tagacctagt cctcaacagc ttacagctct acaccccccac ccagtggtga attgtaaggt 360
gaccgagtat aaggagctgg accctaatta tggtgattgc ccgaagacaa atggggtatt 420
catcgacgaa aagggtcgaa ggctgagcag ccctccattg ggaatttgga agataagact 480
ggactacagc gacctggtaa atataaacag accagctctc gctagtggaa aaaactctta 540
tcgagtcgag acctgcagtg gggaactggc tattgtaaca ccggtacacg atagggtact 600
tgtagaagac tacagggggc tataccaatg gaaacccaac tgtgaaggaa tggtgctcta 660
tgtgaaaact tgctctgact gggcagacca ggtggaaaaa caggaaagag aaaacccccc 720
aaaacctcag cgaccaccga ggcgagaccc acgaaaaggg ttacaaccgc aagtccctaa 780
agagactgag gtcactgaaa agaggagaca acccagcgtt accttagtat cggggggaca 840
gaaggcccaa gtcatctaca aaggcaagac taagaataaa aagactccgg atggagtcta 900
taagtatcca ggagccagag aaggggatgt ggtaaaggtt aggaagatgc tgaagaattg 960
gcatatagct gtagcaatgt tcctgattta tatcataacc ccaggctttg ccaaggttca 1020
gtggttctta aaggatgaga actcgacggg gatcaatcag atactgtggc gaagacaaat 1080
caatagatcc ctgcatggag aatggcccaa ccagatctgc catggtatgc cgaatgaaac 1140
catcacggat gaggaattac gtagtctggg aatgatagat acaagtccca gaacaaacta 1200
cacttgttgc cagttgcaat atcatgagtg gaagaaacat ggttggtgca actatccaca 1260
aaaacagact tggattagga gaataacggc cctacaggct aacctcaccg gaacttatga 1320
gggacctgag tgcgctgtca tctgtcgatt taacggcagc tataacatcg taaaacaggc 1380
cagagacgag gtgagcccac tgacagggtg taaggagggg caccctttcc tattttctgg 1440
tgcaagatcc gacacctcgt gtctgaggcc tccttccact agttgggtca gaccagtgaa 1500
gatggatgag gcatcaatgg ccgatggctt tgcccatggg gttgacaagg caataatact 1560
aattagaaaa ggagcatcag gaattattaa tttcctagac actattggga ggtggctacc 1620
agtagccgaa gcaactatag taccatattg tgaaacttac actgtgacag ggatgtatat 1680
ccatgtgaag aattgcctcc ccaaagggtt acctaagcat tcaaaaataa tttccccgac 1740
aatgatatac ctgggggaag gtgacccagc ccataacatc cagcacttat ttggctcagg 1800
tatagcaaag tgggtcctag tcttactcgg ggtcctgggt gagtggtatg gagaattggc 1860
ctctacaata tacctactac tggagtacgg gtctgagtgg ttggaacatg aaagcttgat 1920
tacagaaggg ttgatccctg gcattaatat cacagtagaa ctcccagcta gccaaacagt 1980
gcctggttgg gtgtgggtcg caggccagtg ggtatgtgtg aagccagact ggtggcctac 2040
tcagatttgg attgaaaccg tggtggcgga ggcctggcat atactaaaaa tactggcatc 2100
agcccttgtg aacatagtca ctgcatttgt aaacttggaa ttggtctacc tggtcataat 2160
attagtcaaa atatcaaagg ggaacctaat aggcgccata ttatggtgcc tattattgtc 2220
aggggctgaa ggctcatgcc acaaaagaca agactattac aatattcagt tagttgtcga 2280
agaaaaaaca ggtgtagaaa aacgatccat aatgggcaaa tggactgtaa taactaggga 2340
aggtcgggaa ccaagattaa tggagcaaat aaatatggtg ttcaacgata gcctgtcaga 2400
aacttactgc tataataggc taaacaccag tagttggggg cgacaaccgg caagacagag 2460
agggtgtggt cagactgtac cctattggcc tggtgacaat gtcctagaag aacaatacta 2520
tagcactggt tactgggtga acacaacagg cggttgccag ttgagagaag gagtgtggct 2580
atcaagaaaa ggcaacgtac agtgccagcg taatggctca tccttgatac tgcaattagc 2640
aataaaagaa gagaatgaca ctatggaaat accatgtgac ccggtggaaa cagaaagcat 2700
gggtccagtt gcacagggta cttgcgtata tagctgggca ttcgccccaa gagggtggta 2760
ttataatagg aaagacggtt attggcttca gtacataaag aaaaacgact accagtactg 2820
gacaaaaatg cctaccgcct cgtccgctgc aacaatgtac cgccatttgc ttcccttact 2880
ggtagcttgc ctcatgggcg gcaggatatc ggtgtggatt gtagcaatgc tcctatctct 2940
acaggtggaa gctagcgaag tgggtaccaa gcaactggct gtcacactaa ctctgtggaa 3000
aatggactgg acagaactac tcttttatat tgttataatg ctagccatca aggaagagct 3060
cataaagaaa atagtgactg caagcctagt agccttaaaa aatagtccag tggctttgag 3120
ttttcttatt gtactcaggc ttgtaggggg cagtgaagca ctcccagtag gtttactgct 3180
agaaaagatg tgtatagacc aaccggagtt tggaacccct ttcctgatct acctgtggga 3240
caattggaag tggactgtac tagtcagctt ctccgcactg aaccatgaaa aaactataaa 3300
actggcaaga aaactgctac tggccacgca tataacagcg ctcacattga ctggtctgag 3360
tgattcaatc ttctacatga tgcttataat gaccaaccta ctgataaaga cattcatata 3420
tctactgggg gccagcataa attgggtcga gaaagaaaaa agaaaattgc tggcgaagag 3480
gaaattaata tataagaaag ccgcgatttg caatcatgaa gagaatgaat tggagaataa 3540
atttaacagg ataactgtaa atgcggactt caccccatgc aaactcgaac ttctacaatt 3600
acttagggct tttttagtct ctttatgttt ttcctattat aagcctcttc tgtatgcaga 3660
gaccacccta actgttatag taattggcgt acaagagtac aatgtagcaa tggcccgtgg 3720
gcgaagtgtg gtccatagac tactagccat ggcctactac atatatggcc gcatacaggg 3780
tgaaatgttc caactcgcca ctatccagtg cctgttgtca agcccgagga aaattatgaa 3840
acacatgata gaaaatccaa ctcttaagaa gctctggcaa ggcgaaacag aacttttttaa 3900

-continued

```
ccagggtgtc agccagtcca aaatagtgaa tccaaggaaa attgggctgg gggaattaca   3960

taagggcatg tgcggcctcc caactgtagt gcaaaatcta gtcatatatg caaagaagaa   4020

tgactctctc attttaggag agttgggtta ccccccctggg gacctcacca gtgatgggtg   4080

ggaaatttta ggtcctggca gaatcccaaa aatcactaat gttgagtccg caaaaatgga   4140

cttactctcc aaactcatga ccttcttggg gattgaaagc tcaagagtcc ccagaacccc   4200

agtccactca acaagaaagt tattgaagat agtaagaggc ctcgaaactg gatgggggta   4260

cactcatgca ggaggaatca gtagcgcaaa acacgttaca ggtgagaaga acttgatgac   4320

ccacatggag ggtaggaagg gtaagtatat cctacaatcc caagaacatg gcgctgatga   4380

ggtagaatat ggggtgaaaa ctgaccaaaa agcacccgac aatgccttgt gctactgctt   4440

taaccctgaa gccacaaaca taaaaggtga aacgggagcc atggtgttca tgaagaagat   4500

aggaaaaaaa tggactcttg taacatcgga tggtaacaaa gcctattaca atgtaaacaa   4560

cttgaaaggg tggtctggac ttccaataat gttgcactcc accggggcca tagtagggag   4620

gattaagtca gcatattcgg atgaaaatga cttggtggag gaac                     4664


<210> SEQ ID NO 30
<211> LENGTH: 16
<212> TYPE: DNA
<213> ORGANISM: artificial sequence
<220> FEATURE:
<223> OTHER INFORMATION: primer

<400> SEQUENCE: 30

gtaaaacgac ggccag                                                      16


<210> SEQ ID NO 31
<211> LENGTH: 17
<212> TYPE: DNA
<213> ORGANISM: artificial sequence
<220> FEATURE:
<223> OTHER INFORMATION: primer

<400> SEQUENCE: 31

caggaaacag ctatgac                                                     17


<210> SEQ ID NO 32
<211> LENGTH: 211
<212> TYPE: PRT
<213> ORGANISM: novel virus

<400> SEQUENCE: 32

Ser Cys His Lys Arg Gln Asp Tyr Tyr Ser Ile Gln Leu Val Val Asp
1               5                   10                  15

Gly Lys Thr Gly Val Glu Lys Arg Ser Ile Val Gly Lys Trp Thr Val
            20                  25                  30

Ile Thr Arg Glu Gly Arg Glu Pro Arg Leu Met Glu Gln Ile Ser Met
        35                  40                  45

Val Ser Asn Asp Ser Leu Ser Glu Thr Tyr Cys Tyr Asn Arg Leu Asn
    50                  55                  60

Thr Ser Ser Trp Gly Arg Gln Pro Ala Arg Gln Arg Gly Cys Gly Gln
65                  70                  75                  80

Thr Val Pro Phe Trp Pro Gly Asp Asn Val Leu Glu Glu Gln Tyr Tyr
                85                  90                  95

Ser Thr Gly Tyr Trp Val Asn Ala Thr Gly Gly Cys Gln Leu Arg Glu
            100                 105                 110
```

-continued

```
Gly Val Trp Leu Ser Arg Lys Gly Asn Val Gln Cys Gln Arg Asn Gly
        115                 120                 125

Ser Ser Leu Ile Leu Gln Leu Ala Ile Lys Glu Glu Asn Asp Thr Met
    130                 135                 140

Glu Ile Pro Cys Asp Pro Val Glu Thr Glu Ser Met Gly Pro Val Thr
145                 150                 155                 160

Gln Gly Thr Cys Val Tyr Ser Trp Ala Phe Ala Pro Arg Gly Trp Tyr
                165                 170                 175

Tyr Asn Arg Lys Asp Gly Tyr Trp Leu Gln Tyr Val Lys Lys Asn Asp
            180                 185                 190

Tyr Gln Tyr Trp Thr Lys Met Pro Thr Ala Ser Ser Ala Thr Thr Met
        195                 200                 205

Tyr Arg His
    210
```

<210> SEQ ID NO 33
<211> LENGTH: 681
<212> TYPE: DNA
<213> ORGANISM: artificial sequence
<220> FEATURE:
<223> OTHER INFORMATION: baculo-adapted DNA

<400> SEQUENCE: 33

```
cgcggatcca aatatgtcat gtcacaagcg tcaagactac tactctatcc aactggtggt     60

ggacggaaaa actggcgtgg aaaagcgttc tatcgtgggc aagtggacgg tcatcaccag    120

ggagggcaga gaaccgcgcc taatggagca aatttcgatg gtatctaacg actctctttc    180

agaaacctac tgctataacc gtctcaatac tagctcttgg ggtcgtcaac ctgcccgtca    240

gcgcggatgt gggcaaaccg tccccttctg gcctggtgac aacgtactcg aggaacagta    300

ctatagcacc ggatactggg ttaacgctac tggcggttgc caactacgcg agggagtttg    360

gttatctcgt aaggggaacg tgcaatgtca gcgtaatggc tcatcgctga tccttcaact    420

cgctattaaa gaggaaaacg acaccatgga aatcccgtgc gatccagtcg agactgaatc    480

aatgggcccc gttactcaag gcacgtgtgt gtacagctgg gctttcgccc ctaggggatg    540

gtactataac cgtaaggacg gctactggct tcaatacgtg aagaaaaacg attaccagta    600

ctggaccaaa atgcccactg catccagcgc gaccactatg taccgtcacc atcaccatca    660

ccatcactaa gaattctcga g                                              681
```

<210> SEQ ID NO 34
<211> LENGTH: 666
<212> TYPE: DNA
<213> ORGANISM: artificial sequence
<220> FEATURE:
<223> OTHER INFORMATION: artificial DNA

<400> SEQUENCE: 34

```
catatgtcgt gtcacaaacg ccaagattat tattctattc aactggtcgt ggatggtaaa     60

acgggtgtcg aaaaacgctc tatcgtcggt aaatggaccg tgattacgcg tgaaggccgc    120

gaaccgcgtc tgatggaaca gatcagtatg gtttccaacg atagcctgtc tgaaacctat    180

tgctacaacc gcctgaatac gagctcttgg ggtcgtcagc cggcacgtca acgcggctgt    240

ggtcagaccg tcccgttttg gccgggcgac aacgtgctgg aagaacaata ttacagtacc    300

ggttattggg tgaatgcaac gggcggttgc cagctgcgtg aaggcgtttg gctgtctcgt    360

aagggtaacg tccagtgtca acgcaatggc agttccctga ttctgcaact ggcgatcaaa    420
```

-continued

```
gaagaaaacg ataccatgga aatcccgtgc gacccggtcg aaaccgaatc aatgggcccg    480

gtgacccagg gcacgtgtgt ttattcgtgg gcattcgcac cgcgcggctg gtattacaac    540

cgtaaagatg gttattggct gcagtacgtg aagaaaaacg actatcaata ctggaccaaa    600

atgccgacgg catcatcggc taccacgatg taccgtcatc accatcacca tcaccattaa    660

ctcgag                                                               666


<210> SEQ ID NO 35
<211> LENGTH: 20
<212> TYPE: DNA
<213> ORGANISM: artificial sequence
<220> FEATURE:
<223> OTHER INFORMATION: Q-pcr primer

<400> SEQUENCE: 35

cgtgcccaaa gagaaatcgg                                                 20


<210> SEQ ID NO 36
<211> LENGTH: 20
<212> TYPE: DNA
<213> ORGANISM: artificial sequence
<220> FEATURE:
<223> OTHER INFORMATION: Q-pcr primer

<400> SEQUENCE: 36

ccggcactct atcaagcagt                                                 20
```

UNITED STATES PATENT AND TRADEMARK OFFICE
CERTIFICATE OF CORRECTION

| | | Page 1 of 1 |
|---|---|---|
| PATENT NO. | : 10,954,491 B2 | |
| APPLICATION NO. | : 15/535819 | |
| DATED | : March 23, 2021 | |
| INVENTOR(S) | : de Groof et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 557 days.

Signed and Sealed this
Tenth Day of January, 2023

Katherine Kelly Vidal
*Director of the United States Patent and Trademark Office*